United States Patent
Cutaia

(10) Patent No.: US 10,136,859 B2
(45) Date of Patent: Nov. 27, 2018

(54) SYSTEM AND METHOD FOR OUTPATIENT MANAGEMENT OF CHRONIC DISEASE

(71) Applicant: Michael Cutaia, Brooklyn, NY (US)

(72) Inventor: Michael Cutaia, Brooklyn, NY (US)

(*) Notice: Subject to any disclaimer, the term of this patent is extended or adjusted under 35 U.S.C. 154(b) by 168 days.

(21) Appl. No.: 14/976,352

(22) Filed: Dec. 21, 2015

(65) Prior Publication Data

US 2016/0174903 A1    Jun. 23, 2016

Related U.S. Application Data

(60) Provisional application No. 62/096,083, filed on Dec. 23, 2014.

(51) Int. Cl.
*A61B 5/00* (2006.01)
*A61B 5/145* (2006.01)
(Continued)

(52) U.S. Cl.
CPC .......... *A61B 5/7271* (2013.01); *A61B 5/0488* (2013.01); *A61B 5/0816* (2013.01); *A61B 5/1118* (2013.01); *A61B 5/14542* (2013.01); *A61B 5/4836* (2013.01); *A61M 16/0051* (2013.01); *A61M 16/026* (2017.08);
(Continued)

(58) Field of Classification Search
CPC ....... G06F 3/015; G06F 1/163; G06F 19/3406
See application file for complete search history.

(56) References Cited

U.S. PATENT DOCUMENTS 6,186,142 B1   2/2001   Schmidt et al.
6,306,088 B1   10/2001  Krausman et al.
(Continued)

FOREIGN PATENT DOCUMENTS

EP   2012857 A2   1/2009
EP   2129433 A1   12/2009
(Continued)

OTHER PUBLICATIONS

Abudagga, Azza, et al., "Exacerbations among chronic bronchitis patients treated with maintenance medications from a US managed care population: an administrative claims data analysis," 2013, International Journal of COPD, vol. 8 (pp. 175-185).
(Continued)

*Primary Examiner* — Scott T Luan
(74) *Attorney, Agent, or Firm* — Harris Beach PLLC

(57) ABSTRACT

An outpatient ambulatory patient worn apparatus for managing chronic lung disease includes a plurality of sensors configured to be worn by a patient and to measure a plurality of physiological data. The plurality of sensors includes at least an oximeter, a respiratory rate sensor, and at least one activity or motion sensor. A central monitoring unit (CMU) is worn by the patient in an outpatient setting during activities of daily living. The CMU categorizes each recorded measurement of each of the plurality of sensors stored in a set of time stamped primary data by a predominate activity type to generate a set of activity type stamped data, the predominate activity types include rest, exertion, and sleep. A generate report process provides at least one or more reports. An outpatient ambulatory patient worn long-term oxygen therapy (LTOT) apparatus and a method for managing chronic lung disease are also described.

20 Claims, 21 Drawing Sheets

(51) Int. Cl.

| | | |
|---|---|---|
| *A61M 16/20* | (2006.01) | |
| *A61B 5/11* | (2006.01) | |
| *A61B 5/0488* | (2006.01) | |
| *A61M 16/10* | (2006.01) | |
| *G06F 19/00* | (2018.01) | |
| *A61B 5/08* | (2006.01) | |
| *A61M 16/00* | (2006.01) | |
| *G16H 10/60* | (2018.01) | |
| *G16H 40/40* | (2018.01) | |

(52) U.S. Cl.
CPC ...... *A61M 16/1005* (2014.02); *A61M 16/204* (2014.02); *G06F 19/00* (2013.01); *G16H 10/60* (2018.01); *G16H 40/40* (2018.01); *A61M 16/101* (2014.02); *A61M 2202/0208* (2013.01); *A61M 2205/3334* (2013.01); *A61M 2230/42* (2013.01); *A61M 2230/63* (2013.01)

(56) References Cited

U.S. PATENT DOCUMENTS

| | | |
|---|---|---|
| 6,371,114 B1 | 4/2002 | Schmidt et al. |
| 6,416,471 B1 | 7/2002 | Kumar et al. |
| 6,532,958 B1 | 3/2003 | Buan et al. |
| 6,561,187 B2 | 5/2003 | Schmidt et al. |
| 7,013,898 B2 | 3/2006 | Rashad et al. |
| 7,222,624 B2 | 5/2007 | Rashad et al. |
| 7,331,343 B2 | 2/2008 | Schmidt et al. |
| 7,508,307 B2 | 3/2009 | Albert |
| 7,621,270 B2 | 11/2009 | Morris et al. |
| 7,954,493 B2 | 6/2011 | Nawata |
| 7,970,470 B2 | 6/2011 | Hartley et al. |
| 8,066,004 B2 | 11/2011 | Morris et al. |
| 8,074,646 B2 | 12/2011 | Daly |
| 8,092,393 B1 | 1/2012 | Rulkov et al. |
| 8,397,725 B2 | 3/2013 | Slaker et al. |
| 8,437,854 B2 | 5/2013 | Mass et al. |
| 8,448,640 B2 | 5/2013 | Bassin |
| 8,463,576 B2 | 6/2013 | Yuen et al. |
| 8,465,434 B2 | 6/2013 | Mason et al. |
| 8,478,418 B2 | 7/2013 | Fahey |
| 8,498,683 B2 | 7/2013 | Price et al. |
| 8,517,014 B2 | 8/2013 | Farrell et al. |
| 8,523,785 B2 | 9/2013 | Kaushal et al. |
| 8,540,629 B2 | 9/2013 | Jain et al. |
| 2003/0199945 A1 | 10/2003 | Ciulla |
| 2004/0159323 A1 | 8/2004 | Schmidt et al. |
| 2005/0010125 A1 | 1/2005 | Joy et al. |
| 2006/0213519 A1 | 9/2006 | Schmidt et al. |
| 2006/0225737 A1 | 10/2006 | Iobbi |
| 2008/0269812 A1* | 10/2008 | Gerber ............... A61N 1/36514 607/2 |
| 2009/0050152 A1 | 2/2009 | Iobbi |
| 2009/0076405 A1 | 3/2009 | Amurthur et al. |
| 2010/0041970 A1 | 2/2010 | Hedberg et al. |
| 2010/0083968 A1 | 4/2010 | Wondka et al. |
| 2011/0263997 A1 | 10/2011 | Corn |
| 2013/0092165 A1* | 4/2013 | Wondka ............... A61M 15/08 128/204.25 |
| 2013/0116520 A1 | 5/2013 | Roham et al. |
| 2013/0184540 A1* | 7/2013 | Boschetti Sacco .... A61B 5/087 600/301 |
| 2013/0273586 A1 | 10/2013 | Turino et al. |
| 2013/0281800 A1 | 10/2013 | Saroka et al. |
| 2014/0163393 A1 | 6/2014 | McCombie et al. |
| 2014/0275857 A1 | 9/2014 | Toth et al. |

FOREIGN PATENT DOCUMENTS

| | | |
|---|---|---|
| EP | 2393422 A1 | 12/2011 |
| EP | 2440285 A1 | 4/2012 |
| WO | WO-2010091168 A1 | 8/2010 |
| WO | WO-2012077113 A2 | 6/2012 |
| WO | WO-2013080109 A2 | 6/2013 |
| WO | WO-2014174477 A1 | 10/2014 |

OTHER PUBLICATIONS

Agusti, Alvar G. N., "Systemic Effects of Chronic Obstructive Pulmonary Disease," 2005, Proceedings of the American Thoracic Society, vol. 2 (pp. 367-370).

Arnold, Elizabeth, et al., "Ambulatory oxygen: why do COPD patients not use their portable systems as prescribed? A qualitative study," 2011, BMC Pulmonary Medicine, vol. 11, No. 9 (pp. 1-7).

Beauchamp, Marla K., et al., "Systematic Review of Supervised Exercise Programs After Pulmonary Rehabilitation in Individuals With COPD," 2013, Chest, vol. 144, No. 4 (pp. 1124-1133).

Bliss, Peter L., et al., "Characteristics of Demand Oxygen Delivery Systems: Maximum Output and Setting Recommendations," 2004, Respiratory Care, vol. 49, No. 2 (pp. 160-165).

Braun, Sheldon R., et al. "Comparison of Six Oxygen Delivery Systems for COPD Patients at Rest and During Exercise*," 1992, Chest, vol. 102. No. 3 (pp. 694-698).

Casanova, Ciro, et al., "Twenty-Four-Hour Ambulatory Oximetry Monitoring in COPD Patients With Moderate Hypoxemia," 2006, Respiratory Care, vol. 51, No. 12 (pp. 1416-1423).

Casanova, Ciro, et al., "Distance and Oxygen Desaturation During the 6-min Walk Test as Predicators of Long-term Mortality in Patients With COPD," 2008, Chest, vol. 134, No. 4 (pp. 746-752).

Centers for Disease Control and Prevention, Morbidity and Mortality Weekly Report, "Suffocation Deaths Associated with Use of Infant Sleep Positioners—United States, 1997-2011," Nov. 23, 2012, vol. 61, No. 46 (pp. 934-955).

Celli, Bartolome R., et al., "Predictors of Survival in COPD: More than Just the $FEV_1$," 2008, Journal of Respiratory Medicine, vol. 102, Supplement 1 (pp. S27-S35).

Christopher, Kent L., et al., "Long-term Oxygen Therapy," 2011, Chest, vol. 139 (pp. 430-434).

Connors, Alfred F., et al., "Outcomes Following Acute Exacerbation of Severe Chronic Obstructive Lung Disease," 1996, Am J Respir Crit Care Med, vol. 154 (pp. 959-967).

Cranston, Josephine M., et al., "Models of chronic disease management in primary care for patients with mild-to-moderate asthma or COPD: a narrative review," 2008, MJA, vol. 188, No. 8 (pp. S50-S52).

Cutaia, Michael, "Ambulatory Monitoring of Oxygen Saturation in Chronic Lung Disease: Optimizing Long-Term Oxygen Therapy," 2002, Clinical Pulmonary Medicine, vol. 9, No. 6 (pp. 297-305).

Cutaia, Michael, et al. "The Relationship of the BODE Index to Oxygen Saturation During Daily Activities in Patients with Chronic Obstructive Pulmonary Disease," 2011, Lung, vol. 189 (pp. 269-277).

Pilling, Jeffrey, et al., "Ambulatory Oximetry Monitoring in Patients With Severe COPD: A Preliminary Study," 1999, Chest, vol. 116 (pp. 314-321).

Aoyagi, Yukitoshi, et al., "Habitual physical activity and health-related quality of life in older adults: interactions between the amount and intensity of activity (the Nakanojo Study)," 2010, Qual Life Res, vol. 19, (pp. 333-338).

Demeyer, Heleen, et al., "Standardizing the Analysis of Physical Activity in Patients With COPD Following a Pulmonary Rehabilitation Program," 2014, Chest, vol. 146, No. 2 (pp. 318-327).

Ford, Earl S., et al., "Total and State-Specific Medical and Absenteeism Costs of COPD Among Adults Aged ≥ 18 Years in the United States for 2010 and Projections Through 2020," 2015, CHEST, vol. 147, No. 1 (pp. 31-45).

Gloeckl, Rainer, et al., "Practical recommendations for exercise training patients with COPD," 2013, European Respiratory Review, vol. 22, No. 128 (pp. 178-186).

Gorecka, Dorota, et al., "Effect of long term oxygen therapy on survival in patients with chronic obstructive pulmonary disease with moderate hypoxaemia," 1997, Thorax, vol. 52 (pp. 674-679).

(56) References Cited

OTHER PUBLICATIONS

Reilly, Charles C., et al., "Neural respiratory drive, pulmonary mechanics and breathlessness in patients with cystic fibrosis," 2011, Thorax, vol. 66 (pp. 240-246).
Vaes, Anouk W., et al., "Effect of 'activity monitor-based' counseling on physical activity and health-related outcomes in patients with chronic diseases: A systematic review and meta-analysis," 2013, Annals of Medicine, vol. 45 (pp. 397-412).
Watz, Henrik, et al., "Extrapulmonary Effects of Chronic Obstructive Pulmonary Disease on Physical Activity, 2008, American Journal of Respiratory and Critical Care Medicine," vol. 177 (pp. 743-751).
Furlanetto, Karina C., et al., "Step Counting and Energy Expenditure Estimation in Patients With Chronic Obstructive Pulmonary Disease and Healthy Elderly: Accuracy of 2 Motion Sensors," 2010, Arch. Phys. Med. Rehabil., vol. 91 (pp. 261-267).
Fussell, Kevin M., et al., "Assessing Need for Long-Term Oxygen Therapy: A Comparison of Conventional Evaluation and Measures of Ambulatory Oximetry Monitoring," 2003, Respiratory Care, vol. 48, No. 2 (pp. 115-119).
Garcia-Aymerich, J., et al., "Risk factors of readmission to hospital for a COPD exacerbation: a prospective study," 2003, Thorax, vol. 58 (pp. 100-105).
Garcia-Aymerich, J., et al., "Regular physical activity reduces hospital admission and mortality in chronic obstructive pulmonary disease: a population based cohort study," 2006, Thorax, vol. 61 (pp. 772-778).
Garcia-Rio, F., et al., "Daily Physical Activity in Patients with Chronic Obstructive Pulmonary Disease Is Mainly Associated with Dynamic Hyperinflation," 2009, American Journal of Respiratory and Critical Care Medicine, vol. 180 (pp. 506-512).
Garcia-Rio, F., et al., "Prognostic Value of the Objective Measurement of Daily Physical Activity in Patients With COPD," 2012, Chest, vol. 142, No. 2 (pp. 338-346).
Gracia-Talavera, Ignacio, et al., "Time to desaturation in the 6-min walking distance test predicts 24-hour oximetry in COPD patients with $PO_2$ between 60 and 70 mmHg," 2008, Respiratory Medicine, vol. 102 (pp. 1026-1032).
Gibson, C. Michael, et al., "Diagnostic and prognostic value of ambulatory ECG (Holter) monitoring in patients with coronary heart disease: a review," 2007, J Thromb Thrombolysis, vol. 23 (pp. 135-145).
Grasso, Marc E., et al., "Capitation, Managed Care, and Chronic Obstructive Pulmonary Disease," 1998, American Journal of Respiratory and Critical Care Medicine, vol. 158 (pp. 133-138).
Guyatt, Gordon H., et al., "A Randomized Trial of Strategies for Assessing Eligibility for Long-Term Domiciliary Oxygen Therapy," 2005, American Journal of Respiratory and Critical Care Medicine, vol. 172 (pp. 573-580).
Halpin, David M. G., et al., "Chronic Obstructive Pulmonary Disease the Disease and Its Burden to Society," 2006, Proceedings of the American Thoracic Society, vol. 3 (pp. 619-623).
Heiermann, Stefanie, et al., "Accuracy of a Portable Multisensor Body Monitor for Predicting Resting Energy Expenditure in Older People: A Comparison with Indirect Calorimetry," 2011, Gerontology, vol. 57 (pp. 473-479).
Katsenos, Stamatis, et al., "Long-Term Oxygen Therapy in COPD: Factors Affecting and Ways of Improving Patient Compliance," 2011, Pulmonary Medicine, vol. 2011 (pp. 1-8).
McCoy, Robert W., et al., "Product Performance Variability With Home Portable Oxygen Systems May Impact Patient Performance Outcomes: It May Be the Device, Not the Disease," 2009, Respiratory Care, vol. 54, No. 3 (pp. 324-326).
Petty, Thomas L., et al., "Long Term Oxygen Therapy (LTOT), History, Scientific Foundations, and Emerging Technologies," 6th Oxygen Consensus Conference Recommendations, National Lung Health Education Program (pp. 1-36).
Menn, Petra, et al., "Direct medical costs of COPD—An excess cost approach based on two population-based studies," 2012, Respiratory Medicine, vol. 106, (pp. 540-548).
Michard, Frederic, et al., "Relation between Respiratory Changes in Arterial Pulse Pressure and Fluid Responsiveness in Septic Patients with Acute Circulatory Failure," 2000, American Journal of Respiratory and Critical Care Medicine, vol. 162 (pp. 134-138).
Morrison, D., et al., The adequacy of oxygenation in patients with hyppoxic chronic obstructive pulmonary disease treated with long-term domiciliary oxygen, 1997, Respiratory Medicine, vol. 91 (pp. 287-291).
Morrison Informatics, Inc., A Comprehensive Cost Analysis of Medicare Home Oxygen Therapy, A Study for the American Association for Homecare, Jun. 27, 2006 (pp. 1-20).
Oba, Yuji, Cost-Effectiveness of Long-Term Oxygen Therapy for Chronic Obstructive Pulmonary Disease, 2009, The American Journal of Managed Care, vol. 15, No. 2 (pp. 97-104).
Palwai, Aishwarya, et al., "Cirtical Comparisons of the Clinical Performance of Oxygen-conserving Devices," 2010, American Journal of Respiratory and Critical Care Medicine, vol. 181 (pp. 1061-1071).
Papazoglou, Dimitrios, et al., Evaluation of a Multisensor Armband in Estimating Energy Expenditure in Obese Individuals, 2006, Obesity, vol. 14, No. 12 (pp. 2217-2223).
Pasquale, Margarget, et al., "Impact of exacerbations on health care cost and resource utilization in chronic obstructive pulmonary disease patients with chronic bronchitis from a predominantly Medicare population," 2012, International Journal of COPD, vol. 7 (pp. 757-764).
Puhan, Milo A., et al., "Expansion of the prognostic assessment of patients with chronic obstructive pulmonary disease: the updated BODE index and the ADO index," 2009, Lancet, vol. 374 (pp. 704-711).
Rabe, Klaus F., et al., "Global Strategy for the Diagnosis, Management, and Prevention of Chronic Obstructuve Pulmonary Disease," 2007, American Journal of Respiratory and Critical Care Medicine, vol. 176 (pp. 532-555).
Rice, Kathryn L., et al., "Accu"$_2$ Oximetry-Driven Oxygen-Conserving Device Versus Fixed-Dose Oxygen Devices in Stable COPD Patients," 2011, Respiratory Care, vol. 56, No. 12 (pp. 1901-1905).
Ringbaek, T.J., et al., "Does long-term oxygen therapy reduce hospitalisation in hypoxaemic chronic obstructive pulmonary disease?" 2002, European Respiratory Journal, vol. 20 (pp. 38-42).
Ringbaek, Thomas, J., et al., "Outdoor activity and performance status as predictors of survival in hypoxaemic chronic obstructive pulmonary disease (COPD)," 2005, Clinical Rehabilitation, vol. 19 (pp. 331-338).
Ringbaek, Thomas J., et al., "The impact of the Danish Oxygen Register on adherence to guidelines for long-term oxygen therapy in COPD patients," 2006, Respiratory Medicine, vol. 100, (pp. 218-225).
Schenkel, N. Soguel, et al., "Oxygen saturation during daily activities in chronic obstructive pulmonary disease," 1996, European Respiratory Journal, vol. 9 (pp. 2584-2589).
Sliwinski, P., et al., "The adequacy of oxygenation in COPD patients undergoing long-term oxygen therapy assessed by pulse oximetry at home," 1994, European Respiratory Journal, vol. 7 (pp. 274-278).
Spruit, Martijn A., et al. "Maintenance Programs After Pulmonary Rehabilitation: how may we advance this field?" 2013, Chest, vol. 144 (pp. 1092-1092).
Stoller, James K., et al., "Oxygen Therapy for Patients With COPD: Current Evidence and the Long-Term Oxygen Treatment Trial," 2010, Chest, vol. 138 (pp. 179-187).
Waschki, Benjamin, et al., "Physical activity monitoring in COPD: Compliance and associations with clinical characteristics in a multicenter study," 2012, Respiratory Medicine, vol. 106 (pp. 522-530).
Waschki, Benjamin, et al., "Physical Activity Is the Strongest Predictor of All-Cause Mortality in Patients With COPD: A Prospective Cohort Study," 2011, Chest, vol. 140 (pp. 331-342).
Wouters, Emiel F. M., et al., "Survival and Physical Activity in COPD: A Giant Leap Forward!" 2011, Chest, vol. 140 (pp. 279-281).
Yoon, Ho II, et al., "Confronting the Colossal Crisis of COPD in China," 2011, Chest, vol. 139, No. 4 (pp. 735-736).

(56) References Cited

OTHER PUBLICATIONS

Zielinski, J., et al., "Causes of death in patients with COPD and chronic respiratory failure," 1997, Monaldi Arch. Chest Dis., vol. 52, No. 1 (pp. 43-47).
International Searching Authority, International Search Report and Written Opinion for Corresponding International Application No. PCT/US15/67321, dated Mar. 11, 2016 (10 pgs).
European Patent Office, Extended European Search Report for Corresponding European Patent Application No. 15874293.2, dated Jun. 20, 2018 (7 pgs).

* cited by examiner

CLINICAL REPORT:

TEMPORAL PROFILE OF OXYGENATION AND PHYSICAL ACTIVITY

TEMPORAL PROFILE OF OXYGENATION AND PHYSICAL ACTIVITY

OXYGENATION SATURATION

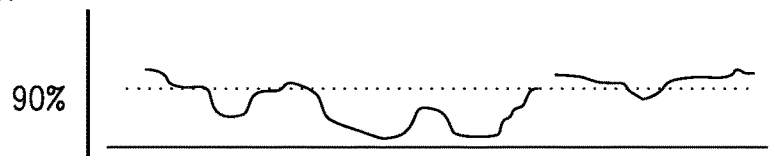

90%

ACTIVITY:   R   E   E   E   S

CHAN 1:

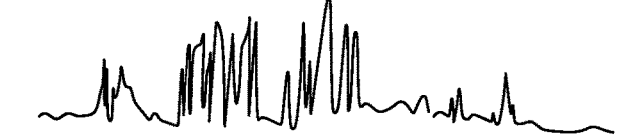

CHAN 2:

TIME OF DAY:   8AM   12NOON   8PM   12MIDNITE   8AM

OXYGENATION PROFILE: % TIME<90% SATURATION (min)

REST: 1% (1min)
    EXERTION: 99% (420min)
    SLEEP: 5% (30min)

PATIENT INFO:
    NAME:        AGE:            TOTAL RECORDING TIME:
    ID:          GENDER:         ANALYSIS DATE:
    EMAIL:       WEIGHT/BMI:     REPORT DATE:
    ADDRESS:

FIG.4B

CLINICAL REPORT:

FREQUENCY, DURATION, AND MAGNITUDE OF HYPOXEMIC EVENTS

OXYGEN SATURATION

[Graph showing oxygen saturation over time, values between 80-100]

TIME OF DAY:

SUMMARY:
 NUMBER-HYPOXEMIC EVENTS: 45 EVENTS/24HR RECORDING
 AVG DURATION-HYPOXEMIC EVENTS: 29 SECONDS (RANGE: 5sec-2min)
 MAGNITIDE-HYPOXEMIC EVENTS: *USER CHOSEN-HISTOGRAM FORMAT;
 DATA ARE THE % OF HYPOXEMIC EVENTS IN 3-CATEGORIES: z<4%
 DECREASE FROM BASELINE; 4-10% DECR, >10% DECR*

<4% DECR    4-10% DECR    >10% DECR

SUMMARY: OXYGENATION PROFILE DURING PHYSICAL ACTIVITY:
 % TIME<90% SATURATION (min)
 REST: 3% (5min)
 EXERTION: 90% (240min)
 SLEEP: 20% (59min)
 TOTAL % TIME <90% OF RECORDING TIME: 21% (304min)

CLINICAL REPORT-CUMULATIVE TRENDS AND SUMMARY STATISTICS:

A. SUMMARY STATISTICS: ALL MAJOR CLINICAL VARIABLES FOR THE ENTIRE RECORDING IN THE FORM OF MEAN VALUES +/- STANDARD DEVIATION (SD) OR STANDARD ERROR (SE) OF THE MEAN.

DAY: SUMMARY-CLINICAL VARIABLE:

1
VITAL SIGNS:
RR: 24
BP: 129/85-145/90
HR: 89-140

PHYSICAL ACTIVITY:
ACTIVITY CTS/HR: 1,050±50
STEPS CTS PER HR: 100±22

ENERGY EXPEND:
CALORIES PER HR: 145±12

OXYGENATION:
TOTAL AVG SpO$_2$: 92±9
REST AVG SpO$_2$: 95±1
EXERTION AVG SpO$_2$: 85±2
SLEEP AVG SpO$_2$: 93±5

% TIME<90% SpO$_2$:
10% (144 min)
1% (10min)
50% (120min)
5% (18min)

2
VITAL SIGNS:
RR: 24
BP: 145/90-129/85
HR: 85-145

PHYSICAL ACTIVITY:
ACTIVITY CTS/HR: 905±50
STEPS CTS PER HR: 112±24

ENERGY EXPEND:
CALORIES PER HR: 138±11

OXYGENATION:
TOTAL AVG SpO$_2$: 93±8
REST AVG SpO$_2$: 95±1
EXERTION AVG SpO$_2$: 84±2
SLEEP AVG SpO$_2$: 94±5

% TIME<90% SpO$_2$:
5% (72min)
1% (10min)
45% (115min)
5% (15min)

FIG.5B

B. SUMMARY STATISTICS: COMPARISON OF ONE OR MORE CLINICAL VARIABLES BETWEEN TWO OR MORE SEGMENTS OF A RECORDING IN ONE PATIENT IN THE FOLLOWING FORM:

DAY: OXYGENATION DURING PHYSICAL ACTIVITY (% TIME<90% OXYGEN SATURATION:
REST:          EXERTION:       SLEEP:
1    3%(22min)     50%(120min)     5%(25min)
2    2%(15min)     40%(96min)      1%(5min)

FIG.5C

C. SUMMARY STATISTICS:

| LTOT COMPLIANCE REPORT: | | | |
|---|---|---|---|
| DAY: (8AM->4PM-) | TOTAL COMPLIANCE (min): | OXYGENATION (SpO₂ AVG)-COMPLIANT PERIODS: | OXYGENATION (SpO₂ AVG-DURING NON-COMPLIANT PERIODS: |
| 1 | 7/8=88% | 92% | 85% |
| 2 | 8/8=100% | | ... |
| ... | ... | ... | ... |
| 30 | 5/8=63% | 91% | 80% |
| SUMMARY: COMPLIANCE AVG PER DAY: LOW 63%   HIGH 100% | | | |

FIG.5D

D. SUMMARY STATISTICS: EFFICACY OF AN OXYGEN DELIVERY SYSTEM

| DAY: % TOTAL TIME (min  % TIME (min)<90% SATURATION-DIFFERENT ACTIVITY CATEGORIES: | | | |
|---|---|---|---|
| >90% SATURATION | REST: | EXERTION: | SLEEP: |
| 1-   84% (...min) | 95% (...min) | 40% (...min) | 92% (...min) |
| ... | | | |
| 5-   89% (...min) | 93% (...min) | 60% (...min) | 95% (...min) |

FIG.5E

E. SUMMARY STATISTICS: COMPARISON OF ONE OR MORE CLINICAL VARIABLES AMONG DIFFERENT PATIENTS CAN BE EXPRESSED IN THE FOLLOWING FORMAT:

DAY: PATIENT 1:                                           PATIENT 2:
     TOTAL TIME-HR: OXYGENATION-EXERTION   TOTAL TIME-HR: OXYGENATION-EXERTION
                    (%TIME<90% SATURATION:                (%TIME<90% SATURATION:

1       4           25% (60min)            4              25% (60min)

2       4           50% (120min)           4              50% (120min)

3       4           40% (96min)            4              40% (96min)

| COPD MONITOR: FUNCTIONAL COMPONENTS ||
|---|---|
| PHYSIOLOGICAL PARAMETERS: | FUNCTION EXPLANATION |
| VITAL SIGNS | MONITORING OF HEART RATE, BLOOD PRESSURE, AND RESPIRATORY RATE AT USER-DETERMINED INTERVALS FOR THE LENGTH OF PATIENT RECORDING. |
| OXYGEN SATURATION | MONITORING OF OXYGEN SATURATION BY OXIMETRY AT USER-DETERMINED INTERVALS FOR THE LENGTH OF PATIENT RECORDING. |
| PHYSICAL ACTIVITY & ENERGY EXPENDITURE | MONITORING OF PHYSICAL ACTIVITY IN SEVERAL WAYS, INCLUDING: MEASUREMENT OF THE INTENSITY OF MOVEMENT WITH MULTIPLE ACCELEROMETERS, STEP COUNTING, DISTANCE, WALKING SPEED, AND ENERGY EXPENDITURE AT USER-DETERMINED INTERVALS FOR THE LENGTH OF PATIENT RECORDING. |
| CHEST WALL MUSCLE ELECTROMYOGRAPHIC EMG | MONITORING OF THE CHEST WALL MUSCLE ACTIVATION SIGNAL AT USER-DETERMINED INTERVALS FOR THE LENGTH OF THE PATIENT RECORDING |
| OTHER COMPONENTS: | EXPLANATION |
| AUXILIARY FUNCTIONS | 24-HOUR SYSTEMS CLOCK FOR TIME STAMPING OF ALL EVENTS, INCLUDING CAPABILITY TO ANALYZE THE COMPLETE PATIENT RECORDING OR SELECTED SEGMENTS OF THE RECORDING TO DOCUMENT OXYGEN SATURATION AND/OR THE TYPES OF PHYSICAL ACTIVITY DURING THE CHOSEN INTERVAL; RECORDING CAPABILITY IS UP TO 30-DAYS FOR ALL CAPTURED DATA. |
| LCD DISPLAY | CAN BE SET TO VIEW UP TO FIVE ONGOING DATA CAPTURE FUNCTIONS, INCLUDING OXYGEN SATURATION, SELECTED VITAL SIGNS, INTENSITY OF PHYSICAL ACTIVITY (EITHER ACTIVITY COUNTS, CALCULATED SPEED OF MOVEMENT), CUMULATIVE DISTANCE, OR ENERGY EXPENDITURE PER SELECTED TIME PERIOD. |
| DATA ANALYSIS | SOFTWARE CAPABLE OF A WIDE RANGE OF DATA ANALYSIS FUNCTIONS INCLUDING: TIME TRENDING OF DATA FROM ONE OR ALL SENSORS FOR THE WHOLE RECORDING OR SELECTED TIME INTERVALS OF THE RECORDING; MULTIPLE OPTIONS FOR STATISTICAL DATA ANALYSIS INVOLVING COMPARISONS OF PRIMARY DATA FROM ONE OR ALL SENSORS OVER DIFFERENT SELECTED TIME INTERVALS; DOWNLOADING OF PATIENT RECORDINGS TO A COMPUTER WORKSTATION FOR MORE DETAILED ANALYSIS, INCLUDING COMPARISONS OF KEY VARIABLES AMONG RECORDINGS FROM DIFFERENT PATIENTS, AND FORMATTING OF DATA FOR GENERATION OF CLINICAL REPORTS. |

FIG.6

| CLINICAL APPLICATIONS OF THE COPD MONITOR ||| 
| CLINICAL APPLICATION: | OBJECTIVE: | PATIENT POPULATIONS: |
|---|---|---|
| 1. MONITOR OXYGENATION & PHYSICAL ACTIVITY IN CHRONIC LUNG DISEASE: <br><br> a) MONITOR EFFECTIVENESS OF LTOT PRESCRIPTION <br><br> b) DETERMINE THE NEED FOR LTOT PRESCRIPTION IN AN INDIVIDUAL PATIENT FOLLOWING ACUTE DISEASE EXACERBATION WHEN SUCH AN ASSESSMENT IS CLINICALLY INDICATED <br><br> c) MONITOR COMPLIANCE/ADHERANCE WITH AN LTOT PRESCRIPTION <br><br> d) MONITOR EFFECTIVENESS OF A SPECIFIC OXYGEN DELIVERY SYSTEM <br><br> e) SCREEN FOR TREATABLE HYPOXEMIA IN PATIENTS WITH LESS SEVERE CHRONIC LUNG DISEASE WHO ARE NOT ON LTOT WHEN CLINICALLY INDICATED <br><br> f) MONITOR OXYGENATION & PHYSICAL ACTIVITY IN THE OUTPATIENT SETTING ON INDIVIDUAL PATIENTS AS PART OF CHRONIC DISEASE MANAGEMENT TO DETERMINE A PATIENT-SPECIFIC ACTIVITY/ OXYGENATION PROFILE <br><br> g) MONITOR EFFECTIVENESS OF CHANGES IN DRUG THERAPY IN THE OUTPATIENT SETTING | <br><br> a) ADEQUATE OXYGENATION DURING ALL DAILY ACTIVITIES <br><br> b) ADEQUATE OXYGENATION DURING ALL DAILY ACTIVITIES <br><br><br><br> c) DETERMINE LEVEL OF ADHERENCE TO LTOT PRESCRIPTION AND PROVIDE ADEQUATE OXYGENATION <br><br> d) DETERMINE EFFICACY OF A DELIVERY SYSTEM TO PROVIDE ADEQUATE OXYGENATION DURING DAILY ACTIVITIES. <br><br> e) DETECT TREATABLE HYPOXEMIA AT EARLIER CLINICAL STAGE OF DISEASE-IDEALLY BEFORE SIGNIFICANT END-ORGAN DAMAGE OCCURS <br><br> f) OBTAIN DATA TO MAKE A PATIENT-SPECIFIC RECOMMENDATION FOR ACTIVITY AND LIFESTYLE CHANGE; DEVELOP A PATIENT SPECIFIC ACTIVITY/OXYGENATION PROFILE <br><br> g) OPTIMIZE CURRENT THERAPIES IN OUTPATIENT SETTING | COPD, AND OTHER CHRONIC LUNG DISEASES WHICH ALTER OXYGENATION AND PHYSICAL ACTIVITY, INCLUDING PULMONARY FIBROSIS, SARCOIDOSIS, SICKLE CELL DISEASE, OR ANY OTHER CHRONIC DISEASE WHICH MAY AFFECT THE LUNGS |

FIG.7A

| | | |
|---|---|---|
| h) MONITOR EFFECTIVENESS OF PULMONARY REHABILITATION IN INDIVIDUAL PATIENTS TO ASSESS ON THE ACTIVITY/OXYGENATION PROFILE<br><br>i) MONITOR KEY PARAMETERS (PHYSICAL ACTIVITY, OXYGENATION, EMG, ETC OVER EXTENDED TIME PERIODS THAT CAN INDICATE A CHANGE IN CLINICAL CONDITION OF THE PATIENT | h) OPTIMIZE CURRENT THERAPY FOLLOWING PULMONARY REHABILITATION AND MONITOR THE EFFECTS OF REHABILITAION ON THE ACTIVITY/OXEGENATION PROFILE<br><br>i) DETERMINE CLINICAL STATUS OF PATIENT OVER LONGER TIME INTERVALS-ie. SEVERAL MONTHS-THAT MAY PROVIDE INDICATION OF EXACERBATION OR PROGRESSION OF CHRONIC DISEASE | |
| 2. MONITOR OXYGENATION & PHYSICAL ACTIVITY IN OTHER CHRONIC DISEASES: WITH EFFECTS ON CARDIOVASCULAR SYSTEM | SAME AS ABOVE FOR COPD AND OTHER CHRONIC LUNG DISEASES; DETECT OCCULT HYPOXEMIA; DETECT SIGNIFICANT ALTERATIONS IN DAILY ACTIVITY | CONGESTIVE HEART FAILURE, AND OTHER FORMS OF CHRONIC HEART DISEASE |
| 3. MONITOR PATIENTS WITH SLEEP-RELATED BREATHING DISORDERS | DEVELOP A PATIENT SPECIFIC ACTIVITY/OXYGENATION PROFILE TO BE USED AS PART OF CHRONIC DISEASE MANAGEMENT | PATIENTS WITH OBSTRUCTIVE SLEEP APNEA, AND OTHER SLEEP-RELATED BREATHING DISORDERS |
| 4. TELEMEDICINE MONITORING IN REMOTE AREAS | MONITOR THE EFFECTIVENESS OF CURRENT THERAPY TO OPTIMIZE THE ACTIVITY/ OXYGENATION PROFILE IN PATIENTS WHO CANNOT EASILY TRAVEL OR BE EVALUATED IN THE HOSPITAL OR CLINIC SETTING | PATIENTS IN CATEGORIES #1-3 ABOVE |
| | | |

FIG.7B

SYSTEM AND METHOD FOR OUTPATIENT MANAGEMENT OF CHRONIC DISEASE

FIELD OF THE APPLICATION

The present application relates to the chronic disease management and more particularly to a system and method for chronic disease management.

BACKGROUND

Numbers in square brackets are used herein below as references to endnotes at the end of the description. Patent reference designators appear as standalone numbers or as numbers in parenthesis.

Chronic obstructive pulmonary disease (COPD) is a leading cause of morbidity/mortality in the United States and worldwide [1,2]. The leading cause of COPD is cigarette smoking, although newer data suggest that up to 25% of people with COPD have never smoked a cigarette in their lifetime. The disease typically takes two decades or more to become clinically apparent, producing a series of debilitating symptoms including chronic cough and shortness of breath. The disease is relentless with the development of one or more complications, such as progressive loss of lung function, lung infection, heart failure, or ruptured lung. Recent studies also emphasize a systemic component of the disease manifested as chronic weight loss, skeletal muscle weakness, and osteoporosis that may represent a chronic inflammatory component that contributes to morbidity and mortality [3].

Patients typically progress from having initial mild shortness of breath on exertion and performance of normal activities of daily living to severe shortness of breath in which the patient may require long-term oxygen therapy (LTOT) on a daily basis. The natural history of the disease is one of recurring exacerbations that bring the patient to medical attention with increasing frequency [1,2].

Prevalence/Morbidity/Mortality: Accurate morbidity, mortality and prevalence data suggest a huge and growing disease burden. In 2010, an estimated 24 million individuals in the US were identified with COPD. In addition, based on lung function tests, COPD was estimated to go undiagnosed in 50% of the COPD cohort (12 million). Since COPD is under-diagnosed, this is likely an underestimate of true prevalence. Individuals suffer progressive functional impairment and reduced quality of life as the disease progresses. COPD is the 3rd leading cause of death in the United States. Unlike cardiovascular disease, the prevalence and mortality of COPD worldwide is increasing due to continued exposure to risk factors [2].

Globally, there are an estimated 300 million people with COPD. It is a leading cause of death and disability worldwide. Current estimates indicate that it will be the 3rd leading cause of death worldwide by 2020. Unfortunately, the prevalence of COPD is growing related to the lack of progress with effective smoking cessation in many countries. The COPD burden will remain high for many years to come [4].

Economic/Societal Burden: The financial costs and burden to individual patients and society related to COPD is huge. Disease burden can be quantified in terms of direct costs (healthcare resources needed for direct care) and indirect costs (disability, missed work, premature mortality, and caregiver or family costs from the disease). It is estimated that lung disease costs the United States economy ~$95 billion in direct health-care expenditures each year plus indirect costs of ~$59 billion for an estimated grand total of $154 billion [1]. This cost to society is linked to the chronicity of this disorder. Indirect costs are important since they represent the human capital cost, an important national asset for the economic development of any society. Contrary to popular belief, COPD is not a disease of old people. In fact, it is estimated that approximately 70% of the COPD patients (24 million) in the US are less than 65 years of age, suggesting that many are still in the workforce [4].

In the United States in 2006, there were 16.3 million office outpatient visits, 1.5 million emergency department visits, and 673,000 hospital admissions for COPD [1,5]. Patients with COPD generate between $6,100 and $6,600 annually in excess health care costs, compared with patients without COPD and relative to other medical expenditures in the US. The per capita cost for hospitalization of patients with COPD was 2.7 times the cost for patients without COPD ($5409 vs. $2001). In 2010, total national medical costs secondary to COPD and its complications were ~$32.1 billion with an additional 3.9 billion in absenteeism costs. The latter figure reflects the economic impact of this chronic disease that adds significantly to the overall economic costs of this chronic disease to society [6]. Recent estimates indicate that the cost of COPD to healthcare system in the United States is disproportionately spent on the patients with the most severe impairment.

The disability, suffering, and economic burden of this disease cannot be overemphasized [1,2]. Patients with COPD have a relatively high use of both outpatient and hospital resources. The total societal costs attributable to COPD are projected to increase significantly over the next decade (from $32.1 billion in 2010 to $49 billion) in 2020, suggesting that clinical interventions that result in more effective disease management are greatly needed and can significantly reduce the economic burden to society [6].

SUMMARY

According to one aspect, an outpatient ambulatory patient worn apparatus for managing chronic lung disease includes a plurality of sensors configured to be worn by a patient and to measure a plurality of physiological data. The plurality of sensors includes at least an oximeter, a respiratory rate sensor, and at least one activity or motion sensor. A central monitoring unit (CMU) is communicatively coupled to the plurality of sensors. The CMU includes a computer, and the CMU is worn by the patient in an outpatient setting during activities of daily living. The CMU is programmed to record substantially concurrently a set of time stamped primary data including measurement data from each of the plurality of sensors to a non-volatile memory at a predetermined interval for one or more epochs of time, and to categorize each recorded measurement of each of the plurality of sensors stored in the set of time stamped primary data by a predominate activity type to generate a set of activity type stamped data, the predominate activity type selected from a plurality of activity types including rest, exertion, and sleep. A generate report process runs on the CMU to provide at least one or more reports substantially in real time including at least an indication or determination of whether a chronic lung disease treatment is needed by the patient based on the set of activity type stamped data.

In one embodiment, the generate report process further generates a report or displays a temporal profile of physical activity during rest, exertion, and sleep.

In another embodiment, the generate report process further generates a report or displays a determination of a temporal profile of a duration and magnitude of physical activity during rest, exertion, and sleep, correlated with a temporal profile of oxygenation.

In yet another embodiment, the generate report process further generates a report or displays a determination of a frequency, a duration, and a magnitude of one or more hypoxemic events experienced by the patient.

In yet another embodiment, the generate report process further generates a report or displays a summary of statistics for the plurality of sensors.

In yet another embodiment, the generate report process further generates a report or displays a comparison of one or more variables between two or more segments of a recording made over two or more different epochs of time.

In yet another embodiment, the generate report process further generates a report or displays a summary of statistics for a long term oxygen therapy (LTOT) including an adequacy of a LTOT prescription, or a degree of a patient compliance with an oxygen prescription of the patient during a selected epoch of time.

In yet another embodiment, the generate report process further generates a report or displays a summary of statistics for an adequacy of a patient's LTOT delivery system in the patient, or a report of a summary statistics of a comparison of one or more clinical parameters among different patients.

In yet another embodiment, the CMU is communicatively coupled to an oxygen source or an oxygen delivery unit or to a separate flow meter or adapter flow valve to measure an oxygen flow to the patient.

In yet another embodiment, the CMU regulates an oxygen flow to the patient based on an adequacy of oxygen delivery to the patient.

According to another aspect, an outpatient ambulatory patient worn apparatus for regulation of long-term oxygen therapy (LTOT) delivery includes a plurality of sensors configured to be worn by a patient and to measure a plurality of physiological data. The plurality of sensors includes at least an oximeter, a respiratory rate sensor, and at least one activity or motion sensor. A central monitoring unit (CMU) is communicatively coupled to the plurality of sensors. The CMU includes a computer, and the CMU is worn by the patient in an outpatient setting during activities of daily living. The CMU is programmed to record substantially concurrently a set of time stamped primary data including measurement data from each of the plurality of sensors to a non-volatile memory at a predetermined interval for one or more epochs of time, and to categorize each recorded measurement of each of the plurality of sensors stored in the set of time stamped primary data by a predominate activity type to generate a set of activity type stamped data. A generate report process runs on the CMU to provide at least one or more reports substantially in real time at least a selected one of: an indication or determination of whether a LTOT treatment is needed by the patient, and an indication or determination of a LTOT adequacy of oxygen delivery to the patient, based on the set of activity type stamped data.

In one embodiment, the predominate activity type includes one of a plurality of activity types including rest, exertion, and sleep.

In another embodiment, the CMU is communicatively coupled to an oxygen source or an oxygen delivery unit or to a separate flow meter or adapter flow valve to measure an oxygen flow to the patient.

In yet another embodiment, the CMU regulates an oxygen flow to the patient based on the indication or determination of a LTOT adequacy of oxygen delivery to the patient.

In yet another embodiment, the LTOT apparatus further comprises a flow valve or an adapter flow valve. The CMU regulates an oxygen flow to the patient by control of the flow valve or the adapter flow valve in response to a physical activity of the patient as measured by at least one or more of the plurality of sensors or by a chest wall EMG measurement.

According to yet another aspect, a method for managing chronic lung disease including the steps of: providing a monitor system including: a plurality of sensors configured to be worn by a patient and to measure a plurality of physiological data, the plurality of sensors including at least an oximeter, a respiratory rate sensor, and at least one activity or motion sensor; a central monitoring unit (CMU) communicatively coupled to the plurality of sensors, the CMU including a computer, and the CMU worn by the patient in an outpatient setting during activities of daily living; recording by the computer substantially concurrently a set of time stamped primary data including measurement data from each of the plurality of sensors to a non-volatile memory at a predetermined interval for one or more epochs of time; categorizing each recorded measurement of each of the plurality of sensors stored in the set of time stamped primary data by a predominate activity type to generate a set of activity type stamped data; generating and saving to a non-volatile computer memory one or more reports in one or more graphic or tabular clinical-user defined report formats based on the set of activity type stamped data; and recording or displaying the one or more reports to manage a chronic lung disease.

In one embodiment, the step of providing includes providing a physical activity sensor.

In another embodiment, the step of providing includes providing a movement sensor.

In yet another embodiment, the step of providing includes providing an energy expenditure sensor.

In yet another embodiment, the step of providing includes providing a chest wall muscle EMG sensor.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 4B shows another exemplary COPD monitor system and method clinical report that summarizes the temporal profile of the duration and magnitude of physical activity during rest, exertion, and sleep, excluding the nocturnal hours, correlated with the temporal profile of oxygenation during these categories of physical activity in an individual patient;

FIG. 4F: shows another exemplary COPD monitor system and method clinical report that summarizes the findings related to the frequency, duration, and magnitude of hypoxemic events in an individual patient;

FIG. 5A shows an exemplary COPD monitor system and method tabular report of summary statistics: all major clinical variables for the entire recording in the form of mean values +/−standard deviation (SD) or standard error (SE) of the mean;

FIG. 5B shows an exemplary COPD monitor system and method tabular report of summary statistics in a comparison of one or more clinical parameters between two or more segments of a recording in one patient;

FIG. 5C shows an exemplary COPD monitor system and method tabular report of summary statistics of LTOT compliance with an oxygen prescription in one patient during a chosen measurement period;

FIG. 5D shows an exemplary COPD monitor system and method tabular report of summary statistics for the performance of a specific LTOT delivery system in one patient;

FIG. 5E shows an exemplary COPD monitor system and method tabular report of summary statistics of a comparison of one or more clinical parameters among different patients;

FIG. 6 shows an exemplary table of COPD monitor functional components; and

FIG. 7 shows an exemplary table of clinical applications for the system and method as described herein.

DETAILED DESCRIPTION

Definitions

Figure 1A:
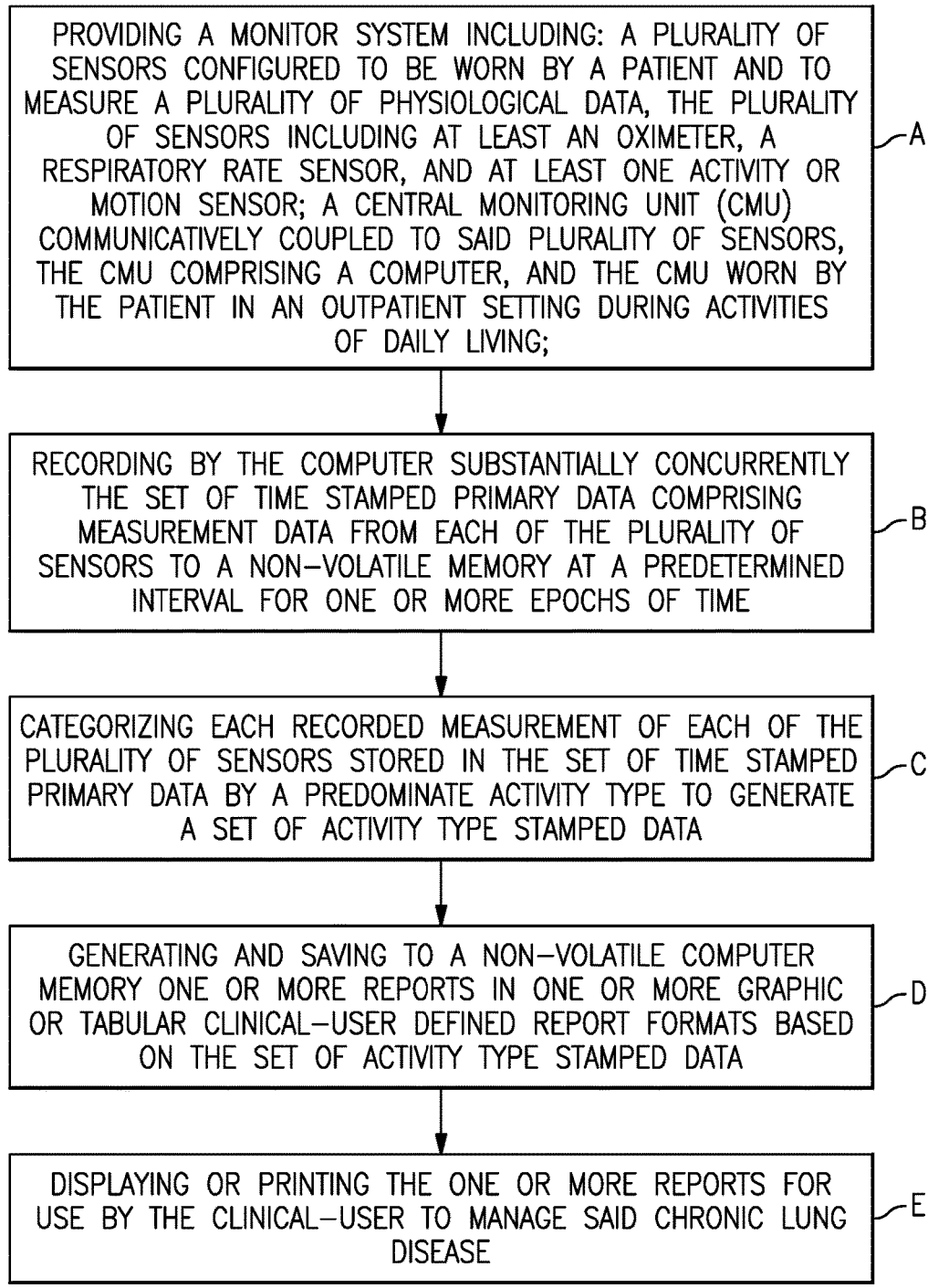
FIG. 1A shows a process block diagram of a new method for managing chronic lung disease.

Measuring human physiological data: measuring human physiological data is defined as including collecting human physiological data, sensing human physiological data, acquiring human physiological data, formatting human physiological data, analyzing human physiological data, and/or storing human physiological data.

Clinical report: a clinical report is defined as the final output or production of the methods and system described herein which represents a summary of the acquisition, analysis, and formatting of the human physiological data obtained during an outpatient recording on a human subject or patient with chronic lung disease or medical equivalent.

Chronic lung disease: or chronic obstructive pulmonary disease (COPD) is a general term for a group of conditions in which there is persistent difficulty in expelling or exhaling air from the lungs; the two most common clinical forms of this disorder: chronic bronchitis and emphysema—can both be present in one individual. These two forms of COPD both share a common etiology: smoking.

Activities of daily living: activities of daily living are defined as all activities engaged in by patients in the outpatient setting; there are three broad categories of activities of daily living, as follows: resting (e.g. sitting quietly), sleeping, or exertion which may range from simple walking to other forms of exertion.

LTOT: long-term oxygen therapy or oxygen supplementation that is delivered to the patient in the outpatient setting while patient engages in activities of daily living.

Flow valve: A flow valve is defined as a valve which controls the flow of oxygen delivery to a patient. Typically, the flow valve is disposed between a source of oxygen (e.g. a portable oxygen tank or a portable oxygen generator) and a tube (e.g. a Nasal cannula) which supplies the controlled flow of oxygen to the patient. A flow valve includes some feature of control, such as, for example, and electrical input configured to set the position of the flow valve (e.g. the rate of oxygen flow in liters per minute). The electrical control means can be analog (e.g. a current or voltage), pseudo digital (e.g. a PWM system) or digital (e.g. digital bits or a digital word via a serial or parallel interface). The electrical control can include a wired or wireless connection (e.g. between a central measuring unit (CMU) and the flow valve). It is unimportant if an optical connection and/or means of control (e.g. fiber optic cable) is used in place of part of the electrical control means. The flow valve also includes a means to mechanically couple to the source of oxygen (e.g. a portable oxygen tank or a portable oxygen generator), which can include a mechanical adapter component (e.g. to mechanically couple to a manual valve or gas flow port on a portable oxygen tank or a portable oxygen generator). In the description herein below, the flow valve is referred to interchangeably as an adapter flow valve.

Time period: Time period is defined as the length of time during which the COPD monitor is in use measuring human physiological data or some subset thereof. Use of the COPD monitor during activities of normal living can be done over minutes, hours, or for an indefinite period of time. During longer time periods of use, data and/or reports can be stored internally by the CMU in a relatively large internal memory or downloaded in part or in full via any suitable wired or wireless means, such as to another computer or computer server. A CMU power source, such as, for example, batteries can be changed and/or recharged as needed.

Time stamped data: Data from a plurality of sensors are acquired and time stamped with the time at which the data was acquired. For example, time stamped data is typically written into memory in the order which it is received for an epoch of time. Such time stamped data can be, for example, saved in memory, e.g. in a file in memory, and presented where each successive record or line of time stamped data includes a time and the readings at that time of a plurality of sensors.

Activity stamped data: Time stamped data can be transformed into activity stamped data. Time stamped data is transformed into activity stamped data by reorganizing the time stamped data typically in memory, or by writing a new set of data to another place (e.g. another location in memory), where each entry of data is now organized by activity type. For example, an analysis process can have as an input data, a set of time stamped data for an epoch of time. The length of the epoch of time, can be, for example, a period of minutes, hours, or days. For example, an epoch of time might be 24 hours. During the epoch of time, at least one set of time stamped data for the plurality of sensors (and optionally an EMG sensor) will be recorded in any suitable non-volatile memory. The time stamped data from any epoch of time can be analyzed by a process running on any suitable processor (e.g. of a CMU) so that the time stamped data of the epoch of time is analyzed over any suitable subintervals of the epoch of time (e.g. at the acquisition rate or some multiple of the acquisition rate) to determine an activity type of each entry, line, or record of time stamped data, or of groups of entries, lines, or records of time stamped data. Once each entry, line, or record of time stamped data is so labeled (e.g. by the process running on the processor, adding, editing, or filling in, an activity field to each entry, line, or record of time stamped data (either individually, or as groups of data), the entire set of data for that epoch of time is then reorganized or re-written as sorted by the activity type of each record. The resultant transformed activity data will have as many categories as the number of activities being determined. Typically, the transformed data will be organized by periods of rest, exertion, and sleep. There will generally be groups of transformed activity type entries, lines, or records which happen to fall in groups of time as is typical of periods of patient activities. For example, a patient walking a distance would might have a series of successive time stamped data organized under the activity type exertion. Or, a restless patient might have several periods of intermingled sleep and rest during the night-time period. In some aspects of the new apparatus, there can be presentations of activity stamped data with time. However, in a most general application, it is only important that an analysis and/or report process receive the activity type data, where, for example, a percentage of the epoch of the different activity types or predominant activity types can be more important than at what time or over what time period the activity type actually occurred.

Generate report process: A generate report process typically formats and presents in any suitable form or media a report which is based at least in part on the activity stamped data. Typically, the report can be saved to a file in non-volatile memory as, for example tabular data, one or more graphs or curves, or any combination thereof. The report generate process can include analysis, such as, for example, notations or marks where data falls below or above a predetermined threshold or falls within or outside of a predetermined numerical window. The report can also typically be printed and/or displayed, such as on any suitable computer device (e.g. any suitable personal computer, laptop computer, tablet computer, etc.) which can receive data by any suitable wired or wireless means from the patient worn apparatus.

Regulation of LTOT delivery: Regulation of LTOT delivery can include monitoring patients for the determination of the need for LTOT, the determination of the adequacy of prescribed LTOT; and a patient's compliance with an LTOT prescription.

Compliance: Compliance as used hereinbelow includes a patient's adherence to a prescribed oxygen therapy (e.g. use of a portable supplementary oxygen source during activities of daily living). In some embodiments, the apparatus described hereinbelow can determine the temporal profile of use of an oxygen delivery system which can provide an assessment, for example, of LTOT therapy compliance and adherence to the LTOT prescription by the patient. Oxygen therapy compliance can be monitored for both efficiency (e.g. is the patient receiving sufficient supplementary oxygen deliver during the patient's activities of daily living). Equally important, in some embodiments, the apparatus described herein can determine if the patient is actually using the prescribed supplementary oxygen source. For example, patients might actually, otherwise unknown to the prescribing professional, be not using the supplementary oxygen apparatus because of, for example, a lack of appropriate provider-patient interaction to address LTOT compliance, prescription of oxygen delivery systems which are not appropriate (e.g. the supplementary oxygen source is too heavy or cumbersome), and other social barriers, including unwillingness to appear in public related to social stigma or increased vulnerability [9,24]. Suboptimal patient compliance has been linked to increased morbidity and mortality [1,17]

Hypoxemic event: A hypoxemic event is defined as a decrease in oxygen saturation (or the amount of dissolved oxygen in the blood) as measured for example by an oximetry sensor that is greater than about 4% from the baseline value, or a decrease in oxygen saturation below or about 90% saturation. In addition, the magnitude of the hypoxemic event can be classified as either mild, moderate, or severe based on a user chosen format.

Dyspnea: or breathlessness which is the nonmedical equivalent of dyspnea which is the symptom of shortness of breath that is the defining symptom that most commonly is a major clinical characteristic of patients with chronic lung disease.

Chest wall muscle EMG: or chest wall (parasternal) muscle electromyographic activity is a physiological signal which is acquired by suitable sensors that is a surrogate for neural output from the brain respiratory center [7]. This signal represents one of the earliest measured signals from the central nervous system to the muscles involved in respiration that corresponds to the perception of breathlessness in human subjects during exertion. The magnitude of this signal is linked to the level of exertion of the human subject such that an increased use of the respiratory muscles is correlated with an increase in this signal.

A new system and method for monitoring a plurality of clinical parameters in the outpatient setting (e.g. during normal outpatient activity) for the management of patients with chronic lung disease is described herein below. In one embodiment, the system and method can be used for an analysis of data obtained from monitored patients while they are engaged in normal daily activities. The system typically includes sensors appropriately positioned on the human body that can provide a continuous collection of physiological data over extended recording periods (e.g. 1-5 days). These physiological data represent the indicators of the key clinical parameters that are critical to chronic lung disease management. A central monitoring unit (CMU) receives and stores the physiological data from each sensor. In some embodiments, the CMU can transmit signals to other components based on analysis of the physiological data from one or more of the sensors. A data analysis process (computer program or "software") includes a data analysis capability (one or more process algorithms) that can assess and analyze the raw data and generate summary reports using user-defined formats. Such reports can be used for modification of the treatment plan of patients with chronic lung disease, usually as clinically indicated by the measured physiological data. In some embodiments, there can also be sensors which include, but are not limited to monitoring of: heart rate, blood pressure, respiration, oxygen saturation, physical activity measured with multiple accelerometers and a pedometer, and energy expenditure. The CMU is worn by the patient and typically has a footprint or size that will produce little or no interference with daily physical activity. The CMU includes means to analyze the data coming from the sensors as well as other components, and to send appropriate signals to other components to carry out specific tasks.

FIG. 1A shows a process block diagram of a new method for managing chronic lung disease including the steps of: A) providing a monitor system including: a plurality of sensors configured to be worn by a patient and to measure a plurality of physiological data, the plurality of sensors including at least an oximeter, a respiratory rate sensor, and at least one activity or motion sensor; a central monitoring unit (CMU) communicatively coupled to the plurality of sensors, the CMU including a computer, and the CMU worn by the patient in an outpatient setting during activities of daily living; B) recording by the computer substantially concurrently the set of time stamped primary data including measurement data from each of the plurality of sensors to a non-volatile memory at a predetermined interval for one or more epochs of time; C) categorizing each recorded measurement of each of the plurality of sensors stored in the set of time stamped primary data by a predominate activity type to generate a set of activity type stamped data; D) generating and saving to a non-volatile computer memory one or more reports in one or more graphic or tabular clinical-user defined report formats based on the set of activity type stamped data; and E) displaying or printing the one or more reports for use by the clinical-user to manage the chronic lung disease.

Figure 1B:
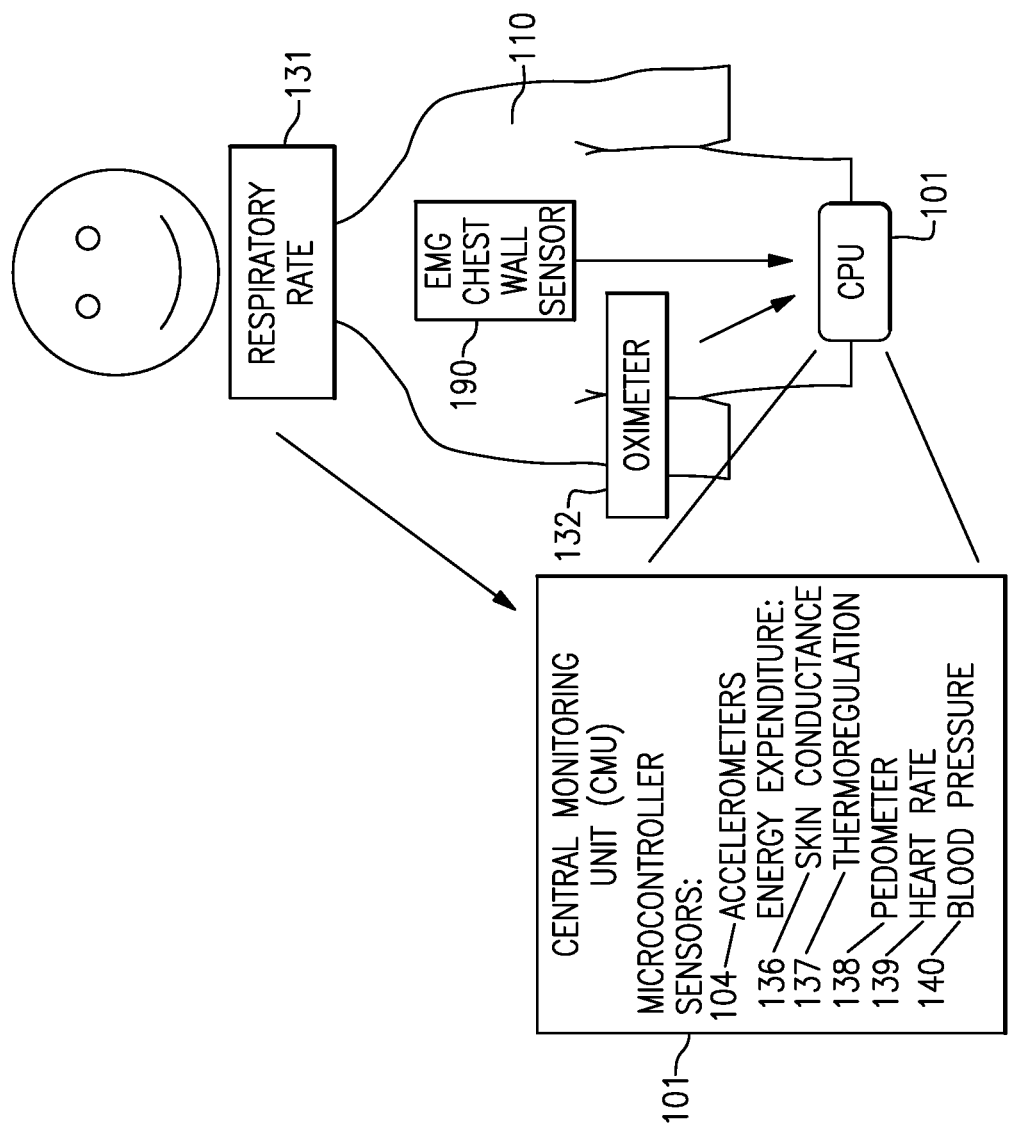
FIG. 1B shows a block diagram of an exemplary system suitable to perform the new method of FIG. 1A.

FIG. 1B shows a block diagram of an exemplary system suitable to perform the new method of FIG. 1A. A monitor system to be worn by a person 110 in the normal activities of daily living includes a plurality of sensors configured to be worn by a patient and to measure a plurality of physiological data. The plurality of sensors includes at least an oximeter 132, a respiratory rate sensor 131, and at least one activity or motion sensor (e.g. one or more accelerometers 104, a skin conductance sensor 136, a thermoregulation sensor 137, a pedometer 138, a heart rate sensor 139, a blood pressure sensor 140, and/or an EMG chest wall sensor 190. A central monitoring unit (CMU) 101 is communicatively coupled to the plurality of sensors. CMU 101 includes a microcontroller or any other suitable computing device.

In some embodiments, an adapter unit can be coupled with a solenoid flow valve that is interposed between the patient and his/her oxygen source or oxygen delivery unit when the patient is receiving oxygen supplementation. This adapter unit and valve typically includes a means to sense the presence of an oxygen delivery system and initiate a change in oxygen delivery (oxygen flow) as controlled by the CMU in response to one or more physiological measurements. A data analysis process formats the data from the sensors, typically in a time stamped manner. The process typically includes several functions, including the ability to monitor the temporal profile of changes in monitored clinical parameters on a continual basis. In some embodiments, the CMU marks specific events or time intervals of the recording. In some embodiments, the capability to measure the number, duration, and magnitude of clinical parameters in the whole recording or chosen time intervals of the recording, and to perform statistical analysis on these data, as specified by the user of the program. The process typically includes multiple choices for graphical or text display of the data as final summary reports in user-defined formats.

The system and method described herein comprises a means for acquiring, analyzing, and processing physiological data on human subjects in the outpatient setting that can then be utilized for medical decisions by a medical provider as part of a chronic lung disease (or medical equivalent) management program. The system and method with accompanying hardware components and data processing capability is designed specifically for use by medical professionals as a tool to facilitate disease management. The system and method is designed to fill a gap in the standard approach to chronic lung disease in which patients are rarely assessed in the outpatient setting. Management remains a passive process largely confined to the outpatient setting where patients and providers interact. More often than not disease exacerbations bring patients to medical attention with subsequent hospitalizations. The present application fulfills a long felt need to be able to effectively monitor, manage, and identify patients in the outpatient setting before they need hospitalization so that a disease management intervention can be initiated to avoid hospitalization. This new system and method is designed to function as a proactive approach in which the clinical status of a patient can be assessed on a regular basis as needed at the judgment of the medical provider. The acquisition, analysis, and formatting of data collected in the outpatient setting provides medical providers with information to change management before a serious clinical deterioration occurs.

This approach is a new paradigm for management of chronic lung disease that is not part of current standard medical practice. The clinical and functional status of a patient can be monitored in real time using parameters that are recognized as important for the long-term outcome of patients with chronic lung disease. This type of proactive assessment and management is only possible with a system and method that can accurately acquire and format relevant data for use by medical providers.

Figure 1C:
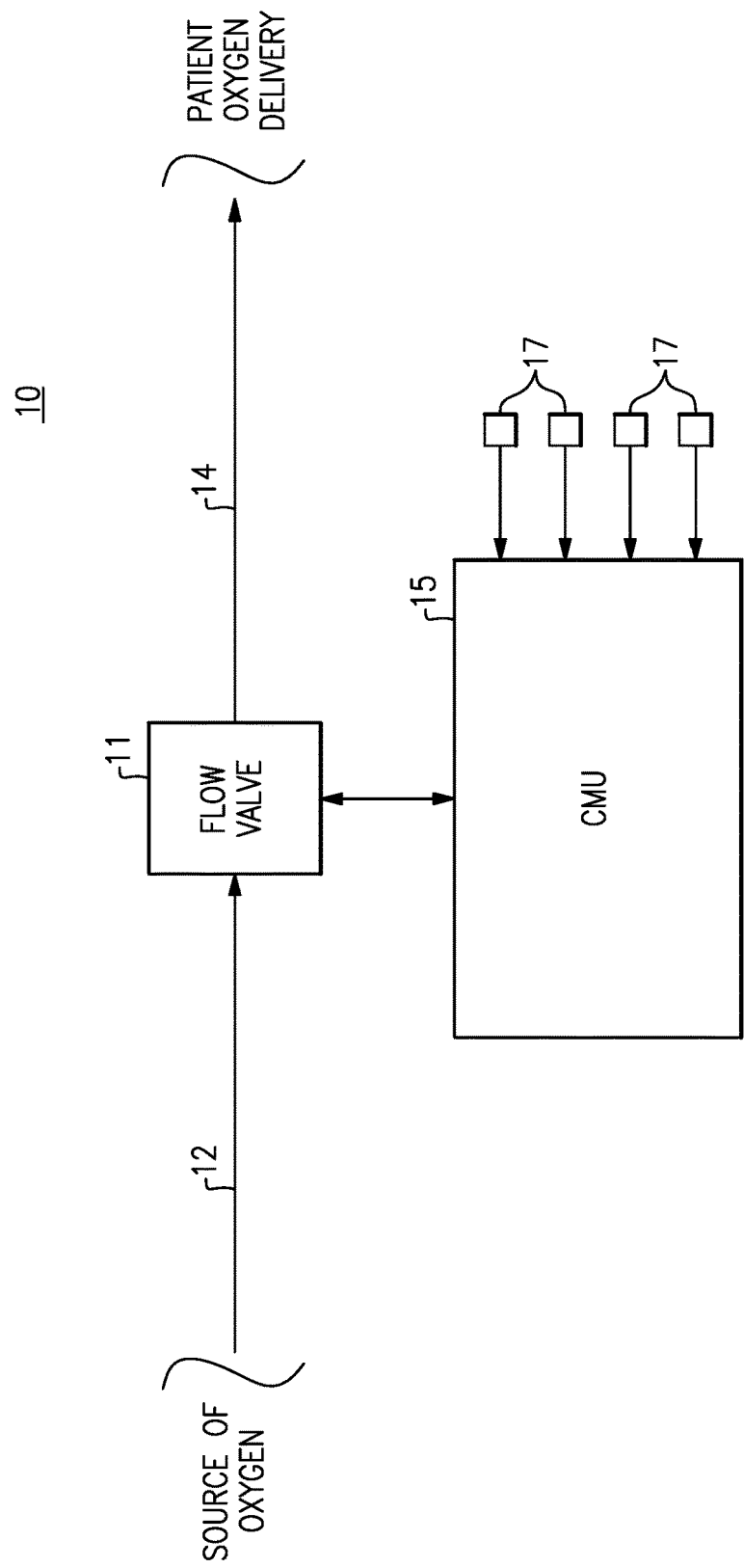
FIG. 1C shows a block diagram of another exemplary COPD monitor.

FIG. 1C shows another embodiment of the system and method for the new approach to monitoring. CMU 15 is communicatively coupled to a plurality of physiological sensors 17. According to this aspect of a chronic disease monitor, it was realized that data beyond that normally considered can be useful in the management of chronic disease, such as chronic lung disease. The new physiological parameters include a movement sensor, an energy expenditure sensor and/or and a chest wall muscle electromyographic signal (chest wall muscle EMG).

It was also realized that calculating the predominate activity type selected from the group consisting of rest, exercise, and sleep over an epoch of time provides a new metric of physiological data for outpatient chronic disease management. It was realized that another new metric that calculates the percentage of time that a measured oxygen saturation is below an oxygen saturation threshold value for each of the activities for each epoch of time is also helpful for the management of chronic disease, particularly the management of chronic lung disease.

Figure 1D:
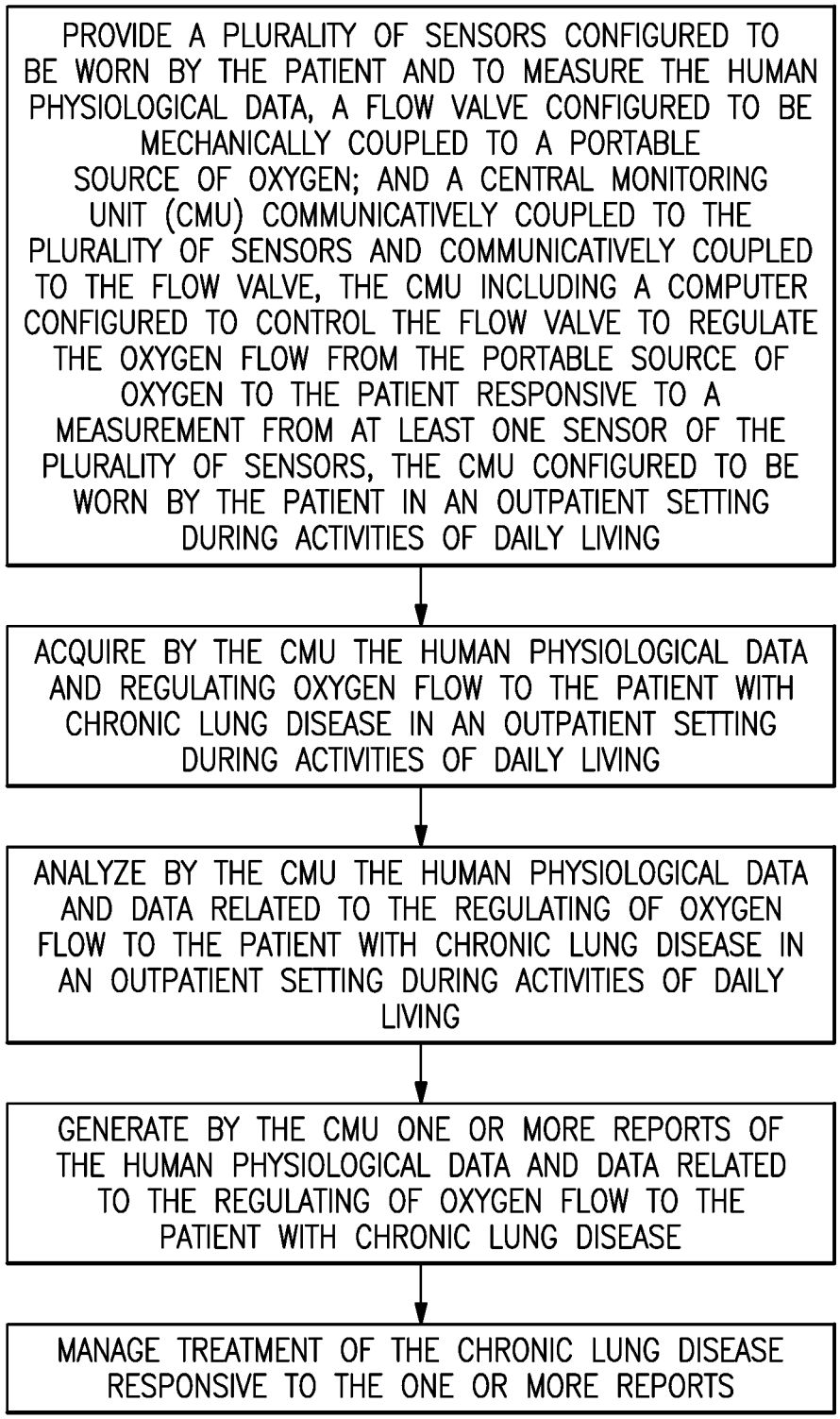
FIG. 1D shows another method for measuring human physiological data and regulating oxygen flow to a patient with chronic lung disease.

FIG. 1D shows another process block diagram of one embodiment of the method using system such as a CMU based system of FIG. 1C. The monitor system includes a plurality of sensors configured to be worn by said patient and to measure a plurality of physiological data (e.g. the system of FIG. 1C). The plurality of sensors (e.g. sensors 17, FIG. 1C) include at least an oximeter, a respiratory rate sensor, in combination with at least one of the new sensors for the outpatient management of chronic lung disease, a movement sensor, an energy expenditure sensor and/or and a chest wall muscle electromyographic signal (chest wall muscle EMG). The central monitoring unit (e.g. CMU 15, FIG. 1C) is communicatively coupled to the plurality of sensors. The CMU includes a computer configured to record data from the plurality of sensors. The CMU is configured to be worn by said patient in an outpatient setting during activities of daily living. The CMU records data from said plurality of sensors to a non-volatile memory. The data includes an oxygen saturation and a physical activity based on one or more of the movement sensor, the energy expenditure sensor and/or and the chest wall muscle EMG sensor at a predetermined interval for one or more epochs of time. For each epoch of time, the predominate activity type is calculated as rest, exercise, and sleep. Also, for each epoch of time a percentage of time that the oxygen saturation is below an oxygen saturation threshold value is calculated. A graph is generated which includes a plot of oxygen saturation and activity versus time. A report is also generated which includes the percentage of time that said oxygen saturation fell below said oxygen saturation threshold value for each of said activity types. Both the graph and the report of the percentage of time that the oxygen saturation fell below said oxygen saturation threshold value for each of said activity types is reported as output data which are typically displayed on any suitable display or printed by any suitable printing device.

Figure 1E:
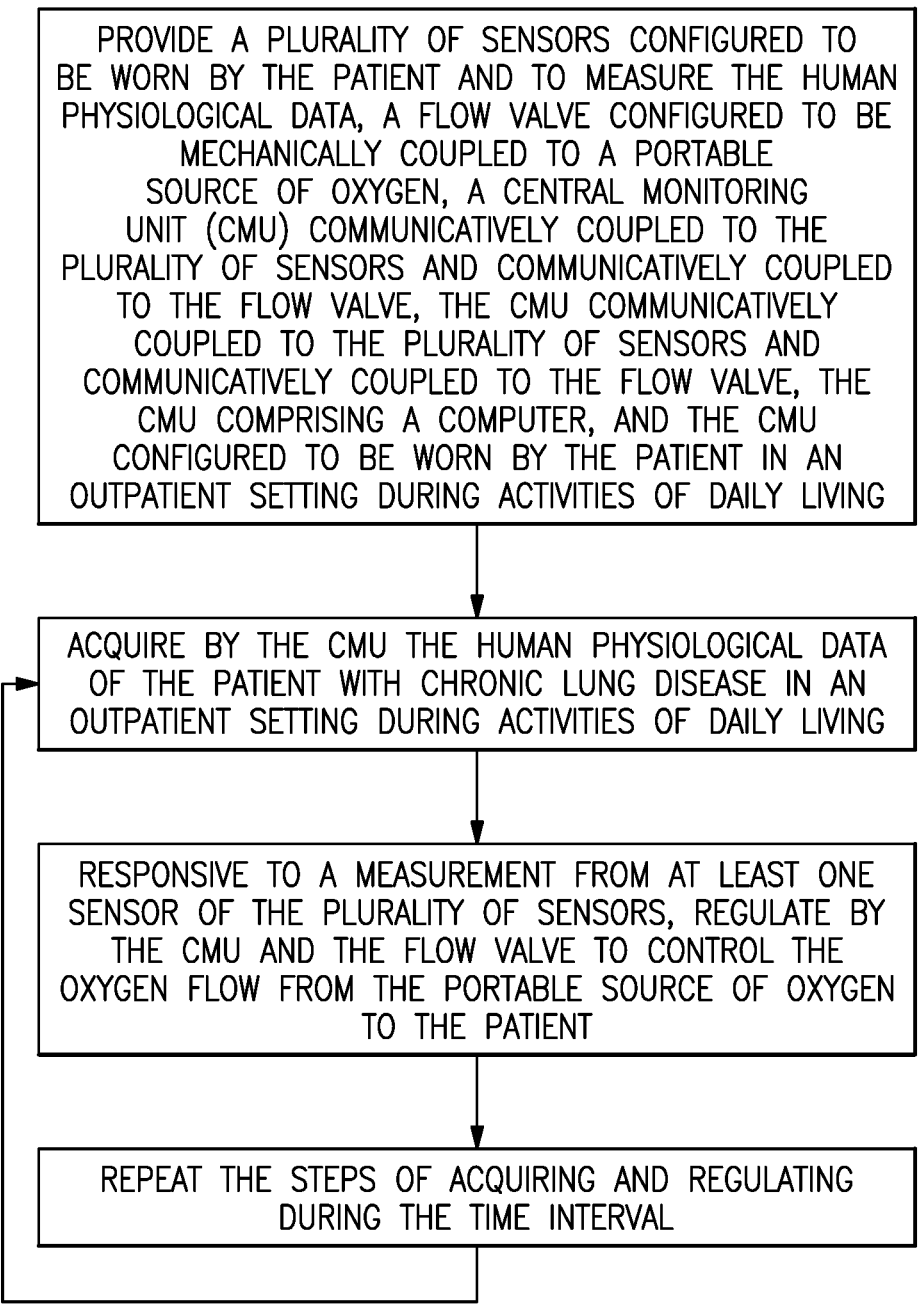
FIG. 1E shows another method for measuring human physiological data and regulating oxygen flow to a patient with chronic lung disease for a time interval.
Figure 1F:
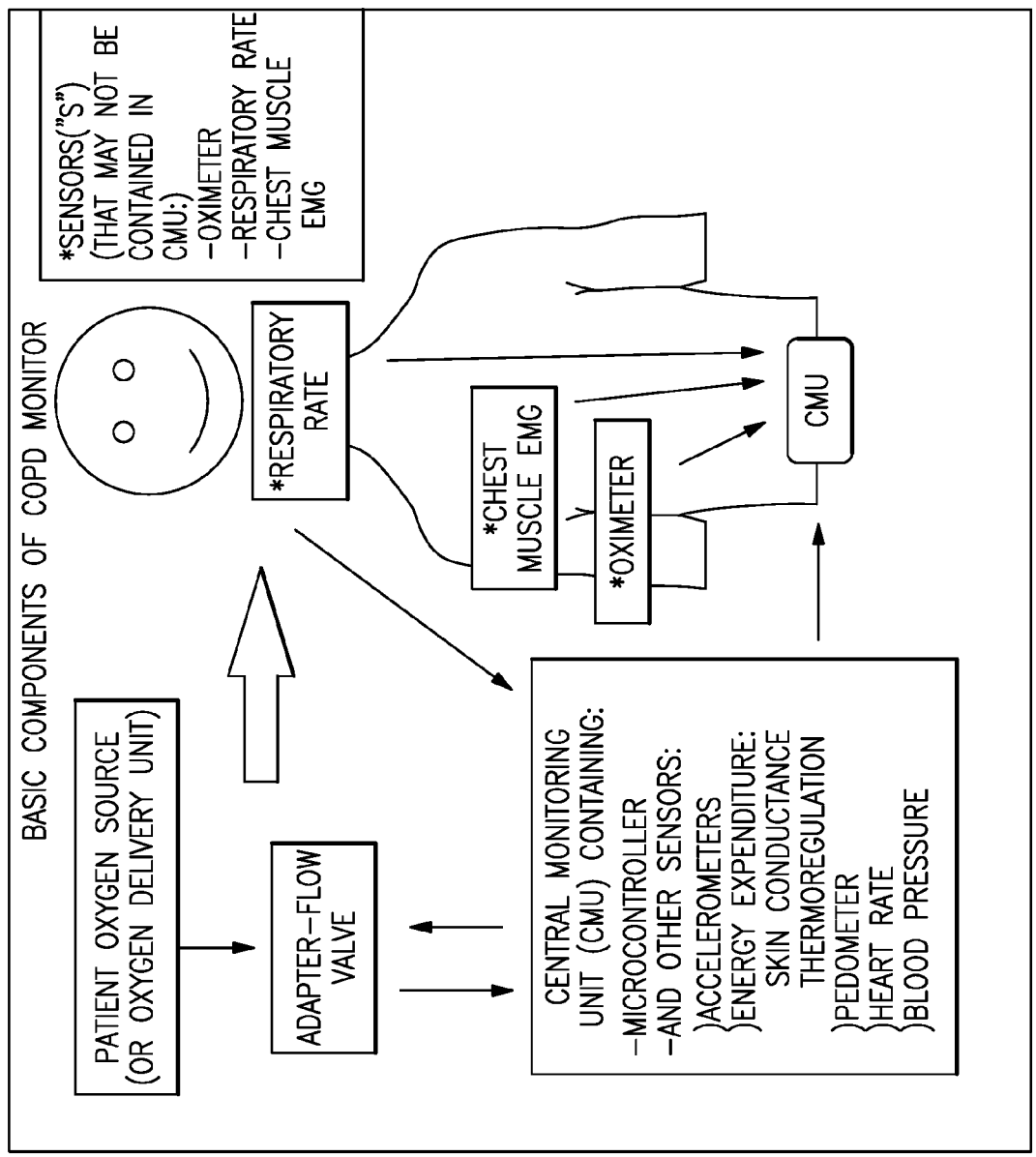
FIG. 1F shows a block diagram of the basic components of another exemplary embodiment of a COPD Monitor.
Figure 1G:
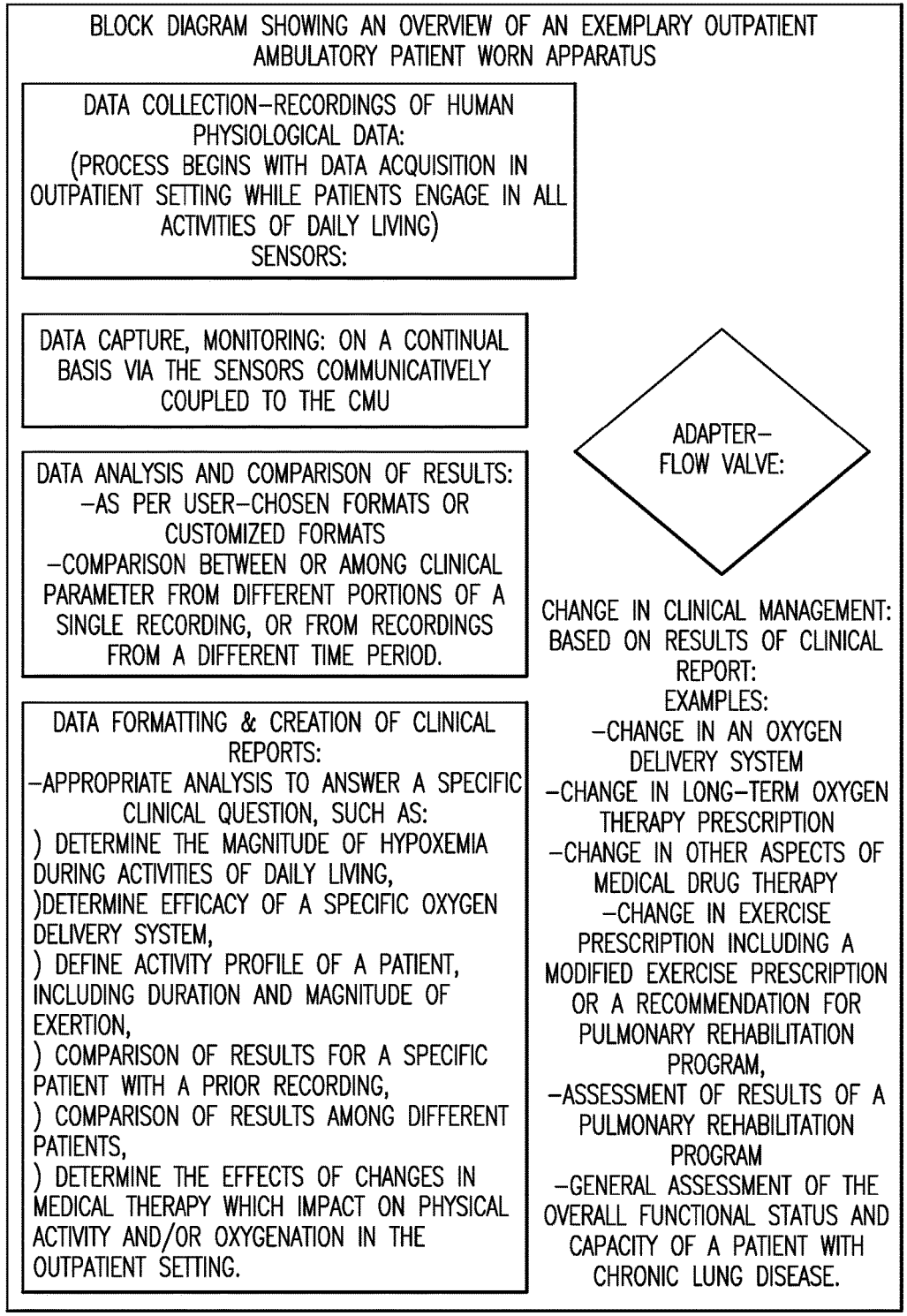
FIG. 1G shows a block diagram of an exemplary scheme of operation for an outpatient ambulatory patient worn apparatus.

FIG. 1E and FIG. 1F show other embodiments of a system where one or more of the new sensors for the outpatient management of chronic disease, while still available for data collection according to the new method, now also provide a sensor control function which in combination with a flow valve controls the flow of oxygen to a patient in an outpatient setting based on one or more of the movement sensor, the energy expenditure sensor and/or and the chest wall muscle EMG sensor. One or more of the oximeter and/or the respiratory rate sensor can also be used to supplement the active control of oxygen for a person wearing the system while involved in the normal activities of living in an outpatient context.

FIG. 1E shows an embodiment of a body worn system where the primary sensor used to control the flow of oxygen to the patient form a source of oxygen via flow valve 11 includes at least one of a movement sensor or an energy 17a or an expenditure sensor 17b.

FIG. 1F shows an embodiment of a body worn system where the primary sensor used to control the flow of oxygen to the patient form a source of oxygen via flow valve 11 includes at least the chest wall muscle EMG sensor 17c.

There are several embodiments of the method and system described herein that exemplify this proactive approach to disease management. These embodiments are discussed in greater detail later, but are briefly outlined here for better understanding of scope and rationale for the new system and method for outpatient management of chronic disease. Both embodiments generate data that can play an important role in the management of patients with chronic lung disease by medical providers.

First, increased "breathlessness" (shortness of breath or dyspnea) is a universal manifestation of a decompensated patient with chronic lung disease. If this breathlessness is sustained, changes in other physiological markers, including an increase in respiratory rate or a decrease in blood oxygen content (oxygen saturation) will follow. A marker of breathlessness that precedes this clinical deterioration is an increased activation of the chest wall muscles involved in breathing, or chest wall muscle electromyographic signal (e.g. chest wall muscle EMG) [7]. This physiological signal correlates with breathlessness and reflects the magnitude of the effort expended by a patient as they enter a period of exertion. This signal will be utilized either alone or in combination with other physiological parameters for patient assessment and monitoring the level of exertion in the outpatient setting during activities of daily living, or as part of the algorithm that regulates oxygen flow to a patient with chronic lung disease.

Second, the level of physical activity correlates with the clinical outcome of patients with chronic lung disease better than primary measurements of lung function. Therefore, another embodiment will utilize physiological data acquired in the outpatient setting that characterizes the duration and magnitude of exertion and energy expenditure during daily living either alone or in combination with other physiological parameters for patient assessment, or specifically as a part of the algorithm that regulates oxygen flow to a patient with chronic lung disease.

There are several advantages of using the parameters of physical activity and/or chest wall muscle EMG for patient assessment and to regulate oxygen flow. First, these parameters are linked to patient clinical status and clinical outcomes of patients with chronic lung disease. Second, use of these parameters can provide more precise control over oxygen saturation in an individual patient can be obtained, compared to use of oxygen saturation alone. This is because changes in physical activity and/or chest wall muscle EMG that accompany exertion precede changes in oxygen saturation.

FIG. 1C shows a block diagram of an exemplary COPD monitor 10. A system for acquiring, storing, analyzing, and formatting human physiological data and regulating oxygen flow to a patient with chronic lung disease, includes a plurality of sensors 17 configured to be worn by the patient (not shown in FIG. 1C) and to measure the human physiological data. A flow valve 11 is configured to be mechanically coupled (e.g. gas flow pipe 12) to a portable source of oxygen (not shown in FIG. 1C). A central monitoring unit (CMU) 15 is communicatively coupled to the plurality of sensors 17 and communicatively coupled to the flow valve 11. The CMU 15 includes a computer which is configured to control the adapter/flow valve 11 to regulate the oxygen flow from the portable source of oxygen to the patient responsive to a measurement from at least one sensor of the plurality of sensors 17. The CMU 15 is configured to be worn by the patient in an outpatient setting during activities of daily living. The one-way arrows between the CMU 15 and the plurality of sensors 17 indicate that a measurement of one or more human physiological parameters is conveyed from one or more sensors 17 to the CMU 15. In some embodiments, one or more sensors can be two-way communicatively coupled to a CMU, such as, for example, for the CMU to configure a sensor. Similarly, there can be one-way connectivity between a CMU and a flow valve where the CMU sets the position of the flow valve (e.g. from closed or nearly closed to open). Or, a "smart" flow valve might have two-way connectivity with a CMU and return information, such as, for example, its current operating position (e.g. open half way). As discussed in more detail herein below, sensors 17 can be located inside of a CMU housing or elsewhere on a patient (i.e. not within the CMU housing).

The system will can include: 1) a means for patient input during the recording that can be used to time-stamp events (e.g. a physiological event of significance to the patient) or specific time periods of the recording; these time-stamped events will then be available or "visible" to the user during data analysis; 2) a means to download data from the CMU either thru conventional phone lines or other wireless formats (infrared or ratio frequency transmission) to a remote computer base station; 3) a means to interface with a patient's oxygen source or delivery unit to detect and quantify the use of this system; and 4) a means for initiating a change in oxygen delivery (liter flow per minute), based on an assessment of the magnitude of change in one or more measured parameters from user-defined baseline target values of these same parameters.

FIG. 1D shows the basic components of a method for measuring human physiological data and regulating oxygen flow to a patient with chronic lung disease including the steps of: 1) provide a plurality of sensors configured to be worn by the patient and to measure the human physiological data; these sensors are positioned on the patient's body in a fashion designed to not interfere with the performance of normal activities of daily living; several sensors are housed within a central monitoring unit (CMU) positioned at the waist inside a central housing unit, while the respiratory rate, chest wall muscle EMG, and oximetry sensors are located near the nose/mouth, chest wall, or upper limb, respectively, in the figure in a preferred embodiment; 2) a adapter/flow valve configured to be mechanically coupled to a portable source of oxygen or oxygen delivery unit; and 3) a central monitoring unit (CMU) communicatively coupled to the plurality of sensors and communicatively coupled to the adapter/flow valve, 4) the CMU including a computer configured to control the adapter/flow valve to regulate the oxygen flow from the portable source of oxygen or delivery system to the patient responsive to a measurement from at least one sensor of the plurality of sensors, 5) the CMU configured to be worn by the patient in an outpatient setting during activities of daily living; 6) the CMU performing the functions of; a) acquisition and storage of the human physiological data from all the sensors continuously, including the data pertaining to the regulation of oxygen flow to the patient with chronic lung disease during activities of daily living; b) analysis of these data from all the sensors; c) formatting of all these data and generation of one or more reports of the human physiological data, including the data related to the regulation of oxygen flow to the patient, according to user-specified criteria or user-chosen formats for data analysis. These reports can be employed by the user, typically a medical professional, in the management of chronic lung disease.

FIG. 1E shows a method for measuring human physiological data and regulating oxygen flow to a patient with chronic lung disease for a specified time interval comprising the steps of: 1) provide a plurality of sensors configured to be worn by the patient and to acquire the human physiological data obtained while patient engages in normal activities of daily living, and an adapter/flow valve configured to be mechanically coupled to a portable source of oxygen or oxygen delivery unit, 2) a central monitoring unit (CMU) communicatively coupled to the plurality of sensors and communicatively coupled to the adapter/flow valve, 3) the CMU comprising a computer, and 4) the CMU configured to be worn by the patient in an outpatient setting during activities of daily living and the acquisition by the CMU of the human physiological data of the patient with chronic lung disease in an outpatient setting during activities of daily living; and 5) responsive to a measurement from at least one sensor of the plurality of sensors, the CMU regulates the operation of the adapter/flow valve to control the oxygen flow from the portable source of oxygen or oxygen delivery unit to the patient; and 7) repeating the steps of acquiring human physiological data from the plurality of sensors on a continuous basis, including regulating the flow valve controlling oxygen delivery to the patient using the data obtained from one or more sensors during the said time interval.

COPD Monitor, LTOT System and Method: The system and method described herein ("COPD Monitor") is designed for long-term management of chronic lung disease. In one exemplary embodiment, the system includes the components described herein below.

A plurality of sensor devices can monitor physiological signals and capture these signals ("data") on a continual basis. These signals represent a plurality of different clinical parameters that are monitored in patients over selected time intervals for the purpose of gathering data to be used in chronic lung disease management or the medical equivalent.

A central monitoring unit (CMU) that contains a microprocessor (e.g. a microcontroller) for acquiring, analyzing, and formatting the raw data from the sensors, and transmitting signals based on the raw data to other components of the system. In some embodiments, the CMU can also contain sensors and/or part of sensor assemblies as described herein below.

An adapter unit and flow valve connected either physically or wirelessly in a circuit with the patients' oxygen source or delivery unit that receives signals from the CMU to change the liter flow of oxygen to the patient typically on an ongoing continuous basis.

A data analysis process ("software") or computer program typically located in the CMU that can perform a plurality of analysis functions, including the formatting of collected raw data for the creation of clinical reports on chosen clinical parameters following transfer to a computer workstation at a remote location.

Additional components can include the capability to run the system on a rechargeable battery, an indicator light/screen (LED) on the front face of the central housing unit showing running time, clock function, the output of selected sensors, and an indicator of whether a patient is connected to an oxygen source or delivery device.

FIG. 1F shows a block diagram of the basic components of one exemplary embodiment of a COPD Monitor 100 according to the application. The exemplary COPD monitor 100 includes 1) various physiological sensors positioned on the patient's body in a fashion designed to not interfere with the performance of daily activities; several sensors are housed within the CMU 101, a wearable unit, typically positioned at the waist, while the respiratory rate measurement 131 and oximetry sensor measurement 132 can be located as noted near the nose/mouth or upper limb, respectively; 2) the CMU 101 is connected (directly or in wireless mode) to each sensor (e.g. wired and/or wireless sensors) to accomplish the functions of data display, analysis, data capture and storage; 3) the adapter/flow valve unit 107 functions to regulate oxygen liter-flow coming from a patient oxygen source or delivery device 106, such as, for example, by use of a PID feedback loop algorithm involving the CMU 101. In some embodiments, the CMU 101 can use one or more of the parameters measured by the sensors to regulate oxygen flow to a patient on LTOT; 4) the adapter and flow valve 107 function under the control of the CMU to modify oxygen delivery (arrow 108) to the patient 110. FIG. 1F shows but one possible embodiment for the position of each sensor and the CMU.

Exemplary sensors which can be housed in the CMU 101 housing include one or more accelerometers for measurement of physical activity 104, energy expenditure sensors, such as skin conductance 136 (which can include one or more remote skin mounted sensors), thermoregulation 137 (which can also include one or more remote temperature sensors), pedometer 138 (a pedometer function can also be derived from accelerometer data), heart rate sensor 139 (which can include one more body mounted sensors), and blood pressure 140, (which can also include one or more body mounted sensors), and chest wall muscle electromyographic (EMG) sensors 190 (which also can include one or more body mounted sensors). Sensors are communicatively coupled to the CMU 101 housing via any suitable wired or wireless means.

Continuing with FIG. 1F, the narrow arrows show exemplary functionality of a oxygen closed loop oxygen flow closed loop process control. In the exemplary embodiment of FIG. 1F, oxygen is sourced from a patient oxygen source or delivery device 106 via adapter-flow valve 107 to patient 110 as indicated by wider arrow 108 (oxygen gas flow) as part of LTOT therapy. A digital closed loop runs as a computer process on a microcomputer located within the CMU 101 housing. The feedback sensor information can include, for example, information (e.g. wired or wireless digital and/or analog signals) from the accelerometer physical activity sensors 104, the respiratory rate sensor 131 (arrow 123), the chest wall EMG sensor 190 and/or the oximeter for measurement of oxygen saturation 132 (arrow 124). As described herein in more detail, one or more other sensors can also add feedback data to be computed in meeting the set point target values of measured parameters, typically a desired respiratory functional level, as indicated by one or more of the sensor measurements.

In this latter embodiment, one or more of the sensor measurements other than the measurement of oxygen saturation by the oximeter serve as primary determinants of the final signal generated by the CMU that is used to regulate oxygen flow to the patient via a PID closed loop algorithm. Typically, the sensor measurements that would be included in this embodiment would be measurements of the parameters of physical activity and/or chest wall muscle EMG. Inclusion of other parameters in this latter embodiment are not excluded by this example. In this embodiment, the oximeter sensor data serves only as a reference target value and is not part of the active input to the computer process algorithm that generates the signal leading to a change in oxygen flow to the patient.

During closed loop operation, the oxygen needed by the patient to satisfy the desired respiratory functional level is automatically controlled by the CMU control of the flow valve setting (arrow 122). In other words, the closed loop operates to automatically (i.e. automatic control) supply a level of oxygen flow (arrow 108) to patient 110, which maintains the desired patient respiratory functional level as measured by the respiratory rate 131, chest wall EMG, oximeter 132, and/or any other sensor functions that are selected as active inputs into the feedback signal for the operation of the control loop. The control loop is typically implemented as a proportional, integral, derivative (PID) loop controller, however any other suitable control loop techniques can be used. The current setting of the adapter-flow valve 107 can also be reported back to the CMU, typically by a wired or wireless analog and/or digital connection, as shown by arrow 121.

Figure 2:
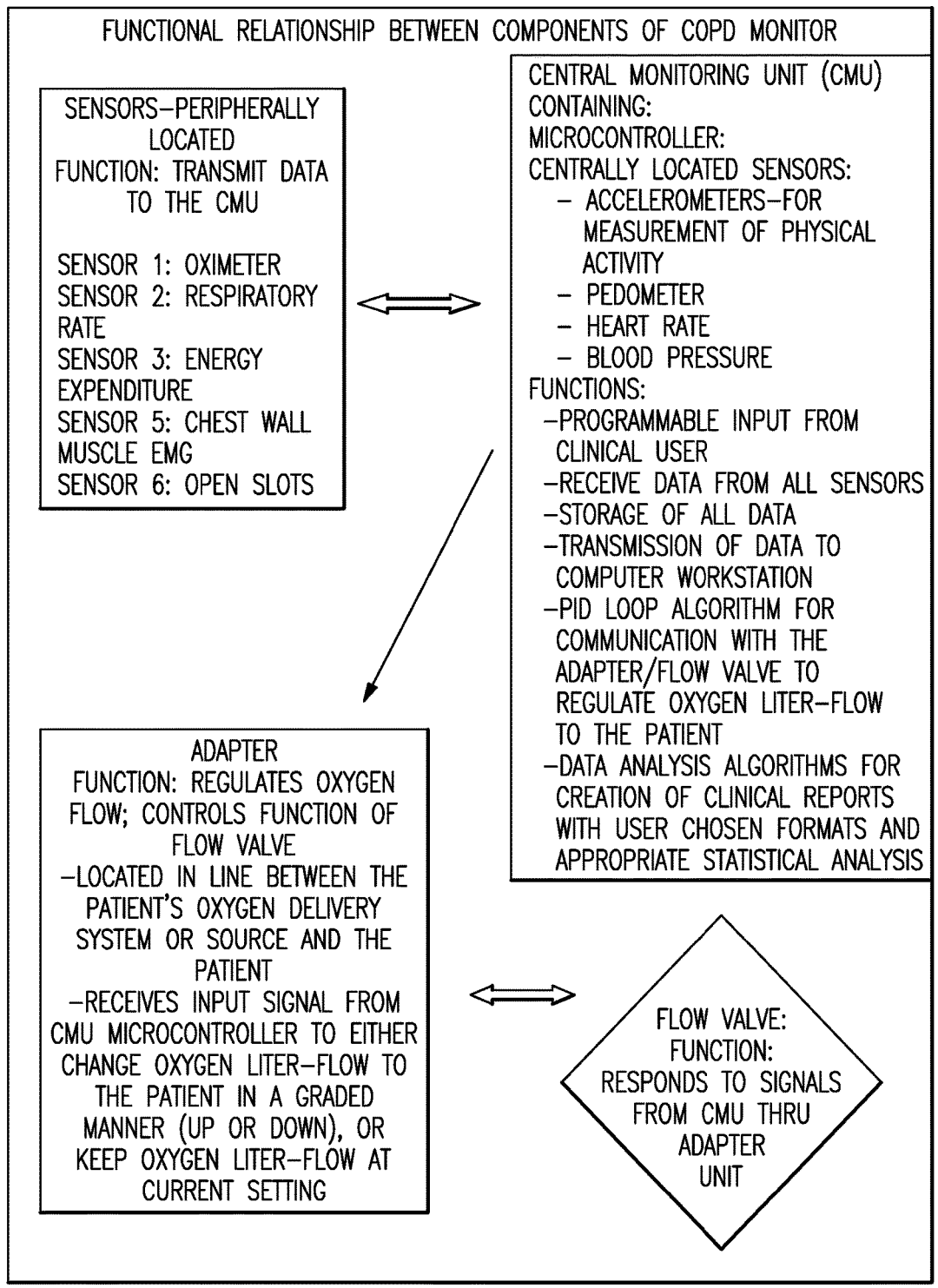
FIG. 2 shows another exemplary simplified block diagram of components of the COPD monitor and the interrelationship of components to one another.

FIG. 2 shows another exemplary simplified block diagram of the components of the COPD monitor and the interrelationship of components to one another. The components include: multiple sensors, a central monitoring unit (CMU), and the adapter/flow valve unit. The sensors are communicatively coupled to the CMU and send data to the CMU that stores, analyzes, and performs data analysis functions on these data continuously. Note that some of the sensors can be located within the housing of the CMU. Other sensors (oximeter, respiratory rate, energy expenditure, chest wall muscle EMG) are typically located peripherally on the patient's body, as indicated in FIG. 1F. In some embodiments, the adapter/flow valve unit can receive signals from the CMU related to the function of monitoring and optimizing oxygen delivery using a proportional-integral-derivative (PID) loop control algorithm as illustrated and described in more detail with respect to FIG. 3A.

It is understood that other embodiments are possible related to the ongoing, rapid development of new types of sensors with different functional capabilities, including the ability to record from different points of attachment to the human body, different size (miniaturization), or different data processing capabilities, to name a few.

Figure 3A:
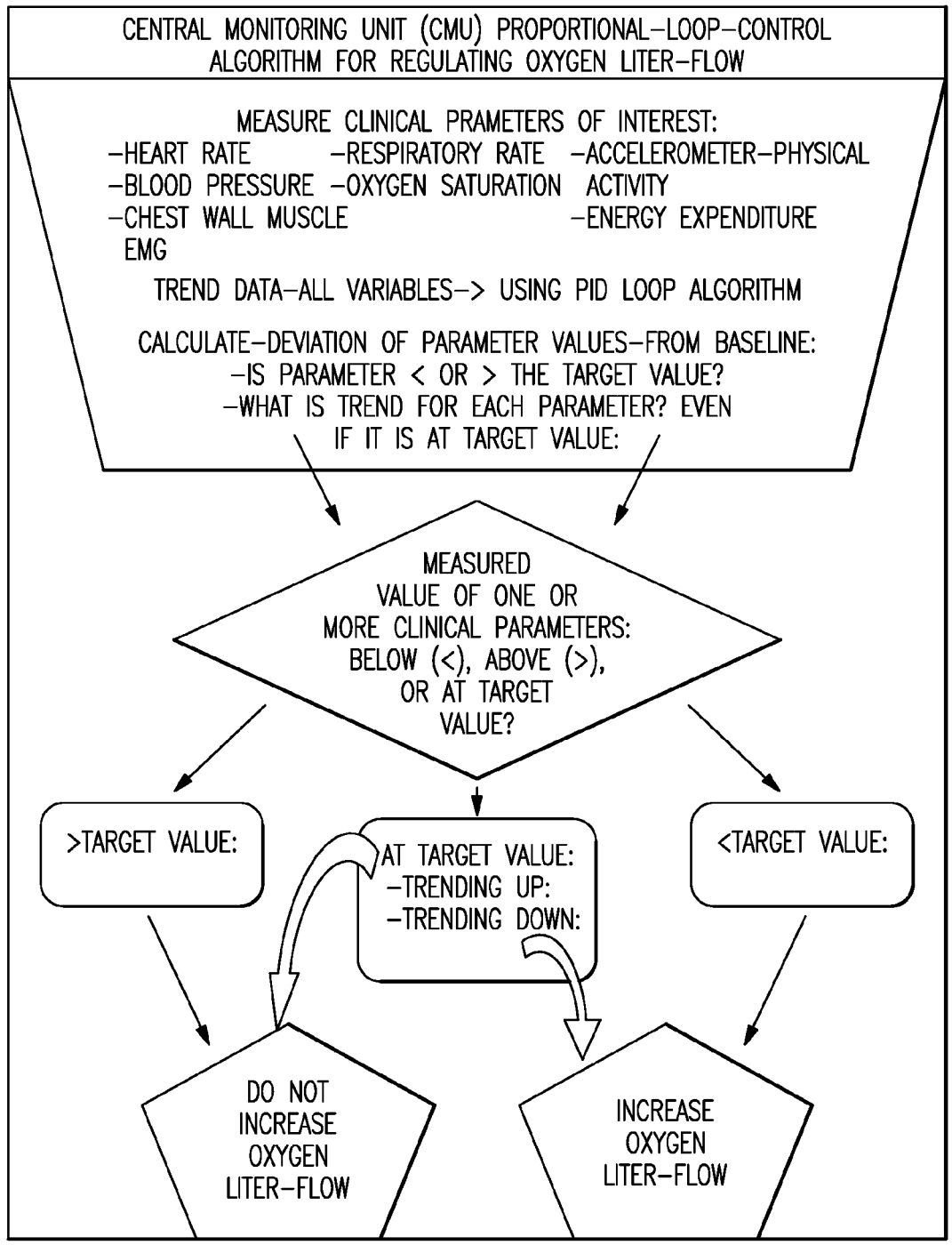
FIG. 3A shows a block diagram of one exemplary embodiment of a closed loop control process suitable for use with the COPD monitor.

FIG. 3A shows a block diagram of one exemplary embodiment of a closed loop control process suitable for use with the COPD monitor. In the embodiment of FIG. 3A, the CMU regulates oxygen flow to the patient thru a PID feedback loop process (typically including one or more algorithms in software or firmware). Oxygen flow is controlled by the CMU via the adapter/flow valve unit. Control of the flow valve is the result of continuous output of the proportional-integral-derivative (PID) loop control process. This process uses data from one or more of the sensed and measured clinical parameters that are continuously monitored by the sensors to determine if specified normal target values for each parameter (oxygen saturation, respiratory rate, heart rate, physical activity, or the trends for each variable) are stable or changing. The process algorithm uses the magnitude of the deviation from normal target values of each parameter to initiate a change in oxygen liter-flow/min thru the adapter/flow valve unit. The CMU then sends the appropriate signal to the adapter which is translated into a change in liter/flow per minute of oxygen to the patient by changing the position of a flow valve that controls the flow of gas from the gas source to the patient.

In one exemplary embodiment, one or more of the sensor measurements of clinical parameters other than oxygen saturation, such as physical activity, energy expenditure, respiratory rate, chest wall muscle EMG, etc, can serve as the primary determinants of the final signal generated by the CMU to regulate oxygen flow via a PID closed loop algorithm. In this embodiment, the oximeter sensor data can serve only as a reference target value, and is not necessarily part of the final input signal that determines the regulation of oxygen flow to the patient. It is understood that this algorithm does not exclude the addition of other parameters at the discretion of the user. The advantage of this type of algorithm is that changes in physical activity or other parameters that indirectly reflect a change in the patient activity level, such as respiratory rate, energy expenditure, or chest wall muscle EMG, will often precede changes in oxygen saturation. It is common in patients with chronic lung disease that increased exertion is then followed by a decrease in oxygen saturation. Therefore, changes in these parameters can be used to improve the regulation of oxygen flow because they precede a change in oxygen saturation in the patient.

The CMU can either: increase, decrease, or not change the oxygen liter-flow. The CMU causes a change in oxygen liter-flow per minute by changing the position of a valve that controls the flow of gas from the gas source to the patient. This change in valve "position" is understood to be either a change in the degree of valve opening or the length of time the valve is open, or by any other suitable means to control air flow from gas source. In some embodiments, there can be two or more options for valve gas flow control modes. The process algorithm can have a hierarchal form of function in that it can be formatted to use the data on one or more parameters in a predetermined order, as follows: measurements of respiratory rate, heart rate, physical activity or other indices of exertion level, oxygen saturation, or finally, the trends for each of these parameters. It is understood that this predetermined order can be altered by the user such that only one or several specified parameters are employed in this hierarchal function. For example, only physical activity or respiratory rate, or the overall trend of these two selected variables together can be used to determine if oxygen liter-flow is changed. In this latter embodiment, the general hierarchal function is illustrated in the following way: the detected or measured trend in the selected variables will be used to determine the final signal generated for a change in oxygen liter-flow. Use of the trend function in this way enables the system to respond more rapidly to changes in the parameters even before target values of oxygen saturation are out of the normal range. In this fashion, the development of clinically significant decreases in oxygen saturation can be anticipated and minimized or avoided. Similarly, the target values of the parameters used by the algorithm can be set to user-chosen values in order to initiate a change in oxygen liter-flow at an earlier time point. Setting the target value of oxygen saturation at 92% rather than 90% means that the algorithm will initiate a change in oxygen liter-flow when saturation is <92% rather than waiting for saturation to drop below 90%. In this way, the need for increased (or decreased) oxygen liter-flow can be anticipated more effectively in a patient-specific manner.

It is understood that the CMU may not generate a signal to change oxygen liter-flow if the process algorithm does not detect a significant deviation from the target values of the chosen parameters. Similarly, when monitored parameters return to a baseline, a signal can be generated to return oxygen liter-flow/min to a baseline level specified by the user.

It is understood that the user has control over the frequency of how often incoming physiological sensor data are analyzed by the CMU, and then relayed to the adapter/flow valve for modification of oxygen liter/flow per minute. It is also understood that the target values of the parameters used in this algorithm can be set by the user.

Finally, the data analysis process algorithm typically includes a means to adjust for invalid data. It is understood that invalid data can occur in several forms, including: 1) well-known problems with oximetry data, including a disconnected sensor, inadequate signal related to poor perfusion at the sensor attachment site, disparate values from previously obtained data, or inappropriate heart rate data which generally take the form of error flag messages that are received by the microcontroller from the oximeter unit. 2) similar types of errors from any of the other sensors. Therefore, the process algorithm includes an artifact and "poor data" default response plan. There are various well-described approaches to detection and implementation of a default response to manage oxygen liter-flow when artifacts and poor data are detected. These include, for example: an exponentially-weighted mean of measured data from all sensors over a chosen time interval or other mathematical approaches, such as harmonic or geometric mean averaging procedures. It is understood that additional approaches to the detection of invalid data are not excluded by this mention of possible procedures. The final result is that no matter what procedures are chosen for detection of invalid data, the CMU, for example, can send a default signal to the adapter/flow valve unit such that oxygen liter-flow will be delivered to maintain oxygen saturation at a minimum of 92%.

Figure 3B:
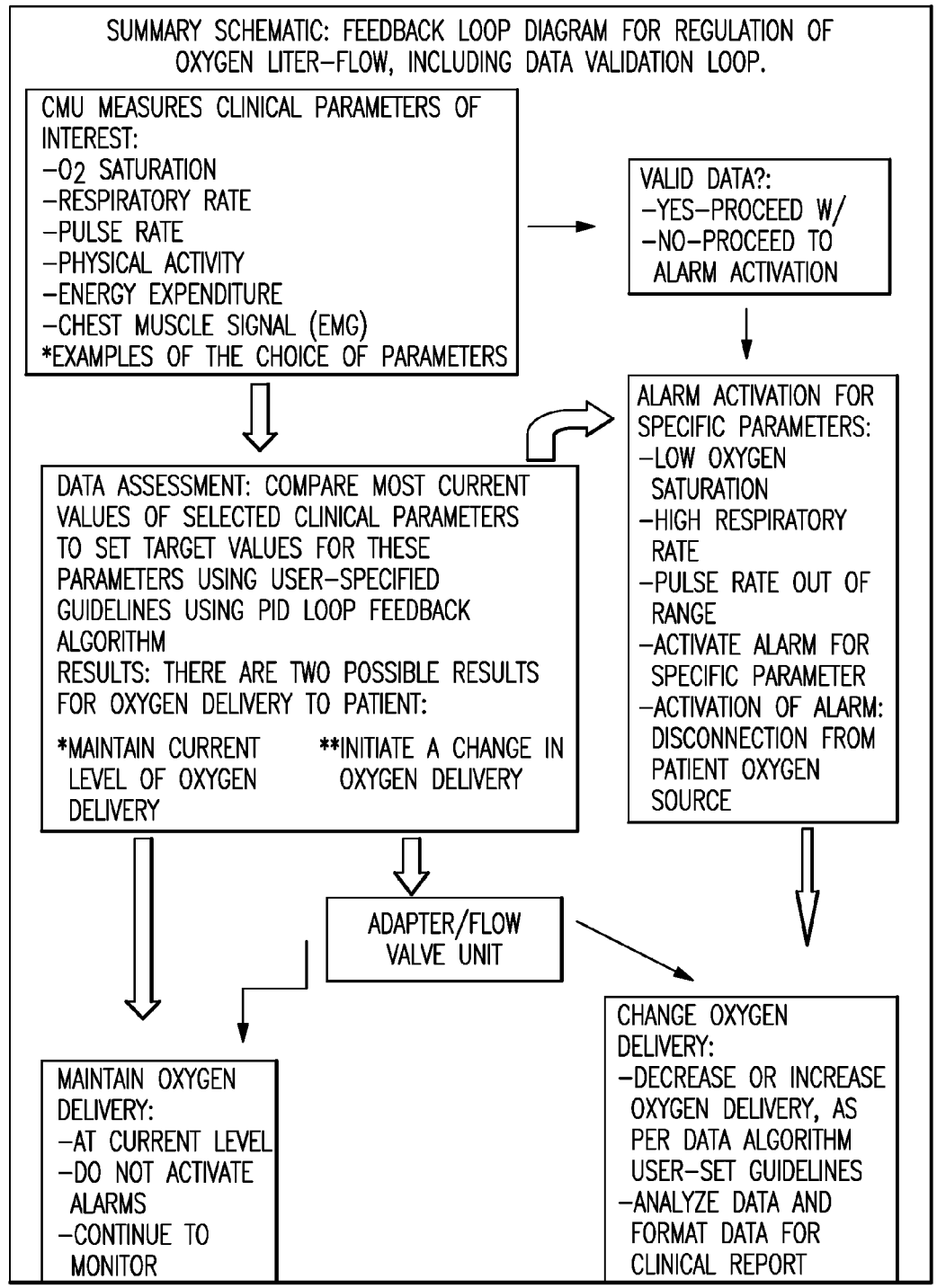
FIG. 3B shows an exemplary feedback loop diagram for regulation of oxygen liter-flow, including a data validation loop suitable for use in the COPD monitor FIG. 3A.

FIG. 3B shows an exemplary block diagram for regulation of oxygen liter-flow, (e.g. to control oxygen liter-flow) including a data validation loop suitable for use in the COPD monitor FIG. 3A. The CMU continuously controls the adapter/flow valve unit for regulation of oxygen liter/flow per minute in response to changes in user-defined target values of the parameters chosen as part of the data analysis process algorithm (e.g. set by the user in FIG. 3A). The user also has control over the frequency of how often sensor data are analyzed by the CMU, and then relayed to the adapter as a signal for modification of oxygen liter/flow. This signal is dependent upon the magnitude of deviation from chosen target values of one or more of the parameters participating in the closed loop operation. Alternatively, if all clinical parameters are within the acceptable range, no change in oxygen liter/flow is initiated. An invalid data algorithm is also illustrated where aberrant out-of-range values of each clinical parameter are detected, and an alarm activated along with a time-stamped event noted in the patient recording that captures this specific event.

Any CMU program process code (e.g. algorithms or processes) can be provided and/or stored within the CMU on a computer readable non-transitory storage medium. Process code (e.g. algorithms or processes) as described herein typically include computer readable code configured to be run on a computer in the CMU and/or another local computer (e.g. for analysis and/or formatting and reporting accomplished in another compute A method for acquiring and analyzing human physiological data and regulating oxygen flow to a patient with chronic lung disease:

The system and method described herein is designed for acquiring, analyzing, and formatting data obtained in the outpatient setting in patients engaged in activities of daily living that can be used to manage chronic lung disease. The method or process steps include: CMU acquisition of the human physiological data and regulating oxygen flow to the patient with chronic lung disease in an outpatient setting during activities of daily living; analyzing by the CMU of the human physiological data, including the data related to the regulation of oxygen flow to the patient with chronic lung disease in an outpatient setting during activities of daily living; generating by the CMU one or more reports of the human physiological data, including data related to the regulation of oxygen flow to the patient with chronic lung disease; and managing treatment of chronic lung disease responsive to the one or more reports.

The step of generating one or more reports by the CMU can further include the generation of reports over a specified time period. The type of report can be selected from the group of template reports focused on any of the monitored parameters (physical activity, oxygenation, blood pressure, respiratory rate, energy expenditure, chest wall EMG, oxygenation), as a report that includes the temporal profile of more than one parameter. The steps of acquiring by the CMU the human physiological data and regulating oxygen flow to the patient can occur for a specified period of time and during activities of daily living (rest, exertion, and sleep). The step of generating by the CMU the one or more reports wherein one or more of any acquired sensor data can be correlated to one or more of any other acquired sensor data, at the user's discretion.

Examples of Clinical Use of the COPD Monitor System and Method:

Effective use of the system and method is linked to CMU-based use of the software/firmware to acquire, analyze, and format the human physiological data in a multitude/plurality of use-chosen formats to illustrate correlations among these data. It would be difficult, if not impossible, to accurately determine these correlations without the computer-based capability provided by the software/firmware of the COPD Monitor. This software/firmware (or computer program containing more than one algorithm) formats and analyzes the data in user-chosen formats that enables the user to visualize/observe the patient-specific temporal profile of the relationships between the acquired data. Without this analytical capability, correlations among types of data would be undetectable and unavailable to the user. Thus, the ability to modify management is enhanced in accord with the capability to demonstrate the correlations among acquired data.

It is important to note what is absent from many examples in the field of data acquisition in the outpatient setting. There is a lack of focus on creating tools that can monitor clinical parameters of interest while patients engage in normal activities of daily living with the goal of having medical professionals use this data for disease management. This new technology is often aimed at the athlete and the neurotic "worried-well" market. Such systems are often proposed as patient self-management systems. The problem with this approach is that untrained subjects or patients cannot be expected to interpret the results of a large stream of physiological data, especially the type of data acquired using the system and method described herein (FIGS. 4-5). Appropriate interpretation of results in the context of chronic disease management is best done by a medical professional. Complicated data streams still need to be interpreted in order to be used effectively. The system and method described herein is designed to be used by medical professionals who can understand and properly apply the results.

The system and method described herein provides the medical provider with a patient-specific data analysis as the basis for therapeutic recommendations. This strategy recognizes that while patients may share a diagnosis of chronic lung disease, there are an infinite number of differences in life circumstances, disease characteristics and severity, comorbidities, and motivation that require individualization of therapeutic recommendations. There is no "one size fits all" set of recommendations that are appropriate for all patients.

Examples of key findings from patient recordings that would alter management are given below in FIGS. 4A-E. These examples clearly illustrate the step of generating clinical reports based on the acquisition and processing of data obtained in the outpatient setting that can be used by medical professionals to modify disease management. This type of clinical report, based on data acquired in the ambulatory setting, are not currently part of standard practice for management of chronic lung disease.

Figure 4A:
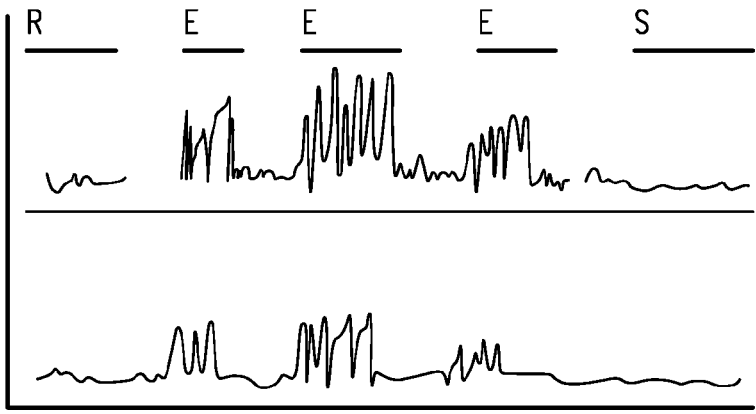
FIG. 4A shows one exemplary COPD monitor system and method clinical report that summarizes the temporal profile of physical activity during "rest, exertion, and sleep"

FIG. 4A shows one exemplary COPD Monitor system and method clinical temporal profile of physical activity (rest, exertion, and sleep). In the exemplary clinical report of FIG. 4A, the physical activity of a hypothetical patient with chronic lung disease is shown for one 24-hour period. The recording illustrates the temporal profile of physical activity starting at 8 am one day and ending at 8 am the next day. The exemplary intensity of physical activity is quantitated with two accelerometer sensors shown on the Y-axis for more precise discrimination between activity categories (R-rest, E-exertion, S-sleep). The accelerometer data is translated into different activity categories (rest, sleep, walking, etc.) based on a data analysis algorithm created to distinguish these categories using the accelerometer signals. The X-axis illustrates time of day. In this hypothetical patient, we can see episodes of rest alternating with exertion of variable intensity during the day that then transitions into sleep during the nocturnal hours. The CMU data analysis process also calculates and indicates the amount of time the patient spent in each activity during this recording period in two forms: % of total activity and actual time (minutes). This definition of the temporal profile of activity enables the provider to assess the activity profile of a patient and make recommendations for physical activity based on this individual's performance during activities of daily living.

FIG. 4B shows another exemplary COPD Monitor system and method clinical report on temporal profile of oxygenation and physical activity for rest, exertion, and sleep. FIG. 4B illustrates the temporal profile of oxygenation of a patient with chronic lung disease in the upper panel over a 24-hour period. In addition, the temporal profile of physical activity that correlates with this oxygenation profile is also shown in the bottom panel (only one activity channel shown). The oxygen saturation values are measured using the oximetry sensor as % saturation. The upper panel also includes a horizontal dotted line indicating the 90% oxygen saturation level which indicates the cutoff position for adequate versus inadequate oxygenation. The X-axis illustrates time of day from 8am on day one to 8am on day two. From this recording, it is easy to discern the specific periods during the day when oxygen saturation of the patient does not meet the recommended target value of 90% saturation and the correlation with the type of physical activity (rest, exertion, sleep marked as R,E,S, respectively) the patient was engaged in at that time. In this example, there were two periods of exertion in afternoon and evening during which oxygen saturation was consistently <90% for the majority of these exertion periods. The CMU data analysis algorithm also calculates and indicates the amount of time spent below the chosen target value of oxygen saturation (90%) during the different physical activity categories for the recording period. This clinical report illustrates the temporal profile of oxygenation and activity in a hypothetical patient with chronic lung disease. This profile can be reviewed by the provider with the goal of identifying the magnitude of hypoxemia during activities of daily living. These data can then be used to make recommendations for an individual patient, including prescribing LTOT in a patient not already on this therapy, or modifying LTOT to achieve more acceptable levels of oxygenation during different categories of daily activity.

Figure 4C:
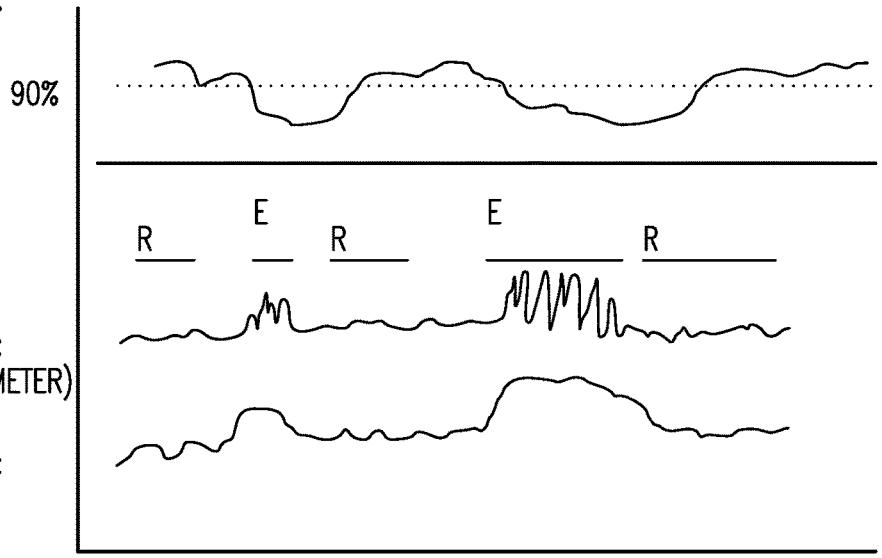
FIG. 4C shows an exemplary COPD monitor system and method clinical report that summarizes more quantitative aspects of the temporal profile of the magnitude and duration of physical activity and oxygenation during rest and exertion (excluding sleep)

FIG. 4C shows and exemplary COPD Monitor system and method clinical report on additional quantitative aspects of the monitoring of physical activity correlated with oxygenation profile in an individual patient. Similar in content to FIG. 4B, this user-chosen format can be used to demonstrate the effect of a change in an exercise prescription on physical activity and oxygenation profile of a patient. Unlike FIG. 4B which is focused on a qualitative identification of the basic categories of activity (rest, exertion, sleep), this report provides in depth quantitative information about the duration and magnitude of daily activity (excluding sleep) using both an accelerometer sensor and EMG sensor to monitor physical activity simultaneously. This approach enables the user to effectively correlate this activity with the oxygenation saturation profile in a more quantitative manner.

This report format could be used as part of a baseline assessment of the physical activity, or to assess the response to a change in the exercise prescription. This exercise prescription may be part of a structured pulmonary rehabilitation program or a prescription for a patient to change their type and magnitude of daily physical activity. This format allows the provider to perform multiple assessments and compare the pre and post-program results in terms of how the profile of physical activity and oxygenation were modified by the change in the exercise prescription (only a baseline study shown). Superimposition of the temporal profile of oxygen saturation with physical activity in this manner enables the medical provider to more precisely understand the relationship between the physical activity and oxygen saturation (e.g. the activity/oxygenation profile) pre and post modification of an exercise prescription. This information will have great value when applied to disease management; specifically, for assessment of patient performance during different phases of activity, optimization of LTOT, or determination of an appropriate exercise prescription.

It is noteworthy that a recent recommendation suggested an expansion of exercise programs for patients with chronic lung disease by recommending "activity monitored-based counseling" that can be used to optimize exercise prescriptions [34]. This recommendation could be accomplished using the data acquisition format illustrated in FIG. 4C.

In this example, the temporal profile of oxygenation (top panel) that correlates with the activity profile shown in the bottom panel (two accelerometer data channels shown) is instructive. Oxygen saturation values are measured using the oximetry sensor as % saturation. The upper panel includes a dotted line indicating the 90% oxygen saturation level as in FIG. 4B. In this hypothetical patient, who underwent a recording from 8 am to 4 PM, we observe that the patient's physical activity time was divided between rest (R) and exertion (E) as follows: rest-83% (398 min) versus exertion: 17% (82 min) with a total step count of 1625 during the exertion period. The corresponding oxygenation profile shows that oxygenation remained at acceptable levels during the rest period, but decreased to an average of 84% (range-80-90%-parentheses) during exertion. The provider for this patient verified that on a previous recording the patient demonstrated no oxygen desaturation during exertion (data not show) in this hypothetical example, but the time of exertion was only 2% of total physical activity. It was apparent from this new recording that once the patient increased his exertional activity, he developed oxygen desaturation.

The value of this detailed analysis is that a patient-specific recommendation can be made by the medical provider. The activity/oxygenation profile was altered by the new exercise prescription such that the patient required more supplemental oxygen during exertion. The recommended change in management to increase oxygen liter-flow during exertion only emerges after a medical professional review of the recording in FIG. 4B. This type of management does not currently exist for chronic lung disease, but can be accomplished with use of the system and method discussed herein.

Figure 4D:
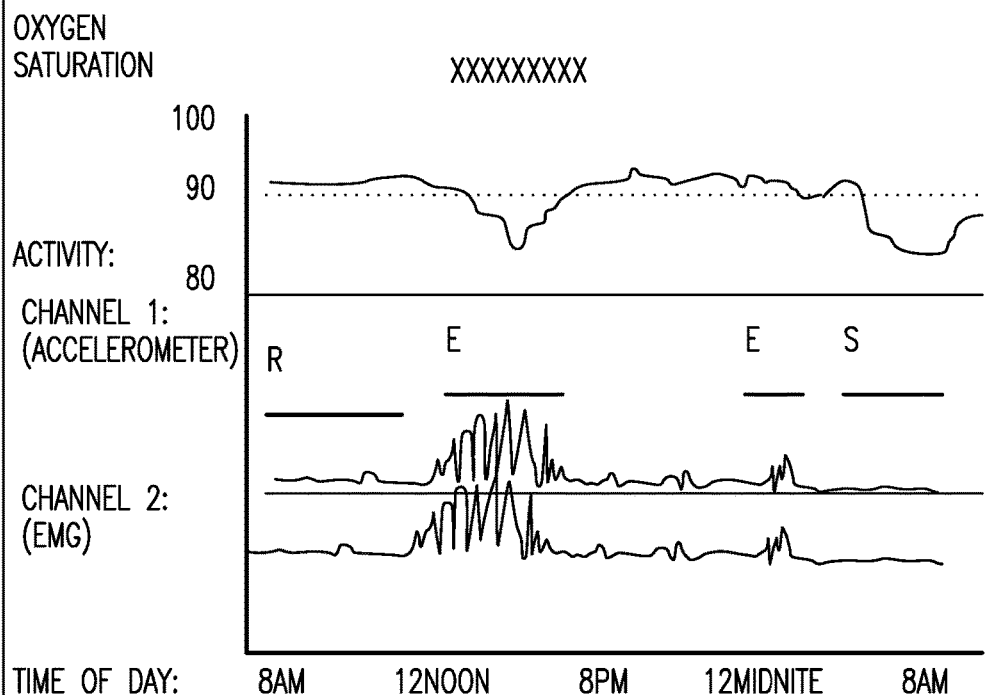
FIG. 4D shows another exemplary COPD monitor system and method clinical report that summarizes the determination of the efficacy of a LTOT prescription, including patient compliance with LTOT in an individual patient.

FIG. 4D shows an exemplary COPD monitor system and method clinical report to determine the efficacy of an LTOT prescription and patient adherence to this prescription in a hypothetical patient during a 24-hour measurement period. In this example, the magnitude and duration of physical activity is measured with both either with an accelerometer sensor and/or EMG sensor with the signals from each sensor recorded simultaneously. In addition, the temporal profile of oxygenation is also measured simultaneously with physical activity.

The format in this example is similar to FIG. 4B, FIG. 4C, in that both the temporal profile of oxygenation and physical activity are shown on the Y-axis versus time of day on the X-axis. Physical activity is measured using an accelerometer signal and EMG signal simultaneously for a more precise definition of the relationship of exertion to changes in oxygen saturation. The recording documents on a minute-to-minute basis the adequacy of oxygenation or how often oxygen saturation meets the target level of oxygen saturation (90%) during different types of physical activity (rest, exertion only marked as R,E respectively) during the recording period. Note the horizontal line representing 90% oxygen saturation (dotted) on the oxygen saturation tracing that indicates the cutoff position for adequate versus inadequate oxygenation. The recording also indicates the time periods during which an oxygen delivery device was used by the patient and the periods when it was not in use (marked with X).

From this recording, it is easy to discern the periods during the day when oxygen saturation did not meet the target value of 90% along with the type of physical activity the patient was engaged in at that time. The period of exertion that occurred from ~12 noon for several hours was marked by a sustained decrease in oxygen saturation below 90%. Oxygen saturation reached a low of 83%. Also, this period of desaturation corresponded to an interval when the patient was not wearing the oxygen delivery device. There was also a desaturation during nocturnal hours that lasted for several hours down ~84%. The data analysis algorithm also gives a summary of the time that the patient was connected to the delivery device and the amount of time oxygen saturation was below 90% using the device. These data give the provider important information about patient compliance as well as the overall efficacy of the device in providing adequate oxygen supplementation during physical activity. These data can be used for patient counseling about the need for improved compliance during exertion and the possible need for oxygen supplementation during sleep.

Figure 4E:
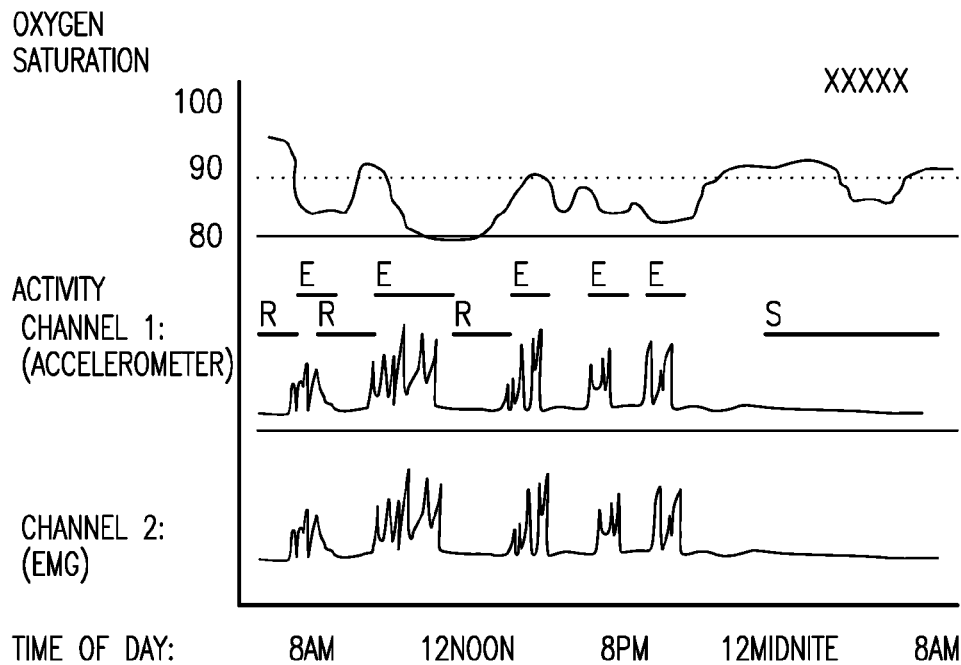
FIG. 4E: shows and exemplary COPD monitor system and method clinical report that summarizes the findings related to the efficacy of an oxygen delivery device in an individual patient.

FIG. 4E shows another exemplary COPD monitor system and method clinical report related to the efficacy of an oxygen delivery device that also employs the technique of simultaneously measuring physical activity with accelerometer and EMG sensors for increased precision in determining the relationship of changes in oxygen saturation to exertion. The objective of the use of the COPD Monitor in this example is to determine the efficacy of a specific oxygen delivery device to provide appropriate oxygen supplementation during a 24-hour measurement period.

This example illustrates how a medical provider can comply with the recommended procedure for testing the efficacy of a device on a patient before dispensing the device for long periods of time without such testing. While this type of evaluation is a recommended best practice for evaluating a delivery device [9,10], Applicant is unaware of any way to accomplish this type of evaluation in real time medical practice at this time. The format is similar to FIG. 4C with both the temporal profile of oxygenation and physical activity shown on the Y-axis versus time of day on the X-axis, respectively. The recording documents the ability of this hypothetical delivery device to meet the target level of oxygen saturation (90%) during different types of physical activity (rest-blue, exertion-green, sleep-brown) during the 24-hour recording. The horizontal line dotted line representing 90% oxygen saturation on the oxygen saturation tracing indicates the cutoff for adequate versus inadequate oxygenation. The recording also indicates the time periods during which the delivery device was worn by the patient and the periods when it was not in use (marked by X). Finally, the data analysis algorithm gives a summary of the amount of time that the patient was connected to the delivery device and the amount of time oxygen saturation was below 90% when using the device.

In this example, the patient achieves acceptable oxygenation during rest with only 1% of rest time with oxygen saturation <90%. In contrast, this patient demonstrates oxygen desaturation below 90% during almost all of the periods of exertion. The patient also demonstrates a period of desaturation during nocturnal hours when he is disconnected from his delivery device for a total of 33% of sleep time. The overall conclusion from this study is that this particular oxygen delivery device is failing to adequately provide supplemental oxygen during exertion. In addition, the patient is noncompliant with the device during part (33%) of the nocturnal hours when he also should receive oxygen supplementation. This type of detailed information about oxygen delivery and compliance is believed to be not currently available to medical providers. This would be valuable information that could be the basis for a modification of oxygen delivery and counseling on compliance as part of a disease management program.

In summary, this report gives the medical provider important information about the efficacy of a specific delivery system during all types of activity. The findings provide a basis for recommendations to optimize LTOT, consisting of either an increase in oxygen liter-flow during exertion, or a switch to a more effective system.

FIG. 4F shows an exemplary COPD monitor system and method clinical report related to the determination of the frequency, duration, and magnitude of hypoxemic events. FIG. 4F illustrates an oximetry tracing over a 24-hour period that defines the "hypoxemia event" profile of this hypothetical patient. The data analysis algorithm provides the following results: 1) the number of hypoxemic events; 2) the average duration of these events with a range; and 3) the magnitude of these events represented as a histogram that categorizes the severity of these events. Categorization of hypoxemic events provides a picture of the temporal profile of events during the recording. A characteristics of a hypoxemic event can be defined by the user. In this example, parameters are set by the user such that an event is defined as a decrease in oxygen saturation below 90% for a specified time; range: >5 seconds). Next, the algorithm counts the number of events and measures the length of events to determine the first two features noted above. Finally, the user selects a histogram format and specifies how to categorize the severity of the events. In this example, they are divided into decreases in oxygen saturation from baseline of <4%, 4-10%, or >10%, respectively. As shown in this hypothetical example, 54% of the events are in the range of 4-10% decrease from baseline. The categorization of the event severity is user defined and easily changed since all of these parameters are set by the user. The final part of the FIG. 4F includes a correlation of hypoxemic events with type of physical activity, as in FIG. 4E.

This type of detailed profile of hypoxemic events is not yet part of standard clinical practice. In providing the capability to assess the hypoxemic profile of individual patients, providers will have a new way to manage patients that will be based on real data acquired in the outpatient setting, thus providing a detailed categorization of these events. Follow up studies can refer back to these findings to note changes in the temporal profile of oxygenation. In this example, there were 45 measured hypoxemic events with an average duration of 29 seconds with severity distribution noted in the histogram; 16% of these events involved a decrease in oxygen saturation of >10% from baseline. The oxygenation profile during physical activity demonstrates that few events occurred during rest, while the majority of events occurred during exertion. In this patient, the next step would be to consider starting LTOT. Alternatively, in a patient already on LTOT, the desaturation events during exertion would suggest that either the prescription for LTOT during exercise needs to be revised, or that there is a need to replace the existing oxygen delivery device that is failing to oxygenate this patient during exertion. Finally, lack of compliance with the LTOT prescription could also be investigated as a possible explanation for this desaturation profile.

In conclusion, these findings give the provider insight into ways to provide more effective oxygenation during daily activities in this patient with chronic lung disease. This is important clinical information to act upon since untreated hypoxemia is correlated with increased mortality [1,9,15].

Clinical reports-cumulative trends: The CMU data analysis processes offer many options for illustrating cumulative data trends. The reports illustrated in FIG. 5A-E are are examples of some embodiments for viewing the data and results of studies on individual patients done at different times, or a comparison of results among different patients. The choice of a graphical versus tabular representation of results is a user choice. On one hand, representation using the graphical format (FIG. 4A-4E) is very useful to isolate specific events and visualize these events over an entire recording. Alternatively, as illustrated below, we show the use of a; summary analysis and statistics for different parameters displayed in a variety of formats. It is understood that the formats shown below do not exclude other possible embodiments of the data analysis capabilities of the method and system described herein that exemplify this proactive approach to disease management. Cumulative summary formats illustrate how different types of reports can be useful for patient management decisions.

FIG. 5A shows an exemplary COPD monitor system and method tabular representation for summary statistics for several variables measured during a 24-hour recording. All variables are shown as mean value +/−standard error (SE) of the mean as follows: RR-respiratory rate; BP-blood pressure-shown as a range of high→low; HR-heart rate; physical activity is shown in two forms: accelerometer activity counts and step counts; energy expenditure as calories per hour over the 24-hour measurement period; oxygenation as the average oxygen saturation (SpO2) per hour over 24-hrs and the average oxygenation during each category of activity: rest, exertion, sleep; and also the percent of time for each activity category that oxygen saturation was <90%. The data analysis process highlight results in can be shown, for example, in yellow to indicate where intervention may be required. The data summary illustrates findings for several parameters from recordings on different days in this patient, enabling a comparison of results for each parameter between days. In this example, there were stable vital signs along with physical activity and energy expenditure levels that were similar on these two days, along with excellent oxygen saturation at rest and during sleep. In contrast, oxygenation during exertion (e.g. can be shown in yellow) consistently did not achieve adequate levels on these two days, suggesting that a change in strategy for oxygen delivery is needed. Documentation of the levels of physical activity and energy expenditure serves as a baseline that can be the basis for additional recommendations to optimize physical activity in this patient.

FIG. 5B shows another exemplary COPD monitor system and method tabular representation of summary statistics illustrating a comparison of parameters limited to the temporal profile of oxygenation during physical activity in recordings obtained on different days. This temporal profile is illustrated for a hypothetical patient monitored on two separate days comprising a measurement period of 24-hours on each day. Oxygenation is indicated as the % of time that oxygen saturation was below 90% in each activity category. The actual time in minutes is shown in parentheses next to the % time below the target value. The data analysis process highlights results (e.g. in yellow) that may require intervention. This patient demonstrates an acceptable oxygenation pattern at rest and during sleep, but not during exertion on these two separate days. This is key information for this patient's caregiver to use in attempting to optimize LTOT. Additional formatting options, including the illustration of the total time of each component of physical activity in addition to the percentage and time the target value of oxygenation were not achieved, are not excluded in this embodiment. Additional options, such as expressing the results as mean values +/−standard deviation (SD) or standard error (SE) of the mean, or including a test of the significance of any observed differences among segments of a recording for each parameter i.e. test, analysis of variance, or a comparable nonparametric test of significance, are also not excluded by this example.

FIG. 5C shows another exemplary COPD monitor system and method clinical report in tabular representation for the summary of LTOT compliance in one patient during a chosen measurement period (8 am→4 PM) over many days. The chosen measurement period and number of monitored days is user defined. In FIG. 5C, the following format is used: % of total time the patient was using LTOT, or number of hours per day the patient was using LTOT is used. Additionally, the average oxygenation during periods of compliance versus noncompliance with LTOT are indicated for each monitored day. The report can also displays the temporal profile of oxygenation during different types of physical activity (rest, exertion, sleep) with a notation of whether the patient was using LTOT during each type of physical activity (data not shown). The Table summarizes the temporal profile of oxygenation and LTOT compliance from 8 am to 4 pm for each day of the 30-day recording period displayed. The data analysis process highlight results (e.g. yellow highlight) that may require intervention.

The study was done to determine patient compliance with LTOT during a specific period (8 am→4 PM) each day. Expected compliance would be 100% during this period on each day. In this example, patient compliance varied from a high of 100% on day 2 to a low of 63% on day 30 with intermediate values (not shown) on other days. Another key feature of this report is the documentation of average oxygen saturation values during the compliant versus non-compliant periods on each day. The report illustrates how valuable information about patient compliance would be missed in the absence of a study containing these details. The medical provider can investigate further into why the patient has days (day 30) of low compliance coupled with unacceptable oxygenation during non-compliant periods. This enables patient counseling to be focused and personalized. Patients often do not understand the importance of compliance with LTOT and maintaining an acceptable level of oxygenation at all times. They may think that a break "from wearing my oxygen' is acceptable.

FIG. 5D shows an exemplary COPD monitor system and method tabular representation for summary statistics for the performance of a specific LTOT delivery system in one patient. This report displays the data summary in a similar format to the report in FIG. 5C with the addition of a category for how effective the delivery system is for meeting the target value of oxygenation for different categories of activity. The format is for 5 different measurement periods of 24-hr duration in the same patient using the same delivery system. The user has multiple options for configuring reports as noted above in FIG. 5A-C. The data analysis process highlight results (yellow) that may require intervention.

This patient demonstrated problematic overall oxygenation ranging from 84-89% of the measurement time over the 5-day period. But, this is not the whole story. While the patient demonstrated acceptable oxygenation (>90%) at rest and during sleep for greater than 90% of these activity periods, oxygenation during exertion clearly did not meet the required level for optimal treatment of hypoxemia. This patient demonstrated a variable range of oxygenation during exertion in which the target value for oxygenation was only reached for 40%-60% of exertion time. (Note: actual minutes in each physical activity are not shown, but could be calculated and added to this report). This report contains information not currently available to providers who manage patients with chronic lung disease. One choice for intervention would be to increase the flow of oxygen (liters/min) during exertion and retest the patient on this same delivery system to determine whether acceptable oxygenation is achieved. Alternatively, a different delivery system could be used and evaluated as a possible replacement. As with all these clinical reports, this type of assessment is not part of standard management of chronic lung disease.

FIG. 5E shows another exemplary COPD monitor system and method tabular representation for summary statistics comprising a comparison of one or more clinical parameters among different patients on different days. In FIG. 5C, a simplified version of the temporal profile of oxygenation during exertion is illustrated for two hypothetical patients on three separate days. The data analysis process highlights results (e.g. highlighted in yellow) that may require intervention. In this example, only the temporal profile of oxygenation is compared during exertion; the physical activity categories of rest and sleep are excluded. As in prior examples, the % time that oxygenation during exertion does not reach the acceptable target value is indicated as a percentage of the actual time of exertion with time in minutes indicated in parentheses. In addition, the total time of exertion is also indicated for each patient since patients' may differ in the amount of exertion they engage in each day. Exertion is defined as all activity other than rest or sleep. In this example, Patient#2 achieves a more satisfactory level of oxygenation on each day compared to Patient#1. This is valuable information for Patient#1's provider to use in order to optimize LTOT. Several relevant questions can be asked. Are both patient's using the same or different oxygen delivery systems? Or, what is the level of compliance with the LTOT prescription in each patient? Is Patient#1 non-compliant? And, to what degree? The answers to these questions prompted by the data could lead to a change in delivery systems or appropriate counseling and retesting as part of optimizing LTOT in Patient#1.

FIG. 6 shows an exemplary table of COPD monitor functional components. FIG. 7 shows an exemplary table of clinical applications for the system and method as described herein.

COPD Monitor Components:

It is understood that in most embodiments, the COPD monitor device having the components described herein includes a system and a method for monitoring and assessing parameters linked to long-term outcomes of patients with chronic lung disease. The method comprises the totality of the device and system under discussion. In most embodiments, this method includes the COPD monitor device itself that can accurately acquire, store, analyze the requisite physiological data that represent the noted clinical parameters during an outpatient recording, along with the data analysis processes ("software" typically including one or more algorithms) that provide the ability to perform the data analysis. This data analysis capability is the basis for the generation of reports in user-defined formats that can then be used by a medical professional for clinical decision-making.

It is understood that the CMU containing the microprocessor is designed to provide overall control over the specific functions. Therefore, the choice of microcontroller will be determined by the desired functionality. Those skilled in the art will understand that alternatively, other embodiments can use discrete circuitry, such as A/D converter chips (ADC), logic arrays, or similar alternatives to achieve the same desired functionality. Similarly, it is unimportant whether the process is runs on a traditional microcomputer or microprocessor or on some alternative technology, such as, for example field programmable gate array (FPGA) running firmware code that mimics the functionality of a microprocessor.

It is understood that the sensors may be located on the body of the subject in a manner that facilitates accurate uninterrupted data collection and uninhibited physical activity of the subject. In one embodiment, the oximeter sensor can be located on the subject's wrist with a physical connection to the central housing unit located at the subject's waist. Alternative locations for the oximetry sensor include the upper arm, forehead, or ear. Alternative forms of communication with the central monitoring unit are also assumed possible and not excluded, including suitable "wireless" form of data transmission (e.g. radio frequency (RF), Bluetooth, etc.). The accelerometers for monitoring physical activity can be located within the same physical central housing unit as the CMU at the patient's waist. It is understood that there may be different embodiments in which the other sensors (pedometer, respiration, heart rate, blood pressure, etc.) will be located either in the central housing unit, or at an appropriate peripheral site on the patient's body. Similarly, in some embodiments, the sensor pick-up device or transducer can be located at a desired place on the patient's body while corresponding signal conditioning electronics are present in the CMU.

It is understood that different embodiments are possible in terms of location of various sensors that connect to the CMU containing the microcontroller that is located at the waist in many embodiments. Those skilled in the art will recognize that sensor technology is advancing rapidly. Often there are different technical approaches to measurement of a particular parameter. It is understood that examples of specific embodiments of sensor technology discussed below do not exclude alternative approaches as these technologies evolve. Finally, it is understood that the various sensors can either be connected directly to the CMU by wired connection or can be connected wirelessly. Specific sensors are typically present in all embodiments of the system and method described herein. For example, monitoring of respiration may be performed with an in-line sensor, such as a flow sensor (e.g. the Honeywell AWM2150 Microbridge Mass Airflow Sensor available from the Honeywell Corporation of Minn, Minn.) or any suitable equivalent unit that connects the patient to an oxygen delivery device or oxygen source. Alternatively, a new type of sensor, such as the acoustic monitoring device (Maximo Corporation; Irvine, Calif.) may be used for the same purpose. Monitoring of physical activity can be performed using more than one accelerometer, such as the Mini MotionLogger Actigraph (Ambulatory Monitoring Inc; Ardsley, N.Y.), the RT3 Research Tracker Accelerometer (StayHealthy; Monrovia, Calif.), or the Acti-Watch (Philips Corp; Andover, Mass.). More than one accelerometer is preferred to increase precision in differentiating between different forms of physical activity (e.g. rest, walking, sleep). Monitoring of physical activity in a different manner in the form of the number of steps taken by a subject can be done using one of several available commercial pedometers, such as the New Lifestyles NL 2000 Activity Monitor Pedometer (New Lifestyles Inc; Lees Summit, Mo.). Monitoring of oxygen saturation can be done using one of several commercial portable oximeters (Nonin, Inc; Plymouth, Minn.), Massimo Corporation, or Sensors for Medicine and Science (Germantown, Md.). Monitoring of heart rate and blood pressure can be measured with products designed to provide vital sign monitoring technology for the home environment (Soltera Wireless™, Inc; San Diego, Calif.).

It is understood that sensors continue to undergo rapid development and modification. Alternative choices of sensors for measurement are not excluded by the above choices. It is understood that embodiments of the COPD Monitor may employ emerging sensor technology solutions as they become available. For example, disposable wearable sensor technology is one of the latest developments that could make a large impact on the field of ambulatory monitoring (Avery Dennison Medical Solutions; Chicago, Ill.) Improved methods of sensing or measuring the variables will continue to develop. Similarly, improvements in accurately measuring respiratory rate and the volume of each breath with new sensor technology are under development (Respiratory Motion, Inc; Waltham, Mass.). It is understood that these continued technological developments may lead to changes in the location of specific sensors on the patient's body, reduction in size of components, or other important characteristics or features of these sensors. It is understood that such technological developments are not excluded from the system and method described herein based on a description of a particular embodiment.

Along the same lines, continued advances in wireless and computer technology, including enhanced memory capacity, enhanced battery capacity, extended range, decrease in size of monitoring units, connectivity to smart phones, use of smart phones and other portable devices for data collection, data transmission, and storage, and more accurate capture of events suggest that future embodiments of the system and method described herein are anticipated with improvements in existing technology. Thus, additional embodiments are not excluded by the present description of various components and are understood to lie within the scope of the systems and methods described herein.

It is understood that the collected data from the sensors can be stored in non-volatile (i.e. non-transitory) memory. The CMU can serve a plurality of functions, including data capture, data storage, data analysis, and error handling of all input from the plurality of sensors. In some embodiments, the CMU can include a storage area network (SAN) that can act as the central repository of all collected data until a download to a computer workstation is completed. As noted earlier, data storage and memory capacity are areas where substantial progress has been made in increasing the capacity of these components. Therefore, in one preferred embodiment of the system and method described herein, data storage capacity can be maximized with the goal of enabling comparisons of key parameters from different recordings done at different time intervals. One such exemplary SAN device is the Symmetrix product (EMC Corp; Hopkinton, Mass.). Other suitable commercial SAN units can be used. It is understood that multiple network storage devices of varying capacities could be used. It is understood that alternative configurations for data processing are also possible. It is understood that the term "computer workstation" can also comprise alternative computer devices that can transmit or receive data, including but not limited to commonly used devices as Blackberry (Research in Motion, Inc; Waterloo, Ontario, Canada) or an iPad (Apple Computer; Cupertino, Calif.), tablet, notebook computer, laptop computer, desktop computer, personal computer, Apple OS desktop or laptop computer, or any similar or equivalent device, including any suitable cell phone, such as a "smart phone".

The COPD monitor typically includes a 24-hour clock that will provide a mechanism for time-stamping all collected data obtained from the various sensors during a recording. In addition, the CMU functionality will typically include the capability to record and retain user-entered demographic data on each patient, including patient factors such as, for example, name, sex, age, weight, height and any other suitable demographic data.

Throughout this description, the terms microprocessor, microcontroller, and microcomputer are used interchangeably herein. One example of a potentially suitable microcomputer is available from Microchip Technology, Inc (Chandler, Ariz.). As is well known to those skilled in the art there are many manufacturers of many types of microcomputers, microprocessors, microcontrollers, or functional equivalents in programmable devices, such as, for example, FPGAs which can be used to provide the CMU functions and run the computer processes described herein. Any physically small portable computer suitable for use in embedded applications can also be used. It is understood that specifications such as power consumption, cost, memory size, clock speed, and part availability may alter the final choice of a microcomputer, microprocessor, microcontroller, or any other suitable computational electronic components. Accordingly, this will enable a CMU (typically, but not necessarily, based on a microcomputer or microprocessor) to perform various calculations, including but not limited to elapsed time over specified intervals, on the acquired data for display to the end user. It is also understood that all data will typically be time-stamped on entry into the CMU so that final reports will demonstrate a uniform time stamp across all monitored parameters. Furthermore, in some embodiments, the device will include a means to enable manual time stamping of data either by the patient or a medical professional reviewing the record after the recording period has ended. In the former case, the patient can use this feature as an event marker (patient indicated events) during the recording. In the latter instance, the clinical provider or technician reviewing the data from the recording following download to a computer workstation will be able to mark specific events or intervals of time that are of interest following completion of the study. It is understood that a plurality of analysis functions can exist to enable the end user to analyze the recording or chosen sections of the recording in numerous ways as discussed below. It is also understood that a plurality of additional information can be obtained by the data stream from the various sensors, including but not limited to, error flags that evaluate the reliability of the data obtained from each sensor according to specified standards.

It is understood that as technology continues to advance, there may be alternatives to a preferred microprocessor/microcontroller, such as various types of discrete circuits, including programmable logic arrays, analog to digital converters (ADC), or analog comparators. It is understood that the use of such alternatives is not precluded in future embodiments of the system and method described herein.

It is unimportant what functions are performed by analog electronics or by digital electronics, or by software and/or firmware processes. For example, some sensors or sensor transducers generate as output an analog output. Such analog outputs can be converted to digital values at the sensor (e.g. in the case of wireless sensors which typically communicate digital values) or closer to microprocessor, such as, for example by an analog to digital converter (ADC) either as a separate component or as part of a microcomputer integrated circuit. In most embodiments, the control and closed loop control functions described herein are performed by a microprocessor (microcontroller, microcomputer, etc.) typically contained within a CMU, typically worn at the waist of a patient. However, any of the measurement and control functions described herein can be performed by analog electronics, digital electronics, processes in software or firmware, or any combination thereof. Some COPD monitor functions, such as the creation and generation of digital output data for reports and/or clinical report generation in embodiments where the COPD monitor performs such functions are understood to be digital processes typically performed by software and/or firmware running on a microprocessor of the COPD monitor.

Uploading of data to the computer workstation at the completion of a recording can be accomplished in several ways. For example, data can be transferred to a computer workstation by a direct physical, typically wired connection, such as by a connecting cable. Two exemplary form of direct connection are a direct serial connection via RS232 or USB port, or conventional phone lines that link the monitoring unit with the computer workstation via any suitable phone modem. Any other suitable direct connection between a COPD monitor and a computer can be used. Typically, this data transfer will occur at the conclusion of a patient recording. Alternatively, in other embodiments, data transfer can occur via a wireless transmission from the CMU to a computer workstation. This transfer can be accomplished by a short-range wireless transmission, such as, for example, infrared or radiofrequency (Bluetooth™, WiFi, WiMax, or any other suitable RF wireless connection means) to a computer workstation. Another embodiment of the COPD monitor can have a capability to download data using a wireless connection during a recording via an internet connection to a specific site. The specific site can be specified by the clinical provider prior to the start of a recording. This description does not exclude additional modifications to achieve the same or additional functionality in other embodiments.

Irrespective of the mode of downloading raw data, the data analysis algorithm in the CMU will have the capability of organizing and formatting the raw data based on choices made prior to the initiation of the study by the user or following a download to a remote workstation. These options will enable data analysis to be completed more quickly post-recording and facilitate interpretation and translation of the results into report formats that can be used for patient management. The data analysis process (including software and one or more algorithms) is designed specifically to collect data on a set of key clinical parameters monitored in the outpatient environment in patients with chronic lung disease engaged in activities of daily living.

For example, in some embodiments, the data analysis algorithm can compare and summarize the results of one or more parameters (physical activity, oxygenation, chest wall muscle EMG, etc.) for different time intervals in any suitable report format that facilitates understanding of the results for an individual or a group of patients (FIG. 3, FIG. 4, or FIG. 5). Comparisons can be in the form of a graphic display with a summary table of differences among clinical parameters over chosen time intervals. It is understood that analysis of recordings done at different times on the same patient (for example, the comparison of the profile of oxygenation during different categories of physical activity one month apart), or a comparison of parameters between patients (comparison of the profile of oxygenation during different categories of physical activity between different patients) is possible. For example, FIG. 4A illustrates an exemplary activity/oxygenation profile during different categories of daily physical activity in one patient over a 24-hour period. A useful next step would be to repeat this study and compare results on two different occasions. In this example, there is a difference in oxygen saturation during exertion at rest versus during sleep. Repeating this study at a different 24-hour time interval would provide powerful confirmatory evidence that this patient is or is not receiving adequate oxygenation during sleep. This is important information for chronic disease management and optimization of LTOT. Additional exemplary graphic and tabular display of the results using data are shown in FIG. 4 and FIG. 5. This type of functionality is not available for chronic lung disease management at the present time.

In some embodiments, the choices for formatting the raw data begin with a selection of target values for each parameter used as reference values ("normal values" or baseline values") and what are the allowable ranges for deviation from these reference values. For example, the user may choose a set format using a modifiable template with reference values in which oxygen saturation for each different type of physical activity (rest, walking, sleep) is presented in graphic or tabular form for the entire study. Using this format, the user could then analyze the data for any differences from a user-chosen baseline value for oxygen saturation (actual time or % time in which oxygen saturation was <90%) during each physical activity category, as shown in FIG. 4B. It is understood that additional customization of this template is possible by the user. For example, one such possibility can include changing the visual display of the data to show oxygen saturation values for the entire study at chosen specified time intervals (every minute, five minutes, or hour, etc.) of the recording. It is understood that there are multiple additional possible choices for data formatting that are implied as part of the data analysis algorithm. Furthermore, it is understood that formats can be changed by the user at any time to illustrate the data in a different way.

This type of functionality expands the analysis capability of the system and method described herein by enhancing clinical decision-making of the medical professional user. After a review of the recording, the user may decide that an alternative data analysis format is more practical or useful for illustrating the results. It is understood that in many embodiments, more than one template for data presentation is available for illustrating results in order to display temporal profile trends or summary statistics for the entire recording or segments of the recording. Additional examples of possible formats are illustrated in FIG. 4 and FIG. 5. It is understood that templates are not limited to these examples. An advantage of having set templates is that a graphical representation of results for a chosen time interval can be easily called up for display on a remote computer workstation.

Formatting of raw data with a user-selected format using one of the pre-set templates or a customized version created by the end-user will typically occur at the completion of the recording after the data has been downloaded to a computer workstation. In one embodiment of this process, the data can be formatted within minutes of download to the computer workstation by selections made by the user. This functionality of the data analysis algorithm enhances user efficiency by reducing analysis time. In turn, this will reduce the amount of time clinical staff spend in reviewing the data. This is a unique advantage compared to devices which only collect data and produce an unedited, unformatted data stream in which correlations among categories of data are difficult, if not, impossible to discern.

In some embodiments, the data analysis algorithm can accept input about specific parameters that would be used in generating final reports. Customized targets can be set for different parameters such that the final report will contain an analysis that will indicate to what degree a specified target goal has been reached (for example, a target oxygen saturation during physical activity, or a target level of physical activity for a specified time interval). Graphical and numerical displays of summary trends are possible. For example, the user may want to determine how often a given patient actually walks during a specific time interval, including a determination of the amount of time spent walking (versus resting). Alternatively, the amount of time a target value of oxygenation is met or not met may be measured during a specified interval. Or, a composite analysis will be possible in calculating the amount of time a target value of oxygenation is reached during different types of physical activity, as in FIG. 4B. Or, it is well known that COPD patients develop nocturnal oxygen desaturation (NOD), or a decrease in oxygen saturation during sleep. The frequency, duration, and magnitude of NOD can be determined for each patient.

It is understood that this type of analysis can take several forms, including but not limited to bar graphs, pie charts, or other descriptive tabular representations of the data. The analysis can be performed over selected time intervals of a recording or the full recording. It is understood that a similar functionality exists for setting user-chosen target values for all parameters. Additional statistical analysis is possible, including but not limited to various forms of summation analysis in which marked events or intervals are summarized in terms of the frequency of events in all or part of the recording, or the magnitude of such events (for example, the magnitude of the decrease in oxygen saturation from a baseline value, as in FIG. 4F). This summation could take the form of counting the number of events or a calculation of the average change from baseline for a specific clinical parameter over a specified time interval. It is understood that other forms of summation are not limited to these examples.

It is understood that more complex data analysis is possible in which correlations among parameters may be done to provide a detailed analysis of the temporal profile of results (FIG. 4B or FIG. 4C). For example, data for physical activity and oxygenation may be analyzed together to generate reports correlating the level of oxygenation during different types of activity (rest, exertion, sleep) and whether specific targets for oxygenation during each activity are met. In this discussion, it is understood that "exertion" is defined as any physical activity that is not rest or sleep by specified criteria linked to the accelerometer activity count data. Further subdivisions of the exertion category are possible and not excluded by the above definition. The analysis of target values can take different forms. The degree to which a specific oxygenation goal has been met can be expressed as a percentage of the time for a type of physical activity ("% of the total time resting") or in units of time ("minutes of the total resting time"), as shown in FIG. 4B-E. It is understood that this functionality will also exist for the analysis of other combinations of parameters. Additional statistical analysis of data are possible and not excluded by these examples.

In some embodiments, additional data analysis capability is present that can accept input from the patient about their status during a recording. These patient inputs can include several general categories, such as "symptoms", "physical activity", "sleep", "nutrition", "medication usage", "LTOT usage", "social functioning", "medical interactions" followed by choices for each category. Custom categories can be created by the user. For accuracy, the patient can provide this input during the recording. The device can be programmed to accept such input prior to the initiation of the recording. One example of such input would be that the patient categorizes their level of shortness of breath ("dyspnea") using a recognized medical standard (Borg scale) designed for this purpose. Alternatively, the patient can provide a clarification of the nature of their activity at any moment during the recording or note any problems with the equipment that would be valuable to know during subsequent data analysis. Another example of patient input is a time-stamped indication of compliance (or lack of) with LTOT during a specific time interval. Another example is a patient notation about any problems during sleep or the quality of sleep. It is also understood that this is not a complete list of possibilities for patient categorization of their status during a recording. These patient inputs will be programmed to appear on a final report at the discretion of the user.

It is understood that in some embodiments sensors can be reprogrammed with new firmware or software, or that the timing and sampling rates of a sensor device can be individually set at the beginning of a recording.

In some embodiments, the device can record the presence of a oxygen source or delivery device on the patient. Detection of the presence of an oxygen source or delivery device or source is done thru an adapter/flow valve unit that is positioned in line between the oxygen source and the respiratory sensor. This can take the form of a time-stamped signal that is generated whenever an oxygen source or delivery device is detected by the CMU in the circuit coming from the adapter unit. This process can take the form of detecting a respiratory rate signal coming thru the adapter, rather than, or in addition to, through the respiratory sensor located near the patient's nose or mouth (e.g. illustrated in FIG. 1F, FIG. 2). In this manner, the time interval that the adapter is in use can be precisely determined during a recording. In some embodiments, patients do not activate the adapter generated signal of respiration if there is no oxygen source or delivery device connected to the adapter unit. Under these circumstances, there will be no signal detected coming thru the adapter. In this way, there can be a determination of the temporal profile of use of an oxygen delivery system which can provide an assessment of LTOT compliance and adherence to the LTOT prescription.

In some embodiments of the system and method described herein, the CMU is capable of detecting changes in the patient's level of oxygenation and adjusting oxygen delivery to the patient. The goal is to return the patient to an optimal level of oxygenation and avoid potentially harmful decreases in oxygenation ("hypoxemia") or wasteful administration of oxygen that is not cost-effective. This process can be initiated by the CMU as a signal to the adapter/flow valve unit that will modify oxygen liter-flow going to the patient. In one such embodiment, the signal can be based on the detection of a change in oxygen saturation from the appropriate sensor. This signal can be generated using an algorithm based on target values of oxygen saturation designated by the user. Detection of a decrease or increase in oxygen saturation below a designated target value will trigger a signal to the adapter/flow valve unit.

Alternatively, in another embodiment, the target values from more than one clinical parameter can be used to generate this signal in a more complex algorithm that would determine the rate of change of the selected parameters. Signals can be transferred either wirelessly or by directly to the adapter/flow valve unit that is interposed between the patient and the oxygen source or delivery system. The adapter can be configured to achieve compatibility with a large number of available oxygen delivery systems for LTOT currently on the market. In some embodiments, activation of the system can be controlled by the user who will have the option to either activate or deactivate this oxygen delivery algorithm before the initiation of a recording. In other embodiments, if a user changes the oxygen delivery algorithm in use, there can be a time stamped record which indicates the new setting (e.g. a change to a different oxygen delivery algorithm, or a change to a manual oxygen delivery method, or a change to a different oxygen delivery system (e.g. after failure or exhaustion of an oxygen delivery system). Typically, the user is a medical provider and/or another medical professional involved in the patient care involving the COPD monitor.

The adapter/flow valve functions by receiving control signals from the CMU with a scheme that uses one or more process algorithms Data gathered on one or more parameters (e.g. sensor measurements) can be used in a closed loop control system, such as for example, a proportional integral derivative (PID) loop control algorithm that uses the difference between the sensed values (feedback) versus the user-chosen optimal target values (set point, reference point, or reference value of the feedback loop, typically a closed loop) for these same parameters. A PID controller is a generic feedback mechanism that is widely used in industry for this purpose to control various processes. A PID controller calculates an error value that is the difference between the measured value of a parameter and the desired target value of that parameter. The controller works to minimize this error by an appropriate input into the system (e.g. control signal sent to the adapter/flow valve), such that the measured variable (a feedback parameter) is moved closer to the target value (a set point or reference value) and the "error" between the measured versus and target value of a parameter is minimized. This embodiment comprises a means of controlling the dose of oxygen that the patient receives and to initiate a change in oxygen liter-flow of oxygen transmitted to the patient. As will be appreciated by those skilled in the art, any other suitable control loop can be used such as a conventional P, PI, or PID control loop control method.

In one exemplary embodiment, blood oxygen saturation values can be used with a PID control algorithm as the sensed parameter of interest. The algorithm compares measured oxygen saturation of the patient to an optimal target value for oxygen saturation. The CMU uses the difference between actual and optimal values to generate a control signal that is transmitted to the adapter/flow valve unit that alters the oxygen liter-flow (either up or down) to the patient. One example of such a flow valve system uses a three-way, two position, solenoid-activated spool valve (Lee Company; West Brook, Conn.) connected in line between the oxygen source and the patient which can be used to change oxygen liter-flow in a graded fashion, dependent upon the size of the signal sent from the CMU to the adapter/flow valve. This type of algorithm is illustrated in FIG. 3. It is understood that for the purposes of this discussion, that blood oxygen saturation is the percentage of oxygen-saturated hemoglobin. It is understood that other algorithms are also possible and not excluded by this example.

As noted above, the PID controller algorithm can be configured to use input sensor signals for more than one clinical parameter, including but not limited to physical activity in the form of accelerometer output, energy expenditure, chest wall muscle EMG, respiratory rate, and heart rate in addition to oxygen saturation. The advantage of using these other parameters rather than oxygen saturation in the controller algorithm is the capability of more precise control over oxygen saturation in a patient than can be obtained compared with the use of oxygen saturation alone. This is because the changes in physical activity and/or chest wall muscle EMG that accompany exertion precede changes in oxygen saturation. This type of precise control of oxygen saturation is based on the capability to change oxygen liter-flow in anticipation of a significant decrease in oxygen content based on the trending of the one or more other clinical parameters in the algorithm. In this embodiment, if oxygen saturation is still at an acceptable target value, but the data from the sensors monitoring these other clinical parameters indicate that the patient is undergoing increased exertion manifested by either an increase in physical activity, chest wall muscle EMG, energy expenditure, respiratory rate, heart rate, etc, then a change in oxygen-liter flow can be initiated before oxygen saturation falls below the critical target value of 90%. This is a unique and novel method for regulating oxygen flow to the patient.

Specifically, in two exemplary embodiments, the CMU and the PID controller algorithm for the regulation of oxygen flow can be configured to use the input sensor signals comprising either the physical activity of the human subject or the signal from the chest wall muscles. This latter signal represents an electromyographic signal (EMG) from these muscles that is a surrogate for the neural output from the brain respiratory center to the muscles involved in breathing. This signal corresponds to the perception of breathlessness in human subjects and also correlates with the level of exertion of the subject [7]]. In this algorithm, the signals corresponding to physical activity and/or chest wall EMG will be major determinants utilized by the PID controller algorithm to generate the signal that modifies oxygen liter-flow thru the adapter/flow valve in accord with whether a chosen target value of oxygen saturation is met. In these embodiments, the parameter of oxygen saturation is not part of the algorithm that generates a signal to change oxygen liter-flow, but is only used as a target value to be met.

All data process algorithms include a means to detect invalid data, as outlined in FIG. 3, such that a baseline level of oxygen delivery continues in the presence of invalid data.

Finally, the PID loop algorithm can include of a means to generate an alarm signal composed of visual and/or auditory alerts when one or more parameters are out of range. The algorithm can, for example, generate a visual (LED display) and/or auditory alarm to alert the patient to the following exemplary events: 1) a drop in oxygen saturation below a target value (90% saturation) for >30 seconds; 2) a high respiratory rate (>30); 3) a pulse rate that falls out of a preset range (<60 or >120); 4) a visual display that LTOT is being used; or 5) an indicator that the patient is disconnected from their oxygen source if LTOT is in progress. It is understood that these examples of alarm functions do not limit the full range of potential alarms in other embodiments. It is understood that these alarm functions can be set to specific target values of these parameters other than the examples given above, or inactivated by user input before the start of a recording session.

In summary, the COPD system can provide feedback to the patient and provider as well as adjusting oxygen delivery to the patient's needs during activities of daily living based on the data obtained from measured clinical parameters (FIGS. 3-5). Oxygen delivery can be optimized during normal daily activities in the outpatient setting in two ways: 1) raising oxygen-liter flow to achieve target levels of oxygen saturation during exertion; or 2) reducing oxygen-liter flow when inappropriately high oxygen saturation levels are detected. In this fashion, a more cost-effective use of LTOT can be achieved while acceptable clinical criteria for oxygen delivery can be met. Such functional capability is an example of the unique features of the system and method described herein that illustrate its role as a new tool for clinical management of chronic lung disease.

All terms and expressions used are designed as terms of description, not limitation. There is no intention in the use of any term or expression of excluding equivalent features not shown and described or portions of features thereof. Overall, it is recognized that various modifications of the system and method described herein are possible within the overall scope of the system and method described herein. While particular embodiments of the system and method described herein have been illustrated above, it is further understood that the system and method described herein is not limited to the embodiments presented; numerous rearrangements, modifications, and/or substitutions are possible.

Various embodiments of a COPD monitor and control system for measuring, monitoring, and reporting human physiological data obtained in subjects with chronic lung disease while subjects are engaged in activities of daily living includes at least one sensor and in most embodiments, a plurality of sensor devices which include a means for the measurement of a plurality of clinical parameters, including at least an oximeter sensor measurement for monitoring oxygen saturation, multiple accelerometers for monitoring and quantifying the motion and movement associated with physical activity of the subject, a pedometer for monitoring steps taken by a subject, appropriate sensors to monitor energy expenditure, a respiratory rate or flow sensor or equivalent for monitoring the respiratory rate of the subject, a heart rate monitor, a blood pressure monitor, and sensors for chest wall muscle EMG (parasternal muscle electromyographic activity). It is understood that this plurality of clinical parameters represents just one possible embodiment of the type of parameters that can be measured. Other embodiments with different parameters or methods of measuring said parameters are possible.

The system also includes a central monitoring unit (CMU) that includes a microprocessor (or microcontroller) positioned inside a central housing unit worn on the body (typically, at the waist). This CMU can accept and monitor data input from each of the sensors, and send signals back to one or more sensors or other components following analysis of this sensor input. This unit also includes a means to organize or structure the incoming data from one or more sensors in accord with user-chosen or defined format choices at the beginning of a recording or later at the conclusion of a recording. This unit can analyze these data in a variety of user-specified formats for the purpose of producing reports for patient management, generating alarms if measured parameters are out of range of target values, or sending a signal back to one or more sensors or other components of the system to modify their function. The unit also includes a means of data storage for holding physiological data intact in retrievable form until downloaded to a remote computer workstation or equivalent.

The system also includes a data analysis process (e.g. one or more algorithms of a computer program (e.g. software, firmware, etc.) that runs on the CMU. Alternatively or additionally, the data analysis process can be performed on a remote computer workstation using the same computer process or different computer process. The CMU computer process includes a means to analyze, organize, format, and perform statistical analysis, and to summarize the physiological data obtained according to instructions from the user to create reports for patient management.

The system also includes an adapter and associated flow valve hereafter referred to as the adapter/flow valve unit that can send and receive a signal from the CMU, either simple or complex, that will then initiate a change in oxygen delivery (liter-flow of oxygen per minute) to the patient. The adapter/flow valve will typically be located in a circuit between the CMU and the patient's oxygen delivery unit or oxygen source (e.g. FIG. 1F). There can be either a "simple" (composed of a change in one parameter) control or "complex" (composed of a change in more than one parameter) control, of the flow valve either by wired or wireless means. It is understood that irrespective of whether this control of the adapter/flow valve is simple or complex, the control (e.g. a control signal) can be a graded signal that will vary in magnitude, as determined by a preset process composed of reference or user chosen target values for the parameters that generate the control signal. It is understood that the user can set or change the process, in terms of the choice of target values of the parameters, before a recording is initiated. In some embodiments, a lack of change in the parameters in the algorithm will generate no signal resulting in no change in oxygen delivery. Similarly, the largest defined change in all of the clinical parameters will generate the largest signal permitted based on the process algorithm chosen by the user. It is understood that the strength (e.g. magnitude or amplitude) of the flow valve control signal can vary between zero and the maximum signal permitted, such as, for example, based on a user-chosen format of choices for the data analysis algorithm that regulates oxygen delivery. There can be a linear relationship between the strength of the control signal and oxygen flow to the patient.

The method described herein is useful for monitoring the clinical parameters that are linked to clinical outcomes of patients with COPD, other chronic lung diseases, or medical equivalents. In some embodiments, the method includes the COPD monitor device, associated components, and data analysis algorithms under discussion that provide the basis for the creation of detailed clinical reports derived from the data obtained from monitoring of the clinical parameters in human subjects. Thus, in its various embodiments, the method includes the COPD monitor and components that accurately acquire, store, and format the physiological data representing the clinical parameters that are monitored during an outpatient recording, followed by the data analysis in user-chosen formats by the data analysis process algorithm (typically as software and/or firmware). This method will facilitate the objective of creating reports that can be used for disease management by medical professionals.

In some embodiments, the various sensor devices are part of a system and method adapted to collect physiological data on a continual basis, representing a plurality of clinical parameters as described herein above, during a recording from human subjects. The system can include a plurality of sensors which can measure at least one of the following parameters: blood pressure, heart rate, respiratory rate, oxygen saturation, physical activity, energy expenditure, and chest muscle EMG. The sensor devices can further include a means to generate physiological data on one or more of the specified clinical parameters noted herein above, and to transfer these data for storage and analysis to the central monitoring unit (CMU) using any suitable wired or wireless connection. The sensor devices can further include a means for affixing the devices to the human subject's body in a removable fashion to detect and record the physiological data signal related to the specific clinical parameters; and furthermore, be capable of collecting these data continuously while the human subject is performing normal activities of daily living. In some embodiments, a respiratory rate sensor is located on the patient's neck or arm, such as by using the technology of acoustic monitoring of the respiratory rate (Masimo, Irvine, Calif.), or any another sensing device or system suitable achieve a desired degree of accuracy in the detection of a change in this parameter and the clinical status of the human subject. In some embodiments, a compact, wireless pulse oximeter that is worn like a wrist watch for measurement of oxygen saturation is used. By such use of a compact, wireless pulse oximeter, the measured oxygen saturation values are collected from a sensor located in a plurality of locations, including but not limited to a distal extremity (finger of one hand), and then transferred to the CMU for storage and analysis using wireless technology such as is available from Nonin Medical Inc (Plymouth, Minn.; e.g. WristOx2 model 3150). In some embodiments, the use of one or more accelerometers can be used to determine the full spectrum and magnitude of body movement are used for measurement of physical activity. In some embodiments these accelerometers can be located within the CMU worn on the patient's body, typically at that patient's waist. In some embodiments, of the system the CMU receives and stores all physiological data from all sensors. In some embodiments, the system includes sensors for measurement of chest wall muscle EMG that represents the neural output of the central nervous system to the muscles involved in breathing in response to changes in the level of exertion of the subject.

In some embodiments, the system includes sensors for the measurement additional parameters (skin conductance measurement, thermoregulation measurement) which are used for the measurement of the clinical parameter of energy expenditure, as previously described [11]. The sensors for these measurements can be located in the CMU or at other optimal locations on the patient's body. It is understood that since the measurement of energy expenditure in human subjects is an evolving field, alternative approaches using different parameters for the calculation of energy expenditure are not excluded by the above example. It is understood that these combined data will be used for the final calculation of total energy expenditure. It is also understood that energy expenditure can be categorized according to a variety of schemes chosen by the user. For example, a common mode of presentation such data is to express a patient's energy expenditure in the form of a scale as follows: % of time in sedentary activities (less than 3MET), % of time in moderate physical activity (3-6 MET), or % of time in vigorous physical activity (>6MET). It is understood that other types of presentation of these data are not excluded by the above embodiment. It is also understood that the required computation for final presentation of these data will be done by the CMU data process algorithm (e.g. in software and/or hardware).

In some embodiments, the CMU (e.g. FIG. 1F, FIG. 2) includes a means for connecting to and receiving input from one or more sensors attached to the human subject's body or in any other location. The CMU also can include a means for sending signals to all sensors and other downstream components, including the adapter/flow valve used to regulate oxygen liter-flow. The CMU can include the data analysis process algorithm (e.g. in software and/or hardware) used for data analysis of physiological data received from the sensors during a patient recording, and creation of all final clinical reports used for disease management. In some embodiments, the sensors connect with a microcontroller located inside the CMU housing. Transmission of data from all sensors to the microcontroller can occur via a direct physical connection by any suitable connectivity means, including, for example, RS232, USB port or equivalent, or alternatively, data transfer can occur via any suitable wireless type connections, including Bluetooth or any other suitable RF transfer method. It is understood that since forms of wireless data transmission are constantly evolving and changing, alternative forms of wired and wireless transmission at any suitable wavelength in the electromagnetic spectrum are not excluded by these examples. In some embodiments, the CMU and its components receive physiological data from the sensors as described herein. The CMU housing includes a means for attachment to the human subject's body such that the subject is capable of performing all daily activities of living in a normal fashion without disrupting data capture and transmission to the CMU. In some embodiments, the CMU includes a means for initiating the start and termination of an ambulatory patient recording, including, for example, a specified time interval during which the collection of physiological data from a human subject is in progress. In some embodiments, the CMU includes a means for marking or time-stamping the recording at any time point during the recording by the patient for the purpose of identifying the time of specific events of significance. The time-stamp can also occur following completion of the recording during data analysis and review by the user. In some embodiments, the CMU includes a means for visually displaying a plurality of information related to the recording of physiological data, including a least one of the following: elapsed time of the recording, remaining battery power, remaining memory capacity, status of connection of the sensors to the CMU, status of any connection of a patient oxygen source or delivery unit to the adapter/flow-valve unit, and state of function of all sensors.

In some embodiments, the CMU includes a means for storage of data in a user-specified format. It is understood that as memory and storage capacity continues to develop and increase rapidly, the upper limit of storage capacity may also increase. In some embodiments, the CMU includes a means for communicating with a remote computer workstation for transmission of physiological data at the completion of a recording. This transmission of data may be either by physical connection, or comprised of one or more wireless connections. In other embodiments, the data transfer can include a means of transfer to a specific internet website designated by the user. In some embodiments, the CMU includes a means for communicating with other sensors and the adapter flow-valve unit located within the CMU and/or in close proximity therein for the purpose of data transmission, data storage, and signal transmission during a recording. In some embodiments, the CMU includes a means to perform data transfer whenever this unit detects a suitable download destination by whatever data transfer mode or route is currently activated. This download data destination may comprise a remote computer workstation or a designated internet site chosen by the user.

In some embodiments, the CMU is configured to control the adapter/flow valve (e.g. by sending a "signal" thru an interface device, referred to as an "adapter", or to control the flow valve by any other suitable microcomputer/flow valve interface). Such control of the flow-valve results in a change in oxygen delivery by modifying the oxygen-liter flow delivered by the patient's oxygen delivery unit or oxygen source to the patient. It is understood that a change in the setting for oxygen delivery includes a change in the liter-flow/min of oxygen as controlled by the adapter/flow valve unit. The CMU control of the adapter/flow-valve unit can be accomplished by use of a PID loop control process algorithm that can run on the CMU. Such loops can use the difference between actual measured values of one or more selected parameters at a point in time and the desired optimal target value or reference values of these same parameters. In some embodiments, the process algorithm uses the difference between measured oxygen saturation in a human subject and the optimal target value of oxygen saturation to generate this proportional signal. It is understood that this proportional signal will result in a linked proportional change in oxygen liter-flow per minute delivered to the patient. It is understood that additional process algorithms, as described herein, are possible that can make use of the difference between measured versus optimal target values of more than one clinical parameter at the discretion of the user.

In some embodiments, the CMU includes a means to sense whether the patient is wearing an oxygen source or oxygen delivery unit, and whether this unit is connected to the system described herein. In some embodiments, the respiratory sensor plays an important role in determining the presence of this connection (or not) by registering an air flow signal emanating from within the adapter/flow-valve unit. If airflow from the adapter/flow valve unit is detected, the CMU can include a means to time-stamp the time of attachment and record the length of time that this connection continues to exist. It is understood that when the patient's oxygen source or delivery unit is disconnected from the COPD monitor, the CMU can detect a lack of air flow coming from the adapter/flow valve unit (e.g. a detected oxygen supply failure) in this same sensor that will generate a time-stamped signal that also registers this event. It is understood that this set of events (e.g. any detected system fault, control loop failure, or microcomputer failure), such as detecting a connection or disconnection of the unit with time-stamped signals, is a standard feature of connecting the COPD monitor and its adapter/flow valve unit to a patient's oxygen source or delivery.

In some embodiments, the CMU includes a means to measure one or more signals from one or more sensors for the purpose of generating a running average of the magnitude of each of the signals from one or more sensors (e.g. a combination of two or more sensor measurements). In some embodiments, CMU includes a means to compare the running averaged values from the one or more sensors to one or more specific baseline normal target values or so-called "normal" values of these same signals from each sensor. These normal or target values will be chosen, entered, and set at the beginning of the recording by the user prior to initiation of a recording. In some embodiments, the CMU microcontroller includes a means to compare the averaged signals from one or a plurality of sensors and calculate the magnitude of how much the measured signal differs from the normal target value of each signal (e.g. a measured sensor value). In one such embodiment, the predetermined amount of allowable difference is defined as a magnitude of difference that is equal to or less than two times the standard deviation of the normal target value for each signal. Alternatively, a predetermined amount of difference can be entered manually into the CMU before a study begins and used in all subsequent calculations and comparisons. Alternatively, the CMU can include means for using additional statistical methods that measure the variability of clinical parameters over time for calculating the magnitude of the difference from normal target values of each parameter.

In some embodiments, the CMU includes a means to calculate a predetermined amount of difference from the baseline normal value of one or more signals from all sensors. The CMU uses this magnitude of difference to initiate a change in oxygen liter-flow per minute received by the patient, either an increase or decrease by a specified amount, using a predetermined process algorithm. This algorithm for a change in oxygen liter-flow is based on the magnitude of the change, either an increase or decrease, in the allowable difference from an averaged value of all signals used in the process algorithm. It is understood that the calculations of the variability or amount of difference from the baseline normal value of one or more sensor signals can use other statistical measures, including but not limited the root mean squares of successive differences among measured values of a given parameter over a specified time interval. Other statistical methods of the allowable amount of difference from the averaged value are not excluded by this example.

In some embodiments, the CMU can initiate a change in oxygen liter-flow using a formula that is linearly related to the magnitude of difference from the normal target value of one or more signals from selected sensors (e.g. a combination of two or more sensor measurements), for example, only when the magnitude is either greater than or less than two times the standard deviation of the normal target value for each signal. It is understood that this is only one possible method for initiation of a change in oxygen liter-flow, and that other possible formulations are not excluded. In some embodiments, the CMU includes a means to prioritize which measured differences between normal target values and measured values of different parameters are used to initiate a change in oxygen flow. In one such embodiment, this prioritization can take the form of determining before the initiation of a recording which signals from a plurality of sensors will be used to generate or initiate a change in oxygen flow.

It is understood that more than one prioritization scheme may be set prior to the start of a recording by choosing a different set of sensor signals that will participate in this prioritization process. The prioritization scheme itself can take the form of "if/then" statements in hardware, firmware, and/or software in which changes in more than one sensor-derived signal (measured parameter) are processed according to a scheme set by the user before the start of a recording. For example, if chest wall muscle EMG, physical activity, respiratory rate, and pulse rate are chosen before the start of a recording as prioritization parameters, then this preset prioritization scheme will determine which parameter is acted upon first in initiating a change in oxygen liter-flow. If there is no change in the "first" priority parameter, then the algorithm moves to the second priority parameter to determine if a difference in the measured values is present to justify a change in oxygen liter-flow. The prioritization algorithm will continue until all signals have been analyzed and processed.

The CMU includes a means to continually repeat a procedure, for example, every five seconds as long as the predetermined difference of a measured signal from one sensor or a group of sensors exceed an allowable magnitude, compared to normal target values for the measured parameters.

In some embodiments, the CMU and adapter/flow-valve system include a means to modify oxygen delivery, as discussed hereinabove, by recognizing the inspiratory phase of respiration in the human subject, and timing changes in the signal to modify oxygen liter-flow to the inspiratory cycle of respiration only. In some embodiments, a corollary of this principle is that no change in oxygen liter-flow will be initiated during the expiratory phase of respiration. In some embodiments, demographic characteristics (sex, age, weight, height) can be entered and stored in the CMU at the start of a recording.

In some embodiments, the system includes a CMU that communicates with an adapter and flow valve that is located in the gas circuit linking the COPD monitor with a patient's oxygen delivery unit or oxygen source. Specifically, the adapter/flow valve is located in this circuit between the oxygen delivery unit and the nasal cannula that delivers oxygen to the patient (FIG. 2, FIG. 3). The adapter includes a means to receive control signals on an ongoing basis from the CMU and send signals to the closely positioned flow-valve on a continual basis so that this valve can be controlled from open or closed in varying degrees to initiate a change in oxygen liter-flow to the patient (i.e. to control the oxygen liter-flow to the patient). For the purposes of this description, the adapter and flow-valve are considered one unit.

In some embodiments, the control signal sent from the CMU to the adapter/flow valve is a composite summary signal of the changes in the values of one or more parameters continuously measured by the sensors-according to the aforementioned prioritization scheme of parameters noted above.

When the COPD monitor is connected to a patient with an oxygen delivery device in use, a time-stamped signal is generated that indicates on the patient recording when this connection occurred and that an oxygen delivery system has been detected and is on-line. This signal or indication can continue as long as the connection is maintained. It is understood that the time-stamped signal serves as a marker of the use of an oxygen delivery system by the patient that can be used to determine the interval of time, and thus, the degree of compliance with LTOT while the patient is linked to the COPD monitor.

In some embodiments, the adapter receives a control signals from the CMU (e.g. from the CMU), either by a direct physical connection or by any suitable wireless means. The adapter initiates a change in oxygen delivery in the form of a change in liter-flow/min of oxygen to the patient via the closely associated flow-valve. It is understood that the adapter/flow valve unit will be comprised of universal features, such that it will achieve compatibility with a large number oxygen delivery units or oxygen sources currently available.

In some embodiments, the CMU and the adapter/flow valve can work in a coordinated way, including a new use function that regulates the oxygen delivery to the patient in response to changes in physiological data (e.g. data collected by the various sensors representing the continuously monitored clinical parameters). Such a new use function can include a means to use a form of PID (proportional-integral-derivative controller) algorithm, such as is illustrated in FIG. 3A and FIG. 3B, according to the following steps: 1) physiological data representing different clinical parameters is collected from the sensors and analyzed at the level of the CMU; 2) generation of a control signal by the CMU, based on use of the PID algorithm that detects a significant deviation from normal in one or more target values of one or more of the measured clinical parameters; 3) the control signal for modulation of oxygen-flow is sent to the adapter/flow valve; 4) based on the control signal, the adapter changes the flow valve position to produce a change in oxygen liter-flow going to the patient; 5) repeat cycles of this type of interaction between the microcontroller and adapter/flow valve unit occur continuously with adjustments made whenever defined levels of deviation from normal target values of the selected parameters are detected by the microcontroller.

This time interval of 5 seconds represents one embodiment, but it is understood that the time interval upon which this average value is calculated can be changed or varied as needed (e.g. in some embodiments over a range of one second→60 seconds).

In some embodiments, the CMU calculates the degree of deviation of the value of a clinical parameter from a set target value over a specific time interval for each parameter using a form of PID loop algorithm. The parameters can include one or more of the following: respiratory rate, heart rate, physical activity, energy expenditure, chest wall muscle EMG, and/or oxygen saturation. It is understood that different embodiments may use a different set of parameters for this purpose, and that there are no limitations on the type or number of clinical parameters that may be used for these calculations.

In some embodiments, the CMU uses a preset PID data analysis algorithm, also referred to as a plurality of adjustable coefficients that employ user-selected target values for each clinical parameter, to determine if the average values of each parameter during each measurement deviate significantly from the chosen normal target values of each parameter. It is understood that the term "deviate significantly" can vary, and include changes, for example, from the baseline of a specific clinical parameter from 1-20%. It is understood that the user will typically set this deviation level from baseline at the start of a recording period and that this level of deviation from selected target values will be applied for the entire recording interval.

For example, when a closed loop process control detects a deviation from normal target values of one or more clinical parameters over a predetermined threshold, there can be a graded increase in control values transmitted to the adapter/flow valve. It is understood that different graded scales of signal strength magnitude are possible and not excluded in different embodiments of this algorithm.

In some embodiments, following a change in oxygen flow, the data analysis algorithm can resample at a specified interval (e.g. range of 1-60 seconds) parameters, used to initiate a change in oxygen liter-flow, in order to determine if the measured values of these parameters have returned to their normal target values, or whether additional changes in oxygen delivery are warranted. This determination can be done with different mathematical models, including but not limited to a recursive least squares optimization method. If a return to equilibrium has occurred, no further change in oxygen flow will be initiated. If a return to equilibrium has not occurred, a new signal to the adapter/flow valve is generated by the CMU. This pattern of assessment can continue with a new cycle of change in oxygen liter-flow until the measured parameters return to the normal range of values set by the user.

In some embodiments, data analysis referred to here as the data analysis process (e.g. one or more algorithms in hardware, software, and/or firmware) located in the CMU includes a means for processing physiological data representing the clinical parameters obtained from the sensors. This data analysis process can analyze and format the data obtained from the recording to the user's specifications. The data analysis process culminates in the production of clinical reports that are used by medical providers for patient management decisions. In some embodiments, the analysis process includes the following components:

A data analysis process includes a computer-readable program contained within the CMU. The process algorithm includes a computer-readable program code executable by a computer processor. Alternatively, the processor that runs the data analysis process can be either a remote computer workstation, hand-held PDA-like device, or a cloud-based internet site that is used for data analysis after the completion of a recording. Thus, it is understood that all or some of the data analysis capabilities of the data analysis process can be transferred ("downloaded") to other sites and/or hardware (local or remote, e.g. elsewhere on via a network such as, for example, the Internet) for continued data analysis following completion of a recording. The output of the readable program code, including formatted (graphical or tabular) reports can be transferred using standard computer-usable storage media, all having a humanly sensible output;

A data analysis process can include a means of transferring physiological data representing clinical parameters acquired from a recording of a human subject to a computer workstation. The transfer can include a direct connection or by any suitable wireless connection.

A data analysis process can include a means for transfer and storage of the acquired data from recordings of human subjects on a computer-readable storage medium.

A data analysis process can include a means to format the final output in specific user-defined ways to create reports for use in clinical disease management. In some embodiments, these reports can be formatted to demonstrate the temporal profile of results with one or more of the measured clinical parameters. It is understood that multiple formats for data analysis are possible. For example, in some embodiments, a graphical illustration of the temporal changes in oxygen saturation during each category of physical activity can constitute one type of format for a clinical report that can provide information for patient management (e.g. as shown in FIG. 4A). It is understood that other types of tabular or graphical illustration of results involving other parameters are not excluded by this example. Another example would be the comparison of the temporal profile of results for one or more clinical parameters in one patient between different recordings (e.g. as shown in FIG. 5A, FIG. 5B). A comparison of one or more parameters among recordings of different patients is another possible analysis format (FIG. 5C). It is understood that the examples given above do not encompass the full range of data analysis possibilities; other possibilities are not excluded by the above examples.

A data analysis process can include a computer-readable program located within the CMU such that the computer-readable program code is executable by a computer processor, and capable of performing a plurality of mathematical functions related to analyzing the physiological data acquired by sensors as described herein above.

A data analysis process can include a computer logic circuit or computer program, configured to retrieve information from a specific file containing the data acquired from the plurality of one or more sensors, and perform a plurality of statistical analysis functions using a plurality of mathematical formulas, on the physiological data acquired from the recordings of human subjects, according to the instructions of the user;

A data analysis algorithm can perform a plurality of statistical analysis functions specified by the user, such that the raw data from one or more clinical parameters may be summarized in a variety of ways over the whole recording or any specified time interval of the recording, including but not limited to the following: mean average value of one or more clinical parameters, the duration of time one or more parameters are outside of user-specified target values for each parameter, the magnitude of change from a specified target value of same clinical parameters, or a comparison of the values for one or more parameters among different specified time intervals of the whole recording. For example, for the parameter of physical activity, the algorithm can determine the duration in minutes or hours of different types of physical activity (rest, exercise, sleep) over the course of the entire recording or selected time intervals of the recording. It is understood that additional types of data summary or comparisons are possible and not limited to the examples above. It is understood that more complex types of analyses are also possible, including the simultaneous analysis of two selected clinical variables over selected time intervals. In the latter example, this could take the form of determining the percentage of time oxygenation was at acceptable levels (>90% oxygen saturation) during each different category of physical activity (rest, exercise, sleep) as is illustrated in FIG. 4B. Other types of complex analysis are not excluded by this example.

A data analysis algorithm can display the results of a statistical analysis of physiological data in a plurality of graphic or numerical forms that are specified by the user. This display may include, but is not limited to frequency distributions, bar graphs, or formatted time charts of the data of one or more clinical parameters from a patient recording. It is understood that other types of displays are not excluded by these examples.

A data analysis algorithm can summarize the temporal profile of results for each parameter using a plurality of statistical functions chosen by the user. It is understood that these mathematical operations can be done for the whole recording or specified intervals of the recording at the discretion of the user. It is understood that these data summaries will be composed of, but not limited to, basic measures of variability, including a standard deviation and standard error wherever a mean value of physiological data is obtained, and the frequency distribution of the measured values. It is understood that other statistical approaches are not excluded by these examples.

A data analysis algorithm can count the number of selected events in a recording over the entire recording time or a time interval specified by the user. Furthermore, it is understood that the total counts of events for a specific parameter can be expressed in a final report at the user's discretion. For example, the user may specify that the number of "hypoxic events" during the recording are counted with the event defined as all periods in the oximetry tracings that have an oxygen saturation <90% over a specified interval as shown in FIG. 4F. In this same example, the user can also specify that the total duration (in minutes) of these events be measured and summarized Finally, the user can specify that the magnitude of these events is categorized with user-specified criteria, including the following: the number of events with a <5% decrease from baseline oxygenation, the number of events with a 4-10% decrease from baseline, or the number of events with a >10% decrease from baseline, as in FIG. 4F. Thus, in this example, a "hypoxemia profile" can be determined which is comprised of the number of such events, the total length of time oxygenation is below acceptable values in each "hypoxemia" category, and a profile of the magnitude or severity of these events in each "hypoxemia" category.

In some embodiments, the method includes steps of generating a clinical report, as illustrated in FIG. 4A, that shows one type of exemplary report generated by COPD Monitor system and method that illustrates the temporal profile of physical activity (rest, exertion, and sleep) in a hypothetical patient with chronic lung disease for one 24-hour period. The generation of this clinical report is comprised of the following steps:

collection of physiological data from one or more sensors that monitor the physical activity of the patient;

detailed analysis of these time-stamped data such that all data are categorized as belonging to a specific activity category (rest, exercise, sleep);

further detailed analysis of these time-stamped data such that the amount of time spent by the patient in each category of physical activity is determined for a specified interval of the recording period or the whole recording period; this analysis of time spent in each category of physical activity is displayed as either actual time in minutes or a percentage of the total activity time for the recording;

display of the cumulative total of each activity type of the data analysis noted above in either a graphic (as shown in FIG. 4A) or tabular form that can be used by a medical professional for disease management.

In some embodiments, the method includes steps of calculating a time in minutes of each predominate activity type or a percentage, further comprising the step of calculating a time profile of oxygenation for each predominate activity type where oxygen saturation falls below 90% oxygen saturation, and wherein said step of displaying comprises displaying said actual time in minutes where oxygen saturation falls below 90% of each predominate activity type or said percentage of the total activity time where oxygen saturation falls below 90% of each predominate activity type.

In some embodiments, each category of physical activity is determined for a specified interval of the recording period or the whole recording period; specifically, the amount of time spent below 90% oxygen saturation (% time<90% saturation) is calculated for each category of physical activity as either actual time in minutes or the percentage of time that oxygen saturation was <90 saturation for a specified interval of the recording or the whole recording period. A time in minutes of each predominate activity type or a percentage of the total activity time of each predominate activity type, and wherein said step of displaying comprises displaying said actual time in minutes of each predominate activity type or said percentage of the total activity time of each predominate activity type.

In some embodiments, the method includes steps of steps of generating a clinical report, as illustrated in FIG. 4B, that shows one type of exemplary report generated by the COPD Monitor system and method that illustrates the temporal profile of oxygenation and physical activity in a hypothetical patient with chronic lung disease for a 24-hour period. The generation of this clinical report is comprised of the following steps:

collection of physiological data from one or more sensors that monitor the oxygenation and physical activity of the patient simultaneously;

detailed analysis of these time-stamped data such that all the oxygenation data are categorized as belonging to a specific activity category (rest, exercise, sleep);

further detailed analysis of these time-stamped data such that the profile of oxygenation for each category of physical activity is determined for a specified interval of the recording period or the whole recording period; specifically, the amount of time spent below 90% oxygen saturation (% time<90% saturation) is calculated for each category of physical activity as either actual time in minutes or the percentage of time that oxygen saturation was <90 saturation for a specified interval of the recording or the whole recording period;

display of the cumulative total of the data analysis steps noted above in either a graphic or tabular form (as shown in FIG. 4A) that can be used by a medical professional for disease management;

In some embodiments, the method includes steps of generating a clinical report, as illustrated in FIG. 4C, that shows one type of exemplary report generated by the COPD Monitor system and method that illustrates a quantitative temporal profile of oxygenation and physical activity in a hypothetical patient with chronic lung disease for a 24-hour period. The generation of this clinical report is comprised of the following steps:

collection of physiological data from one or more sensors that monitor the oxygenation and physical activity of the patient simultaneously;

detailed analysis of these time-stamped data such that all the oxygenation data are categorized as belonging to a specific activity category (rest, exercise, sleep);

detailed analysis of these time-stamped data for physical activity such that the duration of each category of physical activity is calculated for a specified interval of the recording or the whole recording as either actual time in minutes or a percentage of time of the whole recording;

detailed analysis of these time-stamped data for both oxygenation and physical activity such that the amount of time spent below 90% oxygen saturation (% time<90% saturation) is calculated for each category of physical activity for either a specified interval of the recording period as either actual time in minutes or a percentage of time of a specific activity category;

display of the cumulative total of the data analysis steps noted above in either a graphic or tabular form (as shown in FIG. 4C) that can be used by a medical professional for disease management;

In some embodiments, the method includes steps of generating a clinical report, as illustrated in FIG. 4D, that shows one type of exemplary report generated by the COPD Monitor system and method that illustrates the determination of the efficacy of a LTOT (Long Term Oxygen Therapy) prescription, including patient compliance with this prescription, in a hypothetical patient with chronic lung disease for a 24-hour period. The generation of this clinical report is comprised of the following steps:

collection of physiological data from one or more sensors that monitor the oxygenation, physical activity, and patient compliance with an oxygen delivery system simultaneously;

detailed analysis of these time-stamped data such that all the oxygenation data and patient compliance data are categorized as belonging to a specific activity category (rest, exercise, sleep);

detailed analysis of these time-stamped data for physical activity such that the duration of each category of physical activity is calculated for a specified interval of the recording or the whole recording as either actual time in minutes or a percentage of time of the whole recording;

detailed analysis of these time-stamped data for patient compliance such that the duration of patient compliance (and non-compliance) are recorded and calculated for specific intervals of the recording or the whole recording as either time in minutes or a percentage of time of the whole recording; specifically, the periods of noncompliance will be calculated for each different physical activity category;

display of the cumulative total of the data analysis steps noted above in either a graphic or tabular form (as shown in FIG. 4D) that can be used by a medical professional for disease management;

In some embodiments, the method includes steps of generating a clinical report, as illustrated in FIG. 4E, that shows one type of exemplary report generated by the COPD Monitor system and method that illustrates the determination of the efficacy of an oxygen delivery device in a hypothetical patient with chronic lung disease for a 24-hour period. The generation of this clinical report is comprised of the following steps:

collection of physiological data from one or more sensors that monitor the oxygenation, physical activity, and patient compliance with an oxygen delivery system simultaneously;

detailed analysis of these time-stamped data such that all the oxygenation data and patient compliance data are categorized as belonging to a specific activity category (rest, exercise, sleep);

detailed analysis of these time-stamped data for physical activity such that the duration of each category of physical activity is calculated for a specified interval of the recording or the whole recording as either actual time in minutes or a percentage of time of the whole recording;

detailed analysis of these time-stamped data for patient compliance such that the duration of patient hardware compliance (and non-compliance) are recorded and calculated for specific intervals of the recording or the whole recording, as either time in minutes or a percentage of time of the whole recording; specifically, the periods of noncompliance will be calculated for each different physical activity category as either time in minutes or a percentage of time for each different physical activity category;

display of the cumulative total of the data analysis steps noted above in either a graphic or tabular form (as shown in FIG. 4E) that can be used by a medical professional for disease management;

In some embodiments, the method includes steps of generating a clinical report, as illustrated in FIG. 4F, that shows one type of exemplary report generated by the COPD Monitor system and method that illustrates the determination of the frequency, duration, and magnitude of hypoxemic events in a hypothetical patient with chronic lung disease for a 24-hour period. The generation of this clinical report is comprised of the following steps:

collection of physiological data from one or more sensors that monitor the oxygenation and physical activity of the patient simultaneously;

detailed analysis of these time-stamped data such that all the oxygenation data are categorized as belonging to a specific activity category (rest, exercise, sleep);

detailed analysis of these time-stamped data for physical activity such that the duration of each category of physical activity is calculated for a specified interval of the recording or the whole recording as either actual time in minutes or a percentage of time of the whole recording;

detailed analysis of these time-stamped data for oxygenation such that the number, average duration, and magnitude of hypoxemic events are recorded; the number of hypoxemic events is defined as the number of events in which oxygen saturation decreases to <90% saturation during the recording period; the average duration of hypoxemic events is defined by the average length of time in minutes that oxygen saturation decreases to <90% saturation; and the magnitude of hypoxemic events is defined by using user set criteria; in this example, hypoxemic events were classified into three categories: <4% decrease below 90% saturation, 4-10% decrease below 90% saturation, and >10% decrease below 90% saturation;

display of the cumulative total of the data analysis steps noted above in either a graphic or tabular form (as shown in FIG. 4E) that can be used by a medical professional for disease management.

In some embodiments, the method includes steps of generating a clinical report, as illustrated in FIG. 5A, FIG. 5B, that shows one type of exemplary report generated by COPD Monitor system and method that illustrates cumulative trends and summary statistics in the data obtained from a recording; in this example, the cumulative trend and summary statistics are illustrated and compared between two or more 24-hour monitoring periods in the same patient for the following variables: vital signs, physical activity, energy expenditure, oxygenation, and the temporal profile of oxygenation during each activity category in a hypothetical patient with chronic lung disease. The generation of this clinical report is comprised of the following steps:

collection of physiological data from one or more sensors that monitor the vital signs (respiratory rate, blood pressure, heart rate), physical activity, energy expenditure, oxygenation profile, and % time oxygenation was <90% saturation during each activity category in the patient over two or more separate 24-hour monitoring periods simultaneously;

detailed analysis of the time-stamped data for the variables noted above (vital signs, physical activity, energy expenditure, oxygenation profile, and % time oxygenation was <90 saturation) such that all the oxygenation data are categorized as belonging to a specific activity category (rest, exercise, sleep); significant abnormal oxygenation values any of the activity categories are typically highlighted in yellow (highlight not shown in FIG. 5A);

detailed analysis of the oxygen profile data from each recording such that the oxygenation profile for each activity category are calculated for comparison between the two 24-hour recording periods (illustrated in FIG. 5B); significant abnormal oxygenation values for each activity category in both 24-hour recordings are highlighted (yellow);

display of the cumulative total of the data analysis steps noted above in either a graphic or tabular form (as shown in FIG. 5A) are illustrated that can be used by a medical professional for disease management.

In some embodiments, the method includes steps of generating a clinical report, as illustrated in FIG. 5C-D that shows one type of exemplary report generated by COPD Monitor system and method that illustrates cumulative trends and summary statistics in the data obtained from one or more 24-hour recording periods; in this example, the cumulative trend and summary statistics are illustrated and compared between two or more 24-hour monitoring periods in the same patient for the following variables: overall compliance with LTOT (long-term oxygen therapy) and the average oxygenation during the both the periods of compliance and non-compliance with LTOT during each 24-hour recording, and the overall range of compliance per day (low vs high) during all monitored 24-hour intervals (FIG. 5C), and each activity category on each 24-hour monitoring period (FIG. 5D) in a hypothetical patient with chronic lung disease. The generation of this clinical report is comprised of the following steps:

collection of physiological data from one or more sensors that monitor total compliance with LTOT over any given 24-hour recording period, oxygenation during periods of compliance and noncompliance with LTOT, physical activity during each 24-hour recording period, and oxygenation profile during each activity category in the patient over two or more separate 24-hour monitoring periods simultaneously;

detailed analysis of the time-stamped data for the variables (total compliance with LTOT, oxygenation during periods of compliance and noncompliance with LTOT activity) such that the total compliance with LTOT (minutes) over all 24-hour recording periods and the oxygenation during periods of LTOT compliance and noncompliance over these same recording periods are calculated; significant abnormal average oxygenation values for any 24-hour recording period, or abnormal oxygenation values during periods of LTOT compliance or noncompliance are highlighted (as illustrated in FIG. 5C typically in yellow, color not shown in FIG. 5C);

further detailed analysis of the time-stamped data for the variables (total time in minutes that oxygenation was >90% saturation, and % time oxygenation was <90 saturation during each activity category) for each 24-hour recording period are calculated; significant abnormal average oxygenation values for any 24-hour recording interval or any of the activity categories for any specific 24-hour recording period are highlighted (as illustrated in FIG. 5D, typically in yellow, color not shown in FIG. 5D);

display of the cumulative total of the data analysis steps noted above in either a graphic or tabular form (shown in FIG. 5C-D) that can be used by a medical professional for disease management.

In some embodiments, the method includes steps of generating a clinical report, as illustrated in FIG. 5E that shows one type of exemplary report generated by COPD Monitor system and method that illustrates a type of report that displays cumulative trends and summary statistics in the data obtained from a recording; in this example, the cumulative trend and summary statistics are illustrated and compared between two 24-hour monitoring periods in different patients with chronic lung disease for the following variables: vital signs, physical activity, energy expenditure, oxygenation, and the temporal profile of oxygenation during each activity category. The generation of this clinical report is comprised of the following steps:

collection of physiological data from one or more sensors that monitor the oxygenation profile during a specified activity category over specified intervals of a 24-hour recording from one or more different patients;

detailed analysis of the time-stamped data for the oxygenation profile for a specified activity category (rest, exertion, sleep), such that the variables of % time that oxygen saturation was <90% for a specified interval of each recording from one or more different patients are calculated and displayed for comparison;

display of the cumulative total of the data analysis steps noted above in either a graphic or tabular form (as shown in FIG. 5E) that can be used by a medical professional for disease management It is understood that the data analysis process algorithms can have additional capabilities for statistical analysis and summation of data trends that will facilitate data summary and generation of user-specified clinical reports.

A computer readable non-transitory storage medium as non-transitory data storage includes any data and/or program process code (e.g. algorithms or processes) stored on any suitable media in a non-fleeting manner Such data storage includes any suitable computer readable non-transitory storage medium, including, but not limited to hard drives, non-volatile RAM, SSD devices, CDs, DVDs, etc. Typically, microprocessor program code (e.g. computer readable code, software, and/or firmware) and/or acquired and/or recorded data is stored in non-volatile memory.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

Summary: Rationale for the System and Method described herein: Despite the addition of new antibiotics, bronchodilators, and anti-inflammatory drugs to the medical provider tool kit, little has changed in the overall approach to chronic lung disease in the past several decades. Disease management remains almost exclusively confined to the inpatient or clinic setting where patients and providers interact. Disease management largely remains a passive rather than active process in which a patient develops symptoms of illness in the outpatient setting that prompts consultation with a provider. There is little or no pro-active monitoring, including data acquisition on patients in the outpatient setting, that can be used by medical professionals and incorporated into chronic disease management. A more proactive approach is needed.

The advantage of such an approach is that the clinical and functional status of a patient can be monitored in real time by medical professionals with parameters that are recognized as important for the long-term management of patients with chronic lung disease. This approach is very different from models in which a human subject or patient engages in self-management, using a device that may generate large amounts of data that are unlikely to be reviewed and interpreted by a medical professional. Data streams are not a substitute for effective disease management. A self-management approach is not appropriate for many patients, especially the elderly, who cannot interpret such data. The self-management approach is also a poor substitute for the monitoring of the clinical status of a patient by a medical professional. At the medical provider level, providers are struggling in the real world of day to day medical practice with limited time to improve the quality of patient care. Many problems related to ineffective patient assessment can be reduced or eliminated with use of the system and method described herein. A targeted use of the present method and system described herein that exemplify this proactive approach to disease management in individual patients by medical professionals is a powerful answer to the concern about the proliferation of devices that measure bodily functions in the outpatient setting with little or no input from a medical provider. A better solution is to put the system and method that will facilitate disease management in the hands of the provider, as noted below.

Therefore, the system and method described herein monitoring substantially in real-time, has advantages for both providers and patients with chronic lung disease. A recent review noted that a high priority should be given to interventions aimed at delaying progression of disease, preventing exacerbations, and reducing the risk of comorbidities to eliminate the clinical and economic burden of disease [4,5, 6]. This is an accurate description of the rationale for using the system and method ("COPD Monitor") described herein.

This system and method is intended to be used by medical providers as a tool for chronic lung disease management (or medical equivalent). The acquired data is the basis for generation of clinical reports generated in user-chosen formats. This functionality is part of a new paradigm of chronic lung disease management that is patient-specific and based on data obtained while patients are engaged in activities of daily living. This type of disease management is not part of standard medical practice in patients with chronic lung disease at this time. This approach will provide information that would otherwise remain unavailable to the provider without the deployment of the system and method described herein.

All patients with chronic lung disease may benefit from this approach, specifically patients who require an individualized exercise prescription, participation in a pulmonary rehabilitation program, or delivery of LTOT in the outpatient setting. It is uncommon in medical practice that data acquired in the outpatient setting where patients live, work, and engage in activities of daily living is then used for disease management. The system and method described herein is specifically designed for this purpose. This new clinical tool is designed to facilitate the management of chronic lung disease (or medical equivalent), and reduce the frequency of disease exacerbations and hospital admissions. COPD Treatment, Long-Term Oxygen Therapy (LTOT), and Long-Term Management:

Before describing the system and method in more detail, the discussion of COPD and related problems begun herein above is continued so that the problems of COPD treatment and long-term management can be better understood. Also, with more explanation of problems related to COPD and chronic disease management, it will be appreciated there is a long-felt need for a system and method for the assessment of key clinical parameters of patients with chronic lung disease based on data acquisition while patients are engaged in normal activities of daily living. This approach is not the current standard of practice for these patients. Monitoring is done with the objective of obtaining data that will contribute to improved chronic disease management. This process includes, but is not limited to, assessment of the adequacy of a exercise program, determination of the adequacy of a specific oxygen delivery device, or the determination of the adequacy of an oxygen prescription in the outpatient setting.

LTOT: Treatment of COPD is largely symptomatic. The only medical interventions that have been shown to reduce mortality are smoking cessation and administration of long-term oxygen therapy (LTOT) in patients with a reduced blood oxygen saturation ("hypoxemia"). LTOT is a mainstay of therapy for COPD and deserves special emphasis because of the recognized beneficial effect on mortality and the labor-intensive nature and expense of this treatment. In fact, the costs of LTOT are critical to any discussion of the cost of care for COPD patients. Recent estimates indicate that approximately one million of the 1.4 million patients receiving LTOT are Medicare beneficiaries [9] and supplemental oxygen is the single most expensive item purchased by Medicare for patients with COPD [4,12]. In 2008, the charges to the Centers for Medicare and Medicaid Services were $2.93 billion [13]. LTOT is a complicated and labor-intensive therapy with multiple components. Only 28% of the total cost of oxygen to Medicare beneficiaries is the equipment. The remainder is related to delivery, maintenance of supplies and equipment, training and education of patients, and the required medical documentation [12]. There has been a long-felt need for the system and method described hereinabove, with its assessment of key clinical parameters obtained while patients are engaged in activities of daily living; for example, testing of the adequacy of an LTOT prescription while patients are engaged in normal activities of daily living [9,10]. A lack of such monitoring in outpatient setting has likely led to many missed opportunities for optimization of treatment.

LTOT is a with well-established treatment modality [1], but there are a number of unresolved problems with its use [14]. Both under-use and overuse of LTOT are national and international concerns [9]. On one hand, recent estimates suggest that many patients with COPD (68%) do not receive appropriate LTOT for treatment of baseline hypoxemia [9,15,16]. This is also true in other chronic lung diseases characterized by progressive hypoxemia. The need for monitoring the adequacy of oxygen supplementation in the outpatient setting is critically important. Underutilization of LTOT leads to untreated hypoxemia that results in increased hospital admissions and deaths [17]. Overutilization of LTOT where efficacy is questionable (during exercise or with transient nocturnal oxygen desaturation) [1,9,14] results in unnecessary expense without benefit.

Furthermore, patient non-compliance with LTOT prescriptions, lack of timely re-evaluation of the need for continuation of therapy, and lack of adequate support services for patients in their homes are all ongoing issues which reduce the effectiveness of LTOT [9,14]. For example, re-assessment of the need for LTOT at 3-months after a disease exacerbation found a sizeable portion of patients were no longer eligible for LTOT, but continued to receive it [9,14]. Since the cost of providing LTOT is increasing by 12-13% annually [14], it is important that over-utilization and under-utilization are effectively addressed. A sizeable portion of inappropriate utilization is linked to the lack of monitoring in the outpatient setting. However, monitoring of hypoxemia in the outpatient setting by medical providers is not part of standard practice and is rarely done, except in a research setting [15,16,17]. The disturbing conclusion is that many patients who could benefit from LTOT are probably not receiving it [17,18]. Finally, identification of suboptimally treated patients who may be deprived of the survival benefit of LTOT is also not part of standard medical practice, since there are no systems designed to address this issue.

Compared to many European countries, the US lacks a detailed reporting system that can track patients and monitor the outcomes of patients on LTOT [19]. Related problems are the lack of data on adherence to prescription guidelines for LTOT and lack of understanding by medical professionals about the reasons for lack of adherence. Since lack of adherence translates into reduced clinical efficacy (increased mortality), this is an important issue to be addressed.

Gaps in Current Management Strategy for COPD:

The recognition of the need for the system and method described herein (also referred to herein as "The COPD Monitor") has grown out of the inventor's clinical experience with management of patients with chronic lung disease. There are serious deficiencies in the use of LTOT. LTOT is part of standard practice for chronic lung disease, but it is still being used in the same way as when it was first implemented decades ago. This and other observations suggested the need for a new system and method that can be used for monitoring of these patients in the outpatient setting. Data obtained from monitoring could be used for more effective management of these patients. Therefore, the rationale for the system and method described herein is based on the recognized deficiencies in the current management of chronic lung disease described in more detail below.

Despite advances in the treatment of COPD, including new bronchodilators and antibiotics, long-term management of patients in the outpatient setting has made limited progress [1,9,14]. An example is the limited application of pulmonary rehabilitation to despite the recognized benefit [1,20,21]. In addition, the lack of appropriate tools for data acquisition and monitoring in the outpatient setting also contributed to this limited progress. In the discussion below, we focus on how various conceptual and technological limitations have interfered with optimal assessment beyond the hospital or clinic setting.

General Points: The current long-term outpatient management strategy for chronic lung disease has several key problems that highlight where the system and method described herein can play a useful role.

There is a lack of focus on disease management in the outpatient setting. Patients spend the majority of their time outside the hospital. Chronic disease management programs that give providers the knowledge and tools for effective disease management in the outpatient setting are underdeveloped [1].

There is a widespread lack of understanding of the potential productive use of data derived from ambulatory monitoring of clinical parameters relevant to COPD outcomes.

There has been a technological lag in development of tools to make accurate measurements of clinical parameters in the outpatient setting that can be applied to disease management [15-17,22,23].

There is a lack of recognition of the consequences of delayed detection of reduced physical function and hypoxemia in the outpatient setting that can lead to an increase in ER visits or hospitalizations [1,9,8,17,20,23,25,26,27,33,34]. The assessment of physical function and detection of hypoxemia in the outpatient setting are not part goals for chronic lung disease management at the present time.

There is a lack of recognition of the problem of patient adherence to LTOT and the importance of overcoming the barriers to adherence that reduce LTOT efficacy [9,14,18,19,24].

In the last 3-4 decades, there have been few changes in the management of chronic lung disease in the outpatient setting beyond improvement in drug therapy. Relevant to the current system and method, there has been little technological innovation focused on improving management using data acquired in the outpatient setting.

Specifically, Related to the Management of Chronic Lung Disease:

1) Long-term management of remains a passive process. Management is often not pro-active. Monitoring of patients in the outpatient setting is not standard practice. Clinicians have few tools to help them assess patients outside the hospital or clinic setting for changes in clinical status. This is unlike the progress made with other chronic diseases in which outpatient management is focused on the needs of the patient. For example, outpatient blood pressure and glucose monitoring have been integrated into the management of patients with hypertension and diabetes to optimize treatment and prevent complications.

2) The current approach to initiation and maintenance of LTOT is a flawed clinical practice: Detection and recognition of significant hypoxemia is suboptimal. In accord with the criticism noted under 1) that management of chronic lung disease is often a passive process, providers typically do not monitor delivery of LTOT or attempt to detect significant hypoxemia in the ambulatory care setting. These aspects of LTOT management are often neglected, rather than having LTOT "individually prescribed, titrated, and periodically monitored for optimal effects" as recommended [9]. A large part of the problem is that the tools to accomplish this goal do not exist. Patients are not proactively evaluated in order to detect hypoxemia as early as possible in order to maximize the benefits of LTOT, including improved survival and quality of life. Finally, patient education concerning optimal use of LTOT is often neglected. All of these factors contribute to blunting the beneficial effects of LTOT, resulting in an increase in disease exacerbations and hospitalizations [17].

Evidence strongly suggests that untreated hypoxemia in the outpatient setting is common in chronic lung disease patients [15-17]. During the course of the disease, patients are found to have the signs of end-organ dysfunction that alerts the provider to the need for oxygen supplementation. A pro-active approach would be to assess the patient for treatable hypoxemia in the outpatient setting at regular intervals in order to detect hypoxemia and reduce end-organ damage. The COPD Monitor is designed to fill this gap in the management strategy. The system and method described herein is an example of a new approach that will enable assessments to be done under the direction of a medical provider.

LTOT efficacy is not monitored where it matters most—the outpatient setting. Current recommendations for use of LTOT state that "supplemental oxygen is administered at rates sufficient to maintain the arterial oxygen saturation at 90% or higher" [1]. Oxygen administration should be titrated to the individual patient's needs Implementing this recommendation is flawed, since the majority of assessments of the adequacy of oxygenation take place in the hospital or clinic setting. LTOT is used in the home setting while patients are engaged in their activities of daily living. Testing the adequacy of an LTOT in this setting is rarely done. Typically, an LTOT prescription is based on a measurement of blood oxygen level at one point in time in the hospital or clinic setting. The concern is that many patients may not be receiving adequate oxygen supplementation during daily activities [15,16].

Another aspect of inadequate monitoring is that a sizeable percentage of patients who are started on LTOT and re-assessed 3-months later often no longer require it. These findings highlight another major flaw in the LTOT management. Reassessment of the need for LTOT is often not done in a timely way, leading to unnecessary continuation of an expensive therapeutic modality [9,18].

Finally, there is no reliable algorithm or prediction formula to ascertain which patients will develop hypoxemia during daily activities and sleep. This is related to the fact that a host of patient factors, including disease severity and other co-morbidities, determine ongoing oxygen desaturation in these patients. Therefore, the only reliable way to detect hypoxemia is to monitor oxygen saturation during daily activities and sleep.

In conclusion, optimization of LTOT can decrease mortality as well as other negative outcomes from hypoxemia, including disease exacerbations and re-hospitalizations that drive up health care costs. On the other hand, unnecessary continuation of LTOT is an waste of medical resources. Failure to optimize LTOT leads to lost opportunities for effective disease management. The system and method described herein provides a way to optimize LTOT in the outpatient setting.

3) Suboptimal patient adherence with LTOT prescription guidelines: There is strong evidence suggesting a major problem with patient adherence to LTOT guidelines, but little progress in addressing this problem [1,24]. This is a complex problem with several components, including patient misinformation concerning the role of LTOT, lack of appropriate provider-patient interaction to address LTOT compliance, prescription of oxygen delivery systems which are not appropriate (too heavy or cumbersome), and other social barriers, including unwillingness to appear in public related to social stigma or increased vulnerability [9,24]. These factors combine to produce a storm of non-adherence that is largely unmeasured and poorly understood.

Compared to European countries, the US lacks a detailed reporting system that tracks patients and monitors outcomes of patients on LTOT [17,19]. A related problem is lack of data on adherence to LTOT guidelines and interest by medical professionals in understanding the reasons for this lack of adherence. An key step forward would be to provide clinicians with the tools to accurately determine compliance that could be used for effective patient education and counseling. This is an important objective since suboptimal patient compliance is linked to increased morbidity and mortality [1,17]. Therefore, one application of the system and method described herein is to provide objective data on patient compliance with LTOT in the outpatient setting.

4) Suboptimal function of many oxygen delivery devices: Another key aspect of the flawed strategy for long-term management of COPD and use of LTOT is the evidence that many oxygen delivery devices often do not work as advertised in providing adequate oxygenation during daily activities. The performance of delivery systems is highly variable. In a study of commercially available systems that purported to supply oxygen supplementation, oxygen saturation in patients during exertion decreased with all units [10]. One unit performed no better than room air. The majority of these systems provide oxygen at fixed flows at all times, or have limited options for changing oxygen liter-flow. These systems are not designed to respond to the needs of a patient during exertion. The result is that patients may not receive adequate supplementation during activities of daily living other than at rest. These authors noted "highly variable" overall performance, "irregular activation" during exertion, and "inconsistent dose" of oxygen delivered during exertion, despite similar technical features.

These findings have stimulated interest in designing more effective delivery systems [28] and highlight a problem with the testing and dissemination of new biomedical devices. Many delivery systems have not undergone appropriate field-testing on human subjects and may not provide adequate oxygenation during exertion [9,10]. Medical providers cannot assume that a specific system is providing for a patient's needs unless that system is actually tested on each patient being treated. The system and method described herein is designed to accomplish this task.

Suboptimal performance of delivery systems also includes the waste of oxygen if there is no mechanism to avoid raising oxygen saturation above 90-92%. Modifications of delivery systems have partially addressed this issue, but there are currently no available systems in routine use that respond directly to fluctuations in the blood oxygen content of the patient during activities of daily living. If blood oxygen saturation is inappropriately high, current systems typically cannot respond by reducing the oxygen liter-flow to the patient, and thus, initiate a more cost-effective use of LTOT. The system and method described herein is designed to accomplish this task.

5) Lack of recognition of the relationship between optimal delivery of LTOT and other clinical outcomes: LTOT has been shown to improve several outcomes in addition to mortality: quality of life, cardiovascular morbidity (pulmonary hypertension), depression, cognitive function, and exercise capacity [1,18,27]. In addition, studies found a reduction of the frequency of hospitalization with LTOT [17]. However, none of these outcomes are routinely monitored as part of long-term management of chronic lung disease. It is reasonable to propose that all such outcomes would be improved if LTOT were optimally delivered. Precedents for the use of outpatient monitoring to improve outcomes in other medical conditions include the use of Holter monitoring to detect cardiac arrhythmias, outpatient blood pressure monitoring to improve control of hypertension, and outpatient blood glucose monitoring to improve diabetes outcomes. This type of proactive approach is largely absent in the current management of chronic lung disease.

6) Lack of widespread recognition of need for individualized management of patients: It is apparent that oxygen delivery systems are not equivalent and vary in their capacity to accomplish the goal of adequate oxygenation during activities of daily living. Given these deficiencies [10], it is imperative that attention be focused on finding the right system for each patient as recommended [9]. This problem is likely to get worse with the continued proliferation of new systems into the marketplace without adequate evaluation in patients. The system and method described herein can address the issue of how to effectively evaluate patients to insure that adequate oxygenation is maintained.

7) Lack of assessment of physical activity in management of chronic lung disease: There is a gap between current management strategy and scientific findings related to the relationship of physical activity to morbidity and mortality in chronic lung disease [8,25,26,27]. Morbidity and mortality are linked to several factors including age, lung function, symptoms (shortness of breath), malnutrition, depression, and systemic inflammation [25]. Recent work has noted the contribution of factors other than respiratory derangements [8,22,23,26]. This work highlights physical activity as a key outcome variable. Physical activity is reduced in chronic lung disease, and linked to several clinical outcomes, including reduced exercise capacity, skeletal muscle weakness, disease exacerbations, hospital readmissions, and mortality [22,23,25,26]. In fact, the level of physical activity is more strongly correlated with mortality than lung function [22]. Therefore, physical activity is a key parameter that can used to assess and modify disease outcome [8,26,33,34]. Despite strong evidence that is probably the single best predictor of all-cause mortality in COPD [25], assessment of physical activity or an appropriate physiological surrogate of the magnitude of breathlessness or exertion (chest wall muscle EMG) is not currently a part of the management of chronic lung disease.

When physical activity is measured in research studies, it is often done using a questionnaire. Direct measurements of physical activity in COPD patients are infrequent. There are limitations in the capabilities of the devices currently used for this purpose, along with limited experience in making these measurements in chronic lung disease [11,26,33]. The system and method described herein is designed to address these issues with the incorporation of multiple sensors in an integrated system designed to measure physical activity and other important related parameters in the outpatient setting. Currently, this type of tool is absent from the clinician's toolbox.

COPD Monitor System and Method: As described below, the COPD Monitor is a new type of device designed to facilitate management of patients with chronic lung disease based on data obtained from outpatient recordings while patients engage in their normal activities of daily living. The device can be worn by the patient at the discretion of a medical provider. The device can monitor several key clinical parameters (heart rate, respiratory rate, blood pressure, oxygenation, physical activity (including rest, exertion, sleep), energy expenditure, and chest wall muscle EMG while the patient is engaged in activities of daily living. These variables were chosen because of their relevance to management of patients with chronic lung disease. The device has the capability to collect and store data over a prolonged recording period (typically a minimum of 24-hours) and transfer these data to a base station computer for analysis and summary. The system and method also typically includes a data analysis process comprised of a number of algorithms that format the acquired data for generation of reports that are used for management by medical providers. Additional key features include the ability to time-stamp data so that the user can easily correlate and determine the temporal profile of events among different parameters. For example, measurement of oxygen saturation during daily activities can be correlated with measurement of the magnitude and type of physical activity, in order to determine if adequate oxygenation during each activity (rest, exertion, sleep) is achieved. This type of analysis can improve patient management by providing an objective basis for decisions based on results obtained in the outpatient setting.

Why the "COPD Monitor" is needed: The system and method described herein has the potential to change the existing paradigm of clinical practice for chronic lung disease. The capability to acquire physiological data during daily activities enable providers to make clinical assessments that were not previously possible. This capability will change how medical providers formulate management plans in patients with chronic lung disease.

The current passive management approach in which providers wait for the next disease exacerbation or hospitalization to occur is in part due to the inability to obtain measurements of key parameters in the outpatient setting. An advantage of the system and method described herein is that a provider can assess patients for changes in clinical status proactively at earlier time points before a patient requires hospitalization. This capability can translate into improved long-term outcomes and reduced health care costs. Use of outpatient data acquisition for disease management is the exception to the rule in current medical practice.

The outpatient environment is where patients spend a majority of their time, and where most therapies are applied.

Lack of monitoring in this setting leads to many missed opportunities for optimization of treatment. The consequences are increased patient morbidity and mortality with more frequent exacerbations and increased use of health care resources. The system and method described herein is a new tool that will enable providers to achieve long-term management goals that were not previously possible.

Clinical Applications of the system and method: The system and method described herein can address many of the gaps in the current strategy for management of chronic lung disease (FIG. 7). Of note, none of the applications below are a part of standard medical practice for the management of chronic lung disease or its equivalent.

1) Monitor oxygenation and physical activity in patients with chronic lung disease with the following goals in mind:

a) Monitor the effectiveness of an LTOT prescription: Determine how effective the prescription is for achieving adequate oxygenation in an individual patient. The current system and method described herein enables the medical provider to obtain objective data about how well the prescription is achieving oxygenation in the outpatient setting. As noted in FIG. 4D, if the patient's oxygenation profile is found to be unacceptable, a new prescription can be initiated to correct this situation.

b) Determine the need for LTOT following an acute disease exacerbation or at another relevant points in time during disease progression.

c) Monitor patient compliance and long-term adherence with an LTOT.

d) Monitor the effectiveness of a specific oxygen delivery system in the outpatient setting with a modification or change of the system, if clinically indicated.

e) Optimize use of LTOT in the outpatient setting from the perspective of the cost-effective use of this medical resource by avoiding inappropriate supplementation when it is not indicated, i.e. where oxygen saturation is above physiological target values.

f) Screening for hypoxemia in patients with less severe disease: monitor patients with chronic lung disease who are not on LTOT to detect hypoxemia in the outpatient setting during daily activities at an earlier point in the disease process. The goal is to identify patients who need LTOT before they develop disease manifestations secondary to hypoxemia.

g) Monitor physical activity and oxygenation in the outpatient setting as part of chronic disease management over extended periods: Physical activity and oxygenation can be monitored to develop a patient-specific activity/oxygenation profile that can be used to make recommendations for adjusting physical activity and/or an LTOT prescription in accord with an individual's performance during an outpatient assessment. Prior recommendations suggested using an indirect test (6-min walk test) as a surrogate measurement of oxygen saturation during daily activities (29), in part because of the purported limitations, difficulties, and inaccuracies of measuring this parameter in the outpatient setting. The present system and method provides a direct assessment of oxygen saturation during daily activities, rendering such indirect testing obsolete.

g) Monitoring of physical activity as an independent outcome factor for patients with chronic lung disease (25, 27).

h) Monitor patients for changes in clinical status over extended time periods following a change in treatment: The addition of new bronchodilator therapy or other drug therapies, the addition of LTOT, or an increase in oxygen flow in a patient already on LTOT can be monitored to assess the effect of such changes on key parameters, including oxygenation, physical activity, energy expenditure, as indices of the effectiveness of this change in treatment.

i) Monitor the effectiveness of a Pulmonary Rehabilitation program: A determination of the activity/oxygenation profile pre/post rehabilitation can be used to make recommendations to extend or increase participation in such a program. Alternatively, the data could be used to make recommendations for changing oxygen liter-flow to treat hypoxemia during exertion.

2) Monitor oxygenation and physical activity in other chronic diseases, including: congestive heart failure and other forms of chronic cardiac disease, pulmonary hypertension, or any chronic cardiopulmonary condition that modifies physical activity, oxygenation, or key aspects of lung function.

3) Monitor patients with sleep-related breathing disorders, such as obstructive sleep apnea, to develop an activity/oxygenation profile: Such data can be used to fine-tune prescriptions for exercise, weight loss, or treatment of nocturnal oxygen desaturation (NOD).

4) Telemedicine monitoring in remote areas: Monitoring patients who do not have ready access to routine medical care is another potential use that can impact chronic disease management and the cost-effectiveness of treatment. The data from remote monitoring of clinical parameters can be transmitted to a base station for analysis and subsequent changes in therapy. In this way, management of these patients can be improved in a cost-effective manner along with preservation of access to medical care.

Summary of Need and Role of method and system described herein that exemplify this proactive approach to disease management in COPD Management: The system and method described herein is an addition to the emerging field of ambulatory monitoring that is designed as a clinical tool to facilitate management of chronic lung disease (or medical equivalent) by medical professionals. Well-known examples of this type of monitoring from other fields include Holter monitoring of cardiac rhythm and monitoring of serum glucose in diabetic patients with hand-held instruments (glucometers) in the outpatient setting. Ambulatory monitoring of clinical parameters in patients with chronic lung disease is not standard medical practice at the present time. Development of monitoring systems and devices for chronic lung disease has been hampered by lack of interest in obtaining information about functional performance of patients in the outpatient setting, coupled with the technical difficulties of making such measurements while patients are engaged in activities of daily living. The system and method is designed to fill this gap by providing the capability to accurately measure relevant parameters over extended time periods. This functionality is then coupled with data analysis of the results that are used to generate reports to guide patient management decisions by medical providers.

To our knowledge, this is the only system and method specifically designed for this purpose in patients with chronic lung disease. This approach constitutes a paradigm shift in the management of chronic lung disease. The system and method is designed with the capability to acquire, analyze, and format the data that is relevant to chronic lung disease management by medical professionals. These key features provide the basis for optimal clinical decision-making compared with patient self-management systems and/or devices that simply collect data in human subjects with little or no analysis of the results. Such systems provide a large stream of data that often is never reviewed by a medical provider.

Projected effects of the system and method described herein on the economics of COPD management: In this section, we analyze the potential economic benefits that can be derived from implementation of the system and method described herein. The medical consequences of missed opportunities for intervention and optimization of the treatment plan in the chronic lung disease patient cohort is increased morbidity and mortality. This translates into a greater societal burden with more frequent exacerbations and hospital admissions that increase the use of health care resources. The economic burden of COPD is related to disease severity [30], providing a rationale for a stronger focus on effective disease management that can identify interventions and strategies aimed at early diagnosis and delayed disease progression as key goals [1,4]. This is where the COPD monitor can have a significant impact on cost of care. Limited progress with smoking cessation in the US and worldwide [1,4,5] guarantees that chronic lung disease will remain a substantial societal burden for many years. This is another strong rationale for a focus on earlier diagnosis and treatment to delay disease progression with new tools like the system and method described herein. The discussion below attempts to conservatively estimate the impact of the COPD monitor on cost of care.

a) Effects on COPD medical costs-acute care: The most important factors which impact the societal cost of chronic lung disease are the chronic, irreversible changes in the lung that characterize this disorder [4]. Utilization statistics are a useful way to begin to approach understanding the disease burden and cost to society. For example, there were 16.3 million physician office/hospital outpatient visits for COPD, 1.5 million emergency department visits, and 673,000 hospital admissions in the United States in 2006 [5]. We estimate that use of the COPD monitor for outpatient assessment and management, and specifically to optimize the delivery of LTOT can conservatively generate a modest 5% savings. For example, a 5% reduction in hospital admissions would produce a savings of ($7100 cost per admission×33,000 admissions=$234,000,000)~$234 million in savings per year [31]. Similarly, a 5% reduction in emergency room visits would produce ($300 cost per ER visit×75,000 ER visits=$22,500,000) an additional ~$22 million in savings per year. Note that the estimate of savings on hospital admissions used a cost figure from 1996 [31]. These two estimates would be additive when applied to this patient population. Based on more recent estimates of the cost of COPD disease exacerbations, emergency room visits, and hospitalizations, the above analysis is a conservative estimate of the cost-savings from use of the COPD monitor [31].

b) Effects on total costs: Patients with chronic lung disease are heavy users of health care [1,5]. Looking at the issue from the perspective of total costs of care in the US, it is possible to derive similar estimates of the impact of using the COPD Monitor. The direct costs for COPD were $18 billion and the indirect costs totaled $14.1 billion in 2002. These costs have ballooned upward significantly. In 2010, the total direct cost for COPD care was $29.5 billion with the following breakdown: $13.2 billion in hospital care, $5.5 billion in physician services, and $5.8 billion in prescription drugs [31,32]. Using a similar conservative estimate for use of the COPD monitor, we estimate that a 5% reduction in total costs of COPD care (for 2010) would lead to a $1.475 billion in direct cost-savings per year. Including indirect costs would increase these savings further.

There are an estimated 24 million patients with COPD in the US. The number of COPD exacerbations each patient has per year is linked strongly to the total health care costs of these patients [31]. Recent work has investigated the cost-savings of reducing the number of exacerbations per annum or reducing the severity of these exacerbations from severe to moderate [31]. In this latter circumstance, it is estimated that $9,409 per patient per year would be saved. Again, using a conservative projection that the COPD monitor would produce this effect in 2% of COPD patients, we estimate the potential savings as follows: $9,409×2% of population of severe COPD patients=$9,409×480,000 patients=~$45 million.

c) Optimization of LTOT: Recent data suggests that optimal use of LTOT is associated with a reduction of the costs of hospitalization [17]. Admission rates and hospital days were reduced ~24% and 44%, respectively, in a COPD patient population. A key strength of this study which supports extrapolation to other countries is that each patient acted as their own control, reducing the effect of differences in other factors, such as co-morbidities. Thus, while optimal implementation of LTOT will contribute to reducing costs associated with hospitalization, it is clear that adherence to prescription guidelines and identification of all hypoxemic COPD patients is not optimal [9,15,16]. Extrapolating these data to the US, we conservatively estimate that hospital admission rates can be reduced by 5%.

Other categories of cost-savings that will not be discussed here in detail include: 1) reductions in durable medical equipment costs; and 2) reductions in lost work productivity [6].

REFERENCES

1. Rabe, K F, Hurd, S, Anzueto, A, Barnes, P J, Buist, S A, Calverley, P, Fukuchi, Y, Jenkins, C, Rodriquez-Roisin, R, van Weel, C, al, e: Global strategy for the diagnosis, management, and prevention of chronic obstructive pulmonary disease: GOLD executive summary American Journal Respiratory Critical Care Medicine 176:532-555, 2007
2. Centers for Disease Control (CDC) and Prevention. Chronic obstructive pulmonary disease among adults-United States, 2011. MMWR. 61:938-943, 2012. http://www.cdc.gov/mmwr/pdf/wk/mm6146.pdf.
3. Watz, H, Waschki, B, Claussen, M, Maagnussen, H: Extrapulmonary effects of chronic obstructive pulmonary disease on physical activity: a cross-sectional study. American Journal Respiratory Critical Care Medicine 177:743-751, 2008.
4. Halpin, D M G, Miravitiles, M: Chronic obstructive pulmonary disease: the disease and its burden to society. Proceedings of American Thoracic Society 3:619-623, 2006.
5. National Institute of Health., Heart, Lung, and Blood Institute: Morbidity and Mortality: 2009 book on cardiovascular, lung, and blood diseases; 2009; http://www.n-hlbi.nih gov/meetings/workshops/oxygen-rx.htm.
6. Ford, E S, Murphy, L B, Khavjou, O, Giles, W H, Holt, J B, Croft, J B: Total and state-specific medical and absentism costs of chronic obstructive pulmonary disease among adults aged>18 yrs in the United States for 2010 and projections through 2020. Chest . . . not yet in print, 2014.
7. Reilly, C C, Ward, K, Jolley, C, Lunt, A C, Steier, J, Elston, C, Polkey, M I, Rafferty, G F, Moxham, J: Neural respiratory drive, pulmonary mechanics, and breathlessness in patients with cystic fibrosis. Thorax 66:240-246, 2011.

8. Garcia-Aymerich, J, Lange, P, Benet, M, Schnohr, P, Anto, J M: Regular physical activity reduces hospital admission and mortality in chronic obstructive pulmonary disease: a population based cohort study. Thorax 61:772-778, 2006.
9. Christopher, K L, Porte, P: Long-term oxygen therapy. Chest 139:430-434, 2011.
10. Palwai, A, Skowronski, M, Coreno, A, Drummond, C, McFadden, E R: Critical comparisons of the clinical performance of oxygen-conserving devices. American Journal Respiratory Critical Care Medicine 181:1061-1071, 2010.
11. Furlanetto, K C, Bisca, G W, Oldemberg, N, Sant'anna, T J, Morakami, F K, Camillo, C A, Cavelheri, V, Hernandes, N A, Probst, V S, Ramos, E M, Brunetto, A F, Pitta, F: Step counting and energy expenditure estimation in patients with chronic obstructive pulmonary disease and healthy elderly: accuracy of two motion sensors. Archives of Physical Medicine and Rehabilitation 91:261-267, 2010.
12. A comprehensive Cost Analysis of Medicare Home Oxygen Therapy. Morrison Informatics, Inc. for American Association for Homecare, 2006.
13. Table V.7. Leading Medicare and Supplier BETOS, Classifications Based on Allowed Charges CY 2007-2008, Centers for Medicare and Medicaid Services/ORDI. Baltimore, Md.: CMS Office of Research, Development, and Information.
14. Oba, Y: Cost-effectiveness of long-term oxygen therapy for chronic obstructive pulmonary disease. The American Journal of Managed Care 15:97-104, 2009.
15. Pilling J, and M Cutaia. Ambulatory oximetry monitoring in patients with severe COPD: a preliminary study. Chest; 116:314-321, 1999.
16. Casanova C, Hernandez C, Sanchez A, Garcia-Talavera, Pablo de Torres J, Abreu J, Valencia J M, Aguirre-Jaime A, Celli B R. Twenty-four hour ambulatory oximetry monitoring in COPD patients with moderate hypoxemia. Respir Care 51:1416-1423, 2006.
17. Ringbaek, T J, Viskum, K, Lange, P: Does long-term oxygen therapy reduce hospitalization in hypoxaemic chronic obstructive pulmonary disease? European Respiratory Journal 20:38-42, 2002.
18. Stoller, J K, Panos, R J, Krachman, S, Doherty, D E, Make, B, et al. Oxygen therapy for patients with COPD: current evidence and long-term treatment trial. Chest 138:179-189, 2010.
19. Ringbaek, T J, Lange, P: The impact of the Danish Oxygen Register on adherence of guidelines for long-term oxygen therapy in COPD patients. Respiratory Medicine 100:218-225, 2006.
20. Spruitt, M A, Singh, S J: Maintenance programs after pulmonary rehabilitation: how may we advance this field? Chest 144:1092-1092, 2013.
21. Beauchamp, M K, Evans, R A, Janaudis-Ferreira, T, Goldstein, R S, Brooks, D: Systematic review of supervised exercise programs after pulmonary rehabilitation in individuals with COPD. Chest 144:1124-1133, 2013.
22. Celli, B, Cote, C G, Lareau, S C, Meek, P M: Predictors of survival in COPD: more than just the FEV1. Respiratory Medicine 102:S27-S35, 2008.
23. Ringbaek, T J, Lange, P: Outdoor activity and performance status as predictors of survival in hypoxemic chronic obstructive pulmonary disease. Clinical Rehabilitation 19:331-338, 2005.
24. Katsenos, S, Constantopoulos, S H: Long-term oxygen therapy in COPD: factors affecting and ways of improving patient compliance. Pulmonary Medicine, article ID: 325362: Sep. 15, 2011.
25. Waschki, B, Kirsten, A, Holz, O, Muller, K C, Meyer, T, Watz, H, Magnussen, H: Physical activity is the strongest predictor of all-cause mortality in patients with COPD: a prospective cohort study. Chest 2011, 140:331-342, 2011.
26. Waschki, B, Spruit, M A, Watz, H, Albert, P S, Shrikrishna, D, Goenen, M, Smith, C, Man, W D C, Tal-Singer, R, Edwards, L D, Calverley, P M A, Magnussen, H, Poikey, M I, Wouters, E F M: Physical activity monitoring in COPD: compliance and associations with clinical characteristics in a multicenter study. Respiratory Medicine 106: 522-530, 2012.
27. Wouters, E F, Franssen, F M E, Spruit, M A: Survival and physical activity in COPD: a giant leap forward. Chest 2011 140:279-281, 2011.
28. Rice, K L, Schmidt, M F, Buan, J S, Lebahn, F, Schwarzock, T K: AccuO2 oximetry-driven oxygen-conserving device versus fixed-dose oxygen devices in stable COPD patients. Respiratory Care 56:1901-1905, 2011.
29. Garcia-Talavera I, Garcia C H, Macario, C C, de Torres J P, Celli B R, Aquirre-Jaime, A: Time to desaturation in the 6-min walking distance test predicts 24-hour oximetry in COPD patients with a $PaO_2$ between 60 and 70 mmHg Respir Med 102:1026-1032, 2008.
30. Menn, P, Heinrich J, Huber, R M, Jones, R A, John, J, Karrasch, S, Peters, A, Schulz, H, Holle, R: Direct medical costs of COPD—an excess cost approach based on two population-based studies. Respiratory Medicine 106: 540-548, 2012.
31. Pasquale, M K, Sun, S X, Song, F, Hartnett, H H, Stemkowski, S A: Impact of exacerbations on health care cost and resource utilization in chronic obstructive pulmonary disease patients with chronic bronchitis from a predominantly Medicare population. International Journal of Chronic Obstructive Pulmonary Disease 7:757-764, 2012.
32. National Institute of Health, National Heart, L, and Blood Institute; Morbidity and Mortality: 2009. Chart Book on Cardiovascular, Lung, and Blood Diseases; Bethesda, Md.; http://www.nhlbi.nih gov/resources/docs/2009_Chartbook_508.pdf.
33. Demeyer, H, Burtin, C, Decramer, M, Van Remoortel, H, Hornikx, M, Langer, D, Gosselink, R, Janssens, W, Troosters, T: Standardizing the analysis of physical activity in patients with COPD following a pulmonary rehabilitation program. Chest 146:318-327, 2014.
34. Vaes, A W, Cheung, A M, Atakhorrami, M, Groenen, M T J, Amft, O, Franssen, M E, Wouters, E F, Spruit, M A: Effect of activity-monitor-based counseling on physical activity and health-related outcomes in patients with chronic diseases: a systematic review and meta-analysis. Ann Med 2013, 45:397-412, 2013.

I claim:

1. An outpatient ambulatory patient worn apparatus for managing chronic lung disease comprising:
a plurality of sensors configured to be worn by a patient and to measure a plurality of physiological data, said plurality of sensors including at least one oximeter, a respiratory rate sensor, and at least one activity or motion sensor, at least said oximeter, said at least one oximeter, said respiratory rate sensor, and said at least one activity or motion sensor continuously operative to measure said plurality of physiological data in an outpatient setting during activities of daily living comprising rest, exertion, and sleep;

a central monitoring unit (CMU) communicatively coupled to said plurality of sensors and to an interface device, said CMU comprising a computer, and said CMU to be worn by the patient in said outpatient setting during activities of daily living, said CMU programmed to record concurrently a set of time stamped primary data comprising measurement data from each of said plurality of sensors to a non-volatile memory at a predetermined interval for one or more epochs of time, and to categorize at an acquisition rate or some multiple of the acquisition rate each recorded measurement of each of said plurality of sensors stored in said set of time stamped primary data by a predominate activity type to generate a set of activity type stamped data, said predominate activity type selected from a plurality of activity types including rest, exertion, and sleep; and a generate report process running on said CMU to provide at least one or more reports in real time including at least an indication or determination of whether a chronic lung disease treatment is needed by the patient based on said set of activity type stamped data.

2. The apparatus of claim 1, wherein said generate report process further generates a report or displays a temporal profile of physical activity during rest, exertion, and sleep.

3. The apparatus of claim 2, wherein said generate report process further generates a report or displays a determination of a temporal profile of a duration and magnitude of physical activity during rest, exertion, and sleep, correlated with a temporal profile of oxygenation.

4. The apparatus of claim 1, wherein said generate report process further generates a report or displays a determination of a frequency, a duration, and a magnitude of one or more hypoxemic events experienced by the patient.

5. The apparatus of claim 1, wherein said generate report process further generates a report or displays a summary of statistics for said plurality of sensors.

6. The apparatus of claim 1, wherein said generate report process further generates a report or displays a comparison of one or more variables between two or more segments of a recording made over two or more different epochs of time.

7. The apparatus of claim 1, wherein said generate report process further generates a report or displays a summary of statistics for a long term oxygen therapy (LTOT) comprising an adequacy of a LTOT prescription, or a degree of a patient compliance with an oxygen prescription of the patient during a selected epoch of time.

8. The apparatus of claim 1, wherein said generate report process further generates a report or displays a summary of statistics for an adequacy of a patient's LTOT delivery system in the patient, or a report of a summary statistics of a comparison of one or more clinical parameters among different patients.

9. The apparatus of claim 1, wherein said CMU is communicatively coupled to an oxygen source or an oxygen delivery unit or to a separate flow meter or adapter flow valve to measure an oxygen flow to the patient.

10. The apparatus of claim 9, wherein said CMU regulates an oxygen flow to the patient based on an adequacy of oxygen delivery to the patient.

11. An outpatient ambulatory patient worn apparatus for regulation of long-term oxygen therapy (LTOT) delivery comprising:

a plurality of sensors configured to be worn by a patient and to measure a plurality of physiological data, said plurality of sensors including at least one oximeter, a respiratory rate sensor, and at least one activity or motion sensor, said at least one oximeter, said respiratory rate sensor, and said at least one activity or motion sensor continuously operative to measure said plurality of physiological data in an outpatient setting during activities of daily living comprising rest, exertion, and sleep;

a central monitoring unit (CMU) communicatively coupled to said plurality of sensors and to an interface device, said CMU comprising a computer, and said CMU to be worn by the patient in said outpatient setting during activities of daily living, said CMU programmed to record concurrently a set of time stamped primary data comprising measurement data from each of said plurality of sensors to a non-volatile memory at a predetermined interval for one or more epochs of time, and to categorize at an acquisition rate or some multiple of the acquisition rate each recorded measurement of each of said plurality of sensors stored in said set of time stamped primary data by a predominate activity type to generate a set of activity type stamped data; and generate report process running on said CMU to provide at least one or more reports in real time at least a selected one of:
   an indication or determination of whether a LTOT treatment is needed by the patient, and
   an indication or determination of a LTOT adequacy of oxygen delivery to the patient, based on said set of activity type stamped data.

12. The LTOT apparatus of claim 11, wherein said predominate activity type comprises one of a plurality of activity types including rest, exertion, and sleep.

13. The LTOT apparatus of claim 11, wherein said CMU is communicatively coupled to an oxygen source or an oxygen delivery unit or to a separate flow meter or adapter flow valve to measure an oxygen flow to the patient.

14. The LTOT apparatus of claim 11, wherein said CMU regulates an oxygen flow to the patient based on said indication or determination of a LTOT adequacy of oxygen delivery to the patient.

15. The LTOT apparatus of claim 11, further comprising a flow valve or an adapter flow valve, and said CMU regulates an oxygen flow to the patient by control of said flow valve or said adapter flow valve in response to a physical activity of the patient as measured by at least one or more of said plurality of sensors or by a chest wall EMG measurement.

16. A method for managing chronic lung disease comprising the steps of:

providing a monitor system comprising:

a plurality of sensors configured to be worn by a patient and to measure a plurality of physiological data, said plurality of sensors including at least one oximeter, a respiratory rate sensor, and at least one activity or motion sensor, said at least one oximeter, said respiratory rate sensor, and said at least one activity or motion sensor continuously operative to measure said plurality of physiological data in an outpatient setting during activities of daily living comprising rest, exertion, and sleep;

a central monitoring unit (CMU) communicatively coupled to said plurality of sensors, said CMU comprising a computer, and said CMU worn by said patient in said outpatient setting during activities of daily living;

recording by said computer concurrently a set of time stamped primary data comprising measurement data from each of said plurality of sensors to a non-volatile memory at a predetermined interval for one or more epochs of time;

categorizing at an acquisition rate or some multiple of the acquisition rate each recorded measurement of each of said plurality of sensors stored in said set of time stamped primary data by a predominate activity type to generate a set of activity type stamped data;

generating and saving to a non-volatile computer memory one or more reports in one or more graphic or tabular clinical-user defined report formats based on said set of activity type stamped data; and recording or displaying said one or more reports to manage a chronic lung disease.

17. The method of claim 16 where said step of providing comprises providing a physical activity sensor.

18. The method of claim 16 where said step of providing comprises providing a movement sensor.

19. The method of claim 16 where said step of providing comprises providing an energy expenditure sensor.

20. The method of claim 16 where said step of providing comprises providing a chest wall muscle EMG sensor.

\* \* \* \* \*